US012297440B2

(12) United States Patent
Meulewaeter et al.

(10) Patent No.: US 12,297,440 B2
(45) Date of Patent: May 13, 2025

(54) REGULATORY NUCLEIC ACID MOLECULES FOR ENHANCING GENE EXPRESSION IN PLANTS

(71) Applicant: BASF SE, Ludwigshafen (DE)

(72) Inventors: Frank Meulewaeter, Ghent (BE); Shirong Zhang, Morrisville, NC (US); Christophe Liseron-Monfils, Ghent (BE)

(73) Assignee: BASF SE, Ludwigshafen am Rhein (DE)

( * ) Notice: Subject to any disclaimer, the term of this patent is extended or adjusted under 35 U.S.C. 154(b) by 395 days.

(21) Appl. No.: 17/609,966

(22) PCT Filed: May 6, 2020

(86) PCT No.: PCT/EP2020/062488
§ 371 (c)(1),
(2) Date: Nov. 9, 2021

(87) PCT Pub. No.: WO2020/229241
PCT Pub. Date: Nov. 19, 2020

(65) Prior Publication Data
US 2022/0220495 A1 Jul. 14, 2022

(30) Foreign Application Priority Data
May 10, 2019 (EP) .................................... 19173869

(51) Int. Cl.
C12N 15/82 (2006.01)
(52) U.S. Cl.
CPC ................ C12N 15/8234 (2013.01)
(58) Field of Classification Search
None
See application file for complete search history.

(56) References Cited

FOREIGN PATENT DOCUMENTS

| CN | 103937799 A | 7/2014 |
|---|---|---|
| WO | WO-2011/023537 A1 | 3/2011 |
| WO | WO-2011/023539 A1 | 3/2011 |
| WO | WO-2013/005152 A1 | 1/2013 |
| WO | WO-2018/113702 A1 | 6/2018 |

OTHER PUBLICATIONS

Geng, et al., "Expression of Wheat High Molecular Weight Glutenin Subunit 1 Bx Is Affected by Large Insertions and Deletions Located in the Upstream Flanking Sequences", PloS One, vol. 9, Issue 8, Aug. 18, 2014, pp. 1-8. (Year: 2014).*
Cloutier et al., Triticum aestivum HMW glutenin x-type subunit Bx7 precursor (Glu-B1al) gene, complete cds. (2005) GenBank accession DQ119142.1, pp. 1-3. (Year: 2005).*
U.S. Appl. No. 61/238,233, filed Aug. 31, 2009, Kuhn, Josef Martin.*
Comai et al., Novel and useful properties of a chimeric plant promoter combining CaMV 35S and MAS elements, (1990), Plant Molecular Biology, vol. 15, pp. 373-381. (Year: 1990).*
Ryan et al., The multiple origins of aluminium resistance in hexaploid wheat include Aegilops tauschii and more recent cis mutations to TaALMT1, (2010), The Plant Journal, vol. 64, pp. 446-455. (Year: 2010).*
Sasaki et al., Sequence Upstream of the Wheat (*Triticum aestivum* L.) ALMT1 Gene and its Relationship to Aluminum Resistance, 2006, Plant & Cell Physiology, vol. 47(10), pp. 1343-1354 (Year: 2006).*
Raman et al., Analysis of TaALMT1 traces the transmission of aluminum resistance in cultivated common wheat (*Triticum aestivum* L.), 2008, Theoretical and Applied Genetics, vol. 116, pp. 343-354 (Year: 2008).*
Han et al., TaALMT1 promoter sequence compositions, acid tolerance, and Al tolerance in wheat cultivars and landraces from Sichuan in China, 2013, Genetics and Molecular Research, vol. 12(4), pp. 5602-5616 (Year: 2013).*
Garcia-Oliveira et al., Molecular characterization of the citrate transporter gene TaMATE1 and expression analysis of upstream genes involved in organic acid transport under Al stress in bread wheat (*Triticum aestivum*), 2014, Physiologia Plantarum, vol. 152(3), pp. 441-452 (Year: 2014).*
Pereira et al., TaALMT1 and TaMATE1B allelic variability in a collection of Brazilian wheat and its association with root growth on acidic soil, 2015, Molecular Breeding, vol. 35(169), pp. 1-16 (Year: 2015).*
Liu et al., Plant synthetic promoters and transcription factors, 2016, Current Opinion in Biotechnology, vol. 37, pp. 36-44. (Year: 2016).*
Meng et al., Genomic editing of intronic enhancers unveils their role in fine-tuning tissue-specific gene expression in *Arabidopsis thaliana*, 2021, The Plant Cell, vol. 33(6), pp. 1997-2014 (Year: 2021).*
EBI Accession No. EM_STD:GU059401, Aegilops tauschii ecotype AUS18913, aluminum-activated malate transporter (ALMT1) gene, exon 1 and partial cds., (Sep. 30, 2010).
EBI Accession No. GSN:BBL36983, Triticum aestivum promoter DNA Pro-1Bx70E fragment, Seq ID:4, (Nov. 6, 2014). [See CN103937799A].
Geng, et al., "Expression of Wheat High Molecular Weight Glutenin Subunit 1Bx Is Affected by Large Insertions and Deletions Located in the Upstream Flanking Sequences", PloS One, vol. 9, Issue 8, Aug. 18, 2014, pp. 1-8.

(Continued)

*Primary Examiner* — Bratislav Stankovic
*Assistant Examiner* — Christina L Meadows
(74) *Attorney, Agent, or Firm* — ArentFox Schiff LLP

(57) ABSTRACT

The present invention is in the field of plant molecular biology and provides methods for production of high expressing promoters and the production of plants with enhanced expression of nucleic acids wherein nucleic acid expression enhancing nucleic acids (NEENAs) are functionally linked to said promoters and/or introduced into plants.

Figure 1:
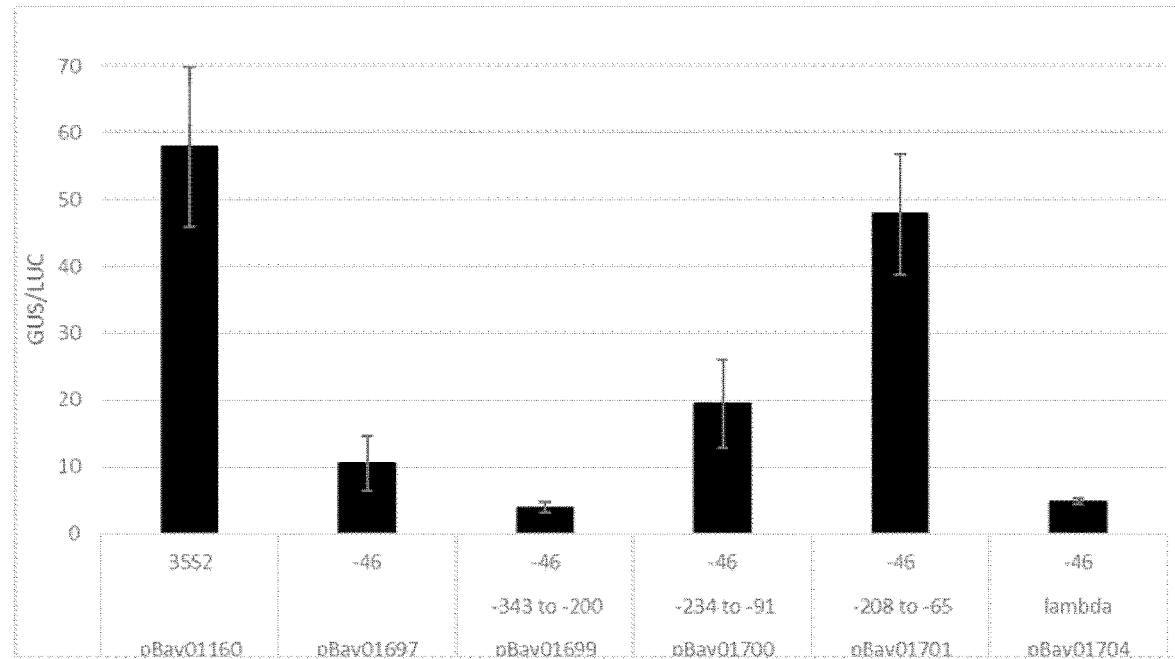

11 Claims, 6 Drawing Sheets
Specification includes a Sequence Listing.

(56) References Cited

OTHER PUBLICATIONS

Hir, et al., "How introns influence and enhance eukaryotic gene expression", Trends in Biochemical Sciences, vol. 28, Issue 4, Apr. 2003, pp. 215-220.
Huang, et al., "Intervening sequences increase efficiency of RNA 3' processing and accumulation of cytoplasmic RNA", Nucleic Acids Research, vol. 18, Issue 4, Feb. 25, 1990, pp. 937-947.
International Application No. PCT/EP2020/062488, International Search Report and Written Opinion, mailed Sep. 10, 2020.
Marand, et al., "Towards genome-wide prediction and characterization of enhancers in plants", Biochimica et Biophysica Acta (BBA)-Gene Regulatory Mechanisms, vol. 1860, Issue 1, Jan. 2017, pp. 131-139.
Nott, et al., "Splicing enhances translation in mammalian cells: an additional function of the exon junction complex", Genes and Development, vol. 18, Jan. 15, 2004, pp. 210-222.
Ryan et al., The mulltiple origins of aluminium resistance in hexaploid wheat include Aegilops tauschii and more recent cis mutations to TaALMT1: evolution of aluminium resistance in wheat, The Plant Journal, 64(3):446-55 (2010).
Zhang, et al., "Allelic variation at the vernalization and photoperiod sensitivity loci in Chinese winter wheat cultivars (*Triticum aestivum* L.)", Frontiers in Plant Science, vol. 6, Article No. 470, Jul. 1, 2015, pp. 1-10.

\* cited by examiner

REGULATORY NUCLEIC ACID MOLECULES FOR ENHANCING GENE EXPRESSION IN PLANTS

CROSS-REFERENCE TO RELATED APPLICATIONS

This is the U.S. national phase of International Application No. PCT/EP2020/062488, filed May 6, 2020, which claims priority to European Patent Application No. 19173869.9, filed May 10, 2019.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "190429_Seqlisting.txt", which was created on Nov. 9, 2021 and is 54,362 bytes in size. The subject matter of the Sequence Listing is incorporated herein in its entirety by reference.

DESCRIPTION OF THE INVENTION

The present invention is in the field of plant molecular biology and provides methods for production of high expressing promoters and the production of plants with enhanced expression of nucleic acids wherein nucleic acid expression enhancing nucleic acids (NEENAs) are functionally linked to said promoters and/or introduced into plants.

Expression of transgenes or cisgenes in plants is strongly affected by various external and internal factors resulting in a variable and unpredictable level of trans- or cisgene expression. Often a high number of transformants must be produced and analyzed to identify lines with desirable expression strength. As transformation and screening of lines with desirable expression strength is costly and labor intensive there is a need for high expression of one or more trans- or cisgenes in a plant. This problem is especially pronounced, when several genes must be coordinately expressed in a trans- or cisgenic plant to achieve a specific effect as a plant has to be identified in which each gene is strongly expressed.

For example, expression of a trans- or cisgene can vary significantly, depending on construct design and positional effects of the T-DNA insertion locus in individual transformation events. Strong promoters can partially overcome these challenges. However, availability of suitable promoters showing strong expression with the desired specificity is often limited. To ensure availability of sufficient promoters with desired expression specificity, the identification and characterization of additional promoters can help to close this gap. However, natural availability of promoters of the respective specificity and strength and the time-consuming characterization of promoter candidates impedes the identification of suitable new promoters.

Furthermore, the development of recombination techniques, genome editing and targeted mutagenesis allows the possibility to modulate the expression level of genes already present in the genome of plants. However, this is limited by the availability of suitable genetic elements capable of modulating the activity of any target promoter.

To overcome these challenges, diverse genetic elements and/or motifs have been shown to positively affect gene expression. Among these, some introns have been recognized as genetic elements with a strong potential for improving gene expression. Although the mechanism is largely unknown, it has been shown that some introns positively affect the steady state amount of mature mRNA, possibly by enhanced transcriptional activity, improved mRNA maturation, enhanced nuclear mRNA export and/or improved translation initiation (e.g. Huang and Gorman, 1990, Nucleic Acid Research 18; Le Hir et al., 2003, Trend Biochem Sci 28; Nott et al., 2004, Genes Dev. 18).

Further, general enhancers have been identified that are not necessarily related to introns. Enhancers are important cis-regulatory DNA elements that regulate transcription programs by recruiting transcription factors and directing them to the promoters of target genes in a cell-type/tissue-specific manner. The expression of a gene can be regulated by one or multiple enhancers (Marand et al 2017; Biochimica and BioBiophysica Acta 1860(131-139). Enhancers are difficult to identify because of their unpredictable positions relative to their cognate promoters. They may be located upstream or downstream of the transcription start site of a certain expressed nucleic acid and may function at positions 5000 or more nucleotides away from the respective promoter. Remarkably, only a handful of enhancers have been identified in plant species largely due to the lack of general approaches for enhancer identification.

Ryan et al ((2010), The Plant Journal 64, pages 446-455) speculate about the gene expression enhancing ability of a tandem repeat located within the *Triticum aestivum* ALMT1 promoter. However, they only show correlation between triplicates of the tandem repeat AB or BC and enhanced gene expression but never involvement of a single element, such as the B element, in enhancement of gene expression.

Geng et al ((2014) PLOS 9(8), e105363) speculate about the correlation of enhanced gene expression and the presence of a 43 nucleotides insertion in *Triticum aestivum* HMW-GS 1Bx7 promoters. However, they show that not all HMW-GS 1Bx7 promoters in *Triticum aestivum* comprising this element show enhanced gene expression. Moreover, the presence of these 43 nucleotides in other *Triticum aestivum* 1Bx promoters was not correlated with enhanced expression. Both findings underline the difficulty in identifying general enhancer elements in plants.

Nucleic acid molecules enhancing expression of functionally linked nucleic acids are in the present application described as "nucleic acid expression enhancing nucleic acids" (NEENA).

DETAILED DESCRIPTION OF THE INVENTION

A first embodiment of the invention comprises a method for the production of a promoter having enhanced expression strength comprising functionally linking to a promoter one or more nucleic acid expression enhancing nucleic acid (NEENA) molecule comprising
  i) the nucleic acid molecule having a sequence as defined in any of SEQ ID NO: 1 or 2, or
  ii) a nucleic acid molecule having a sequence with an identity of 80% or more to any of the sequences as defined by SEQ ID NO:1 or 2, preferably, the identity is 85% or more, more preferably the identity is 90% or more, even more preferably, the identity is 95% or more, 96% or more, 97% or more, 98% or more or 99% or more, in the most preferred embodiment, the identity is 100% to any of the sequences as defined by SEQ ID NO: 1 or 2, or
  iii) a nucleic acid molecule of 30 nucleotides or more, 40 nucleotides or more, 50 nucleotides or more or 100 nucleotides or more, hybridizing under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably 65° C. to a nucleic acid molecule comprising at least 30, preferably at least 40, more preferably at least 50, even more preferably at least 100, most preferably at least 150 consecutive nucleotides of a transcription enhancing nucleotide sequence of SEQ ID NO:1 or 2, or the complement thereof. Preferably, said nucleic acid molecule is hybridizing under conditions equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C. to a nucleic acid molecule comprising at least 30, preferably at least 40, more preferably at least 50, even more preferably at least 100, most preferably at least 150 consecutive nucleotides of a transcription enhancing nucleotide sequence of SEQ ID NO:1 or 2, or the complement thereof, more preferably, said nucleic acid molecule is hybridizing under conditions equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. to a nucleic acid molecule comprising at least 30, preferably at least 40, more preferably at least 50, even more preferably at least 100, most preferably at least 150 consecutive nucleotides of a transcription enhancing nucleotide sequence described by any of the sequences of SEQ ID NO:1 or 2, or the complement thereof iv) a fragment of 30 or more consecutive bases, preferably 40 or more consecutive bases, more preferably 50 consecutive bases or more even more preferably 100 or more consecutive bases of a nucleic acid molecule of i) to iii) which has an expressing enhancing activity, for example 65% or more, preferably 70% or more, more preferably 75% or more, even more preferably 80% or more, 85% or more or 90% or more, in a most preferred embodiment it has 95% or more of the expression enhancing activity as the corresponding nucleic acid molecule having the sequence of any of the sequences as defined by SEQ ID NO: 1 or 2, or v) a nucleic acid molecule having a sequence as defined in any of SEQ ID NO: 1 or 2, further comprising insertion, deletion, substitution of at least 1 nucleotide up to 20 nucleotides, at least 1 nucleotide up to 15 nucleotides, at least 1 nucleotide up to 10 nucleotides, at least 1 nucleotide up to 5 nucleotides, at least 1 nucleotide up to 4 nucleotides, at least 1 nucleotide up to 3 nucleotides, or even at least 1 nucleotide up to 2 nucleotides, or vi) a nucleic acid molecule which is the complement or reverse complement of any of the previously mentioned nucleic acid molecules under i) to vi).

The fragment having an expressing enhancing activity may comprise the nucleotide sequence of SEQ ID NO: 1 from nucleotide position 1 to nucleotide position 30, the nucleotide sequence of SEQ ID NO: 1 from nucleotide position 1 to nucleotide position 35, the nucleotide sequence of SEQ ID NO: 1 from nucleotide position 1 to nucleotide position 40, the nucleotide sequence of SEQ ID NO: 1 from nucleotide position 3 to nucleotide position 33, the nucleotide sequence of SEQ ID NO: 1 from nucleotide position 3 to nucleotide position 38, the nucleotide sequence of SEQ ID NO: 1 from nucleotide position 3 to nucleotide position 43, the nucleotide sequence of SEQ ID NO: 1 from nucleotide position 8 to nucleotide position 38, the nucleotide sequence of SEQ ID NO: 1 from nucleotide position 8 to nucleotide position 43, the nucleotide sequence of SEQ ID NO: 1 from nucleotide position 13 to nucleotide position 43, the nucleotide sequence of SEQ ID NO: 2 from nucleotide position 1 to nucleotide position 30, the nucleotide sequence of SEQ ID NO: 2 from nucleotide position 1 to nucleotide position 35, the nucleotide sequence of SEQ ID NO: 2 from nucleotide position 1 to nucleotide position 40, the nucleotide sequence of SEQ ID NO: 2 from nucleotide position 1 to nucleotide position 45, the nucleotide sequence of SEQ ID NO: 2 from nucleotide position 1 to nucleotide position 50, the nucleotide sequence of SEQ ID NO: 2 from nucleotide position 1 to nucleotide position 55, the nucleotide sequence of SEQ ID NO: 2 from nucleotide position 1 to nucleotide position 60, the nucleotide sequence of SEQ ID NO: 2 from nucleotide position 1 to nucleotide position 65, the nucleotide sequence of SEQ ID NO: 2 from nucleotide position 1 to nucleotide position 70, the nucleotide sequence of SEQ ID NO: 2 from nucleotide position 1 to nucleotide position 75, the nucleotide sequence of SEQ ID NO: 2 from nucleotide position 1 to nucleotide position 80, the nucleotide sequence of SEQ ID NO: 2 from nucleotide position 1 to nucleotide position 85, the nucleotide sequence of SEQ ID NO: 2 from nucleotide position 1 to nucleotide position 90, the nucleotide sequence of SEQ ID NO: 2 from nucleotide position 1 to nucleotide position 95, the nucleotide sequence of SEQ ID NO: 2 from nucleotide position 1 to nucleotide position 100, the nucleotide sequence of SEQ ID NO: 2 from nucleotide position 1 to nucleotide position 105, the nucleotide sequence of SEQ ID NO: 2 from nucleotide position 5 to nucleotide position 35, the nucleotide sequence of SEQ ID NO: 2 from nucleotide position 5 to nucleotide position 40, the nucleotide sequence of SEQ ID NO: 2 from nucleotide position 5 to nucleotide position 45, the nucleotide sequence of SEQ ID NO: 2 from nucleotide position 5 to nucleotide position 50, the nucleotide sequence of SEQ ID NO: 2 from nucleotide position 5 to nucleotide position 55, the nucleotide sequence of SEQ ID NO: 2 from nucleotide position 5 to nucleotide position 60, the nucleotide sequence of SEQ ID NO: 2 from nucleotide position 5 to nucleotide position 65, the nucleotide sequence of SEQ ID NO: 2 from nucleotide position 5 to nucleotide position 70, the nucleotide sequence of SEQ ID NO: 2 from nucleotide position 5 to nucleotide position 75, the nucleotide sequence of SEQ ID NO: 2 from nucleotide position 5 to nucleotide position 80, the nucleotide sequence of SEQ ID NO: 2 from nucleotide position 5 to nucleotide position 85, the nucleotide sequence of SEQ ID NO: 2 from nucleotide position 5 to nucleotide position 90, the nucleotide sequence of SEQ ID NO: 2 from nucleotide position 5 to nucleotide position 95, the nucleotide sequence of SEQ ID NO: 2 from nucleotide position 5 to nucleotide position 100, the nucleotide sequence of SEQ ID NO: 2 from nucleotide position 5 to nucleotide position 105, the nucleotide sequence of SEQ ID NO: 2 from nucleotide position 10 to nucleotide position 40, the nucleotide sequence of SEQ ID NO: 2 from nucleotide position 10 to nucleotide position 45, the nucleotide sequence of SEQ ID NO: 2 from nucleotide position 10 to nucleotide position 50, the nucleotide sequence of SEQ ID NO: 2 from nucleotide position 10 to nucleotide position 55, the nucleotide sequence of SEQ ID NO: 2 from nucleotide position 10 to nucleotide position 60, the nucleotide sequence of SEQ ID NO: 2 from nucleotide position 10 to nucleotide position 65, the nucleotide sequence of SEQ ID NO: 2 from nucleotide position 10 to nucleotide position 70, the nucleotide sequence of SEQ ID NO: 2 from nucleotide position 10 to nucleotide position 75, the nucleotide sequence of SEQ ID NO: 2 from nucleotide position 10 to nucleotide position 80, the nucleotide sequence of SEQ ID NO: 2 from nucleotide position 10 to nucleotide position 85, the nucleotide sequence of SEQ ID NO: 2 from nucleotide position 10 to nucleotide position 90, the nucleotide sequence of SEQ ID NO: 2 from nucleotide position 10 to nucleotide position 95, the nucleotide sequence of SEQ ID NO: 2 from nucleotide position 10 to nucleotide position 100, the nucleotide sequence of SEQ ID NO: 2 from nucleotide position 10 to nucleotide position 105, the nucleotide sequence of SEQ ID NO: 2 from nucleotide position 15 to nucleotide position 45, the nucleotide sequence of SEQ ID NO: 2 from nucleotide position 15 to nucleotide position 50, the nucleotide sequence of SEQ ID NO: 2 from nucleotide position 15 to nucleotide position 55, the nucleotide sequence of SEQ ID NO: 2 from nucleotide position 15 to nucleotide position 60, the nucleotide sequence of SEQ ID NO: 2 from nucleotide position 15 to nucleotide position 65, the nucleotide sequence of SEQ ID NO: 2 from nucleotide position 15 to nucleotide position 70, the nucleotide sequence of SEQ ID NO: 2 from nucleotide position 15 to nucleotide position 75, the nucleotide sequence of SEQ ID NO: 2 from nucleotide position 15 to nucleotide position 80, the nucleotide sequence of SEQ ID NO: 2 from nucleotide position 15 to nucleotide position 85, the nucleotide sequence of SEQ ID NO: 2 from nucleotide position 15 to nucleotide position 90, the nucleotide sequence of SEQ ID NO: 2 from nucleotide position 15 to nucleotide position 95, the nucleotide sequence of SEQ ID NO: 2 from nucleotide position 15 to nucleotide position 100, the nucleotide sequence of SEQ ID NO: 2 from nucleotide position 15 to nucleotide position 105, the nucleotide sequence of SEQ ID NO: 2 from nucleotide position 20 to nucleotide position 50, the nucleotide sequence of SEQ ID NO: 2 from nucleotide position 20 to nucleotide position 55, the nucleotide sequence of SEQ ID NO: 2 from nucleotide position 20 to nucleotide position 60, the nucleotide sequence of SEQ ID NO: 2 from nucleotide position 20 to nucleotide position 65, the nucleotide sequence of SEQ ID NO: 2 from nucleotide position 20 to nucleotide position 70, the nucleotide sequence of SEQ ID NO: 2 from nucleotide position 20 to nucleotide position 75, the nucleotide sequence of SEQ ID NO: 2 from nucleotide position 20 to nucleotide position 80, the nucleotide sequence of SEQ ID NO: 2 from nucleotide position 20 to nucleotide position 85, the nucleotide sequence of SEQ ID NO: 2 from nucleotide position 20 to nucleotide position 90, the nucleotide sequence of SEQ ID NO: 2 from nucleotide position 20 to nucleotide position 95, the nucleotide sequence of SEQ ID NO: 2 from nucleotide position 20 to nucleotide position 100, the nucleotide sequence of SEQ ID NO: 2 from nucleotide position 20 to nucleotide position 105, the nucleotide sequence of SEQ ID NO: 2 from nucleotide position 25 to nucleotide position 55, the nucleotide sequence of SEQ ID NO: 2 from nucleotide position 25 to nucleotide position 60, the nucleotide sequence of SEQ ID NO: 2 from nucleotide position 25 to nucleotide position 65, the nucleotide sequence of SEQ ID NO: 2 from nucleotide position 25 to nucleotide position 70, the nucleotide sequence of SEQ ID NO: 2 from nucleotide position 25 to nucleotide position 75, the nucleotide sequence of SEQ ID NO: 2 from nucleotide position 25 to nucleotide position 80, the nucleotide sequence of SEQ ID NO: 2 from nucleotide position 25 to nucleotide position 85, the nucleotide sequence of SEQ ID NO: 2 from nucleotide position 25 to nucleotide position 90, the nucleotide sequence of SEQ ID NO: 2 from nucleotide position 25 to nucleotide position 95, the nucleotide sequence of SEQ ID NO: 2 from nucleotide position 25 to nucleotide position 100, the nucleotide sequence of SEQ ID NO: 2 from nucleotide position 25 to nucleotide position 105, the nucleotide sequence of SEQ ID NO: 2 from nucleotide position 30 to nucleotide position 60, the nucleotide sequence of SEQ ID NO: 2 from nucleotide position 30 to nucleotide position 65, the nucleotide sequence of SEQ ID NO: 2 from nucleotide position 30 to nucleotide position 70, the nucleotide sequence of SEQ ID NO: 2 from nucleotide position 30 to nucleotide position 75, the nucleotide sequence of SEQ ID NO: 2 from nucleotide position 30 to nucleotide position 80, the nucleotide sequence of SEQ ID NO: 2 from nucleotide position 30 to nucleotide position 85, the nucleotide sequence of SEQ ID NO: 2 from nucleotide position 30 to nucleotide position 90, the nucleotide sequence of SEQ ID NO: 2 from nucleotide position 30 to nucleotide position 95, the nucleotide sequence of SEQ ID NO: 2 from nucleotide position 30 to nucleotide position 100, the nucleotide sequence of SEQ ID NO: 2 from nucleotide position 30 to nucleotide position 105, the nucleotide sequence of SEQ ID NO: 2 from nucleotide position 35 to nucleotide position 65, the nucleotide sequence of SEQ ID NO: 2 from nucleotide position 35 to nucleotide position 70, the nucleotide sequence of SEQ ID NO: 2 from nucleotide position 35 to nucleotide position 75, the nucleotide sequence of SEQ ID NO: 2 from nucleotide position 35 to nucleotide position 80, the nucleotide sequence of SEQ ID NO: 2 from nucleotide position 35 to nucleotide position 85, the nucleotide sequence of SEQ ID NO: 2 from nucleotide position 35 to nucleotide position 90, the nucleotide sequence of SEQ ID NO: 2 from nucleotide position 35 to nucleotide position 95, the nucleotide sequence of SEQ ID NO: 2 from nucleotide position 35 to nucleotide position 100, the nucleotide sequence of SEQ ID NO: 2 from nucleotide position 35 to nucleotide position 105, the nucleotide sequence of SEQ ID NO: 2 from nucleotide position 40 to nucleotide position 70, the nucleotide sequence of SEQ ID NO: 2 from nucleotide position 40 to nucleotide position 75, the nucleotide sequence of SEQ ID NO: 2 from nucleotide position 40 to nucleotide position 80, the nucleotide sequence of SEQ ID NO: 2 from nucleotide position 40 to nucleotide position 85, the nucleotide sequence of SEQ ID NO: 2 from nucleotide position 40 to nucleotide position 90, the nucleotide sequence of SEQ ID NO: 2 from nucleotide position 40 to nucleotide position 95, the nucleotide sequence of SEQ ID NO: 2 from nucleotide position 40 to nucleotide position 100, the nucleotide sequence of SEQ ID NO: 2 from nucleotide position 40 to nucleotide position 105, the nucleotide sequence of SEQ ID NO: 2 from nucleotide position 45 to nucleotide position 75, the nucleotide sequence of SEQ ID NO: 2 from nucleotide position 45 to nucleotide position 80, the nucleotide sequence of SEQ ID NO: 2 from nucleotide position 45 to nucleotide position 85, the nucleotide sequence of SEQ ID NO: 2 from nucleotide position 45 to nucleotide position 90, the nucleotide sequence of SEQ ID NO: 2 from nucleotide position 45 to nucleotide position 95, the nucleotide sequence of SEQ ID NO: 2 from nucleotide position 45 to nucleotide position 100, the nucleotide sequence of SEQ ID NO: 2 from nucleotide position 45 to nucleotide position 105, the nucleotide sequence of SEQ ID NO: 2 from nucleotide position 50 to nucleotide position 80, the nucleotide sequence of SEQ ID NO: 2 from nucleotide position 50 to nucleotide position 85, the nucleotide sequence of SEQ ID NO: 2 from nucleotide position 50 to nucleotide position 90, the nucleotide sequence of SEQ ID NO: 2 from nucleotide position 50 to nucleotide position 95, the nucleotide sequence of SEQ ID NO: 2 from nucleotide position 50 to nucleotide position 100, the nucleotide sequence of SEQ ID NO: 2 from nucleotide position 50 to nucleotide position 105, the nucleotide sequence of SEQ ID NO: 2 from nucleotide position 55 to nucleotide position 85, the nucleotide sequence of SEQ ID NO: 2 from nucleotide position 55 to nucleotide position 90, the nucleotide sequence of SEQ ID NO: 2 from nucleotide position 55 to nucleotide position 95, the nucleotide sequence of SEQ ID NO: 2 from nucleotide position 55 to nucleotide position 100, the nucleotide sequence of SEQ ID NO: 2 from nucleotide position 55 to nucleotide position 105, the nucleotide sequence of SEQ ID NO: 2 from nucleotide position 60 to nucleotide position 90, the nucleotide sequence of SEQ ID NO: 2 from nucleotide position 60 to nucleotide position 95, the nucleotide sequence of SEQ ID NO: 2 from nucleotide position 60 to nucleotide position 100, the nucleotide sequence of SEQ ID NO: 2 from nucleotide position 60 to nucleotide position 105, the nucleotide sequence of SEQ ID NO: 2 from nucleotide position 65 to nucleotide position 95, the nucleotide sequence of SEQ ID NO: 2 from nucleotide position 65 to nucleotide position 100, the nucleotide sequence of SEQ ID NO: 2 from nucleotide position 65 to nucleotide position 105, the nucleotide sequence of SEQ ID NO: 2 from nucleotide position 70 to nucleotide position 100, the nucleotide sequence of SEQ ID NO: 2 from nucleotide position 70 to nucleotide position 105, or the nucleotide sequence of SEQ ID NO: 2 from nucleotide position 75 to nucleotide position 105.

In one embodiment, the one or more NEENA is heterologous to the promoter to which it is functionally linked.

In a further embodiment the NEENA of the invention is introduced into a promoter at a position which at the 5' end and/or 3' end is adjacent to sequences that are not naturally adjacent to the NEENA of the invention, e.g. in the genome of a WT plant.

In another embodiment of the invention 2 or less copies of the NEENA of the invention are introduced into the promoter.

In principal the NEENA may be functionally linked to any promoter such as tissue specific, inducible, developmental specific or constitutive promoters. The respective NEENA will lead to an enhanced expression of the heterologous nucleic acid under the control of the respective promoter to which the at least one NEENA is functionally linked to.

The one or more NEENA may be functionally linked to any promoter and will enhance expression of the nucleic acid molecule under control of said promoter. Constitutive promoters to be used in any method of the invention may be derived from plants, for example monocotyledonous or dicotyledonous plants, from bacteria and/or viruses or may be synthetic promoters. Constitutive promoters to be used are for example the Cassava vein mosaic virus-Promoter (Verdaguer B et al. (1996). PMB 31(6), 1129-39), the Subterrenean Clover Stunt Virus-Promoter (Boevink P, et al. (1995). Virology 207(2), 354-61), the *A. thaliana* histone 4A promoter in combination with the histone 3A intron (Chaboute et al. (1984). PMB 8(2), 179-91), the *B. napus* P450-dependent fatty acid omega-hydroxylase promoter (WO2016113333), the pAct10s promoter from rice (McElroy et al. (1990). Plant Cell 2(2), 163-71), the PcUbi-Promoter from *P. crispum* (WO 2003102198), the ZmUbi-Promoter from *Zea mays* (Christensen et al (1992). Plant Mol Biol. 18(4), 675-89), AtNit-promoter from the *A. thaliana* gene At3g44310 encoding nitrilase 1, the 34S-promoter from figwort mosaic virus (Sanger et al., 1990, PMB 14(3)), the 35S-promoter from Cauliflower mosaic virus (Odell et al (1985). Nature 313(6005), 810-2), the nos (Depicker et al (1982). J Mol Appl Genet. 1(6), 561-73) and ocs-promoter derived from *Agrobacterium tumefaciens*, the ScBV-promoter (U.S. Pat. No. 5,994,123), the SUPER-promoter (Lee et al. 2007, Plant. Phys. 145), the AtFNR-promoter from the *A. thaliana* gene At5g66190 encoding the ferredoxin NADH reductase, the ptxA promoter from *Pisum sativum* (WO2005085450), the AtTPT-promoter from the *A. thaliana* gene At5g46110 encoding the triose phosphate translocator, the bidirectional AtOASTL-promoter from the *A. thaliana* genes At4g14880 and At4g14890, the PRO0194 promoter from the *A. thaliana* gene At1g13440 encoding the glyceraldehyde-3-phosphate dehydrogenase, the PRO0162 promoter from the *A. thaliana* gene At3g52930 encoding the fructose-bis-phosphate aldolase, the AHAS-promoter (WO2008124495), the CaffeoylCoA-MT promoter and the OsCP12 from rice (WO2006084868) or the pGOS2 promoter from rice (de Pater et al. (1992). Plant J. 2(6), 837-44).

Tissue or developmental specific or inducible promoters to be used in any method of the invention may be derived from plants, for example monocotyledonous or dicotyledonous plants, from bacteria and/or viruses or may be synthetic promoters. Tissue or developmental specific or inducible promoters to be used are for example the seed specific and/or seed-preferential promoters for example the High Molecular Weight Glutenin Bx17 promoter from *T. aestivum* (Reddy P and Appels R (1993) Theor Appl Genet. 85(5), 616-24), High Molecular Weight Glutenin 1Dx5 promoter from *T. aestivum* (Lamacchia et al. (2001) J Exp Bot. 52(355), 243-50), the plastidic AGPase promoter from *T. aestivum* (Thorneycroft et al. (2003) Plant Biotechnol J. 1(4), 259-70), the hordein B1 promoter from *Hordeum vulgare* (Brandt et al. (1985) Carlsberg Research Communications 50, 333), the SBP-promoter from *Vicia faba* (WO2000026388), the Unknown Seed Protein-promoter (USP) from *Vicia faba* (WO2003092362), the napin promoter from *Brassica napus* (EP0255378), the conlinin-promoter from *Linum usitatissimum* (WO2001016340), the promoter from the *A. thaliana* gene At5g01670 encoding the peroxiredoxin like protein (WO2006089950), the promoter of the peroxiredoxin like protein from *Linum usitatissmum* (WO2006089950), the globulin like protein promoter from *Brassica napus* (Roh et al., 2014, Journal of the Korean Society for Applied Biological Chemistry 57(5)), the arcelin5-1 promoter from *Phaseolus vulgaris* (WO 2012077020), the Zein promoter from *Zea mays* (Shepherd and Scott Biotechnol Appl Biochem. 2009, 52(3)), the globulin promoter from *Zea mays* (Mei et al., 2004, Maydica 49(4)), the pKG86 promoter from *Zea mays* (WO 2010122110), the leaf specific ST-LS1 promoter from *Solanum tuberosum* (Stockhaus et al (1989) EMBO J. 8(9), 2445-51), the leaf specific thioredoxin promoter from *Oryza sativa* (Fukuda et al. (2005) Plant Cell Physiol. 46(11), 1779-86), the root specific or root preferential promoters Pbtg-26D from *G. hirsutum* (WO2017/025282), PGL4 and 5 from *Zea mays* (EP1862473) or Pzrp2 from *Zea mays* (Held et al. (1997) PMG 35(3), 367-375), the inducible promoters Phpr1 from *A. thaliana* (Wang et al. (2009) Molecular Plant 2(1), 191-200), the rd29a promoter from *A. thaliana* (Yamaguchi-Shinozaki K and Shinozaki K (1994) Plant Cell 6(2), 251-64), the proteinase inhibitor promoter from *Zea mays* (Cordero et al (1994) Plant J. 6(2), 141-50), or the fiber specific or preferential promoters from *G. hirsutum* as described in WO2012093032, US2013081154, WO2004065571, WO2008083969 or WO2012136788.

The high expression promoters of the invention functionally linked to a NEENA may be employed in any plant comprising for example moss, fern, gymnosperm or angiosperm, for example monocotyledonous or dicotyledonous plant. In a preferred embodiment said promoter of the invention functionally linked to a NEENA may be employed in monocotyledonous or dicotyledonous plants, preferably crop plant such as corn, soy, canola, cotton, potato, sugar beet, rice, wheat, sorghum, barley, musa, sugarcane, miscanthus and the like. In a preferred embodiment of the invention, said promoter which is functionally linked to a NEENA may be employed in monocotyledonous crop plants such as corn, rice, wheat, sorghum, musa, miscanthus, sugarcane or barley. In an especially preferred embodiment the promoter functionally linked to a NEENA may be employed in wheat.

A high expressing promoter as used in the application means for example a promoter which is functionally linked to a NEENA causing enhanced expression of the promoter in a plant or part thereof wherein the accumulation of RNA or rate of synthesis of RNA derived from the nucleic acid molecule under the control of the respective promoter functionally linked to a NEENA is higher, preferably significantly higher than the expression caused by the same promoter lacking a NEENA of the invention. Preferably the amount of RNA of the respective nucleic acid and/or the rate of RNA synthesis and/or the RNA stability in a plant is increased 50% or more, for example 100% or more, preferably 200% or more, more preferably 5 fold or more, even more preferably 10 fold or more, most preferably 20 fold or more for example 50 fold compared to a control plant of same age grown under the same conditions comprising the same promoter the latter not being functionally linked to a NEENA of the invention.

When used herein, significantly higher refers to statistical significance the skilled person is aware how to determine, for example by applying statistical tests such as the t-test to the respective data sets.

Methods for detecting expression conferred by a promoter are known in the art. For example, the promoter may be functionally linked to a marker gene such as GUS, GFP or luciferase and the activity of the respective protein encoded by the respective marker gene may be determined in the plant or part thereof. As a representative example, the method for detecting luciferase is described in detail below. Other methods are for example measuring the steady state level or synthesis rate of RNA of the nucleic acid molecule controlled by the promoter by methods known in the art, for example Northern blot analysis, qPCR, run-on assays or other methods described in the art.

A skilled person is aware of various methods for functionally linking two or more nucleic acid molecules. Such methods may encompass restriction/ligation, ligase independent cloning, recombineering, recombination or synthesis. Other methods may be employed to functionally link two or more nucleic acid molecules.

A further embodiment of the present invention is a method for producing a plant or part thereof with, compared to a respective control plant or part thereof, enhanced expression of one or more nucleic acid molecule comprising the steps of introducing into the plant or part thereof one or more NEENA comprising a nucleic acid molecule as defined above under i) to vi) and functionally linking said one or more NEENA to a promoter and to a nucleic acid molecule being under the control of said promoter, wherein the NEENA is heterologous to said nucleic acid molecule. The NEENA may be heterologous to the nucleic acid molecule which is under the control of said promoter to which the NEENA is functionally linked or it may be heterologous to both the promoter and the nucleic acid molecule under the control of said promoter.

The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. For example, a NEENA of the invention is in its natural environment functionally linked to its native promoter, whereas in the present invention it is linked to another promoter which might be derived from the same organism, a different organism or might be a synthetic promoter such as the SUPER-promoter. It may also mean that the NEENA of the present invention is linked to its native promoter but the nucleic acid molecule under control of said promoter is heterologous to the promoter comprising its native NEENA. It is in addition to be understood that the promoter and/or the nucleic acid molecule under the control of said promoter functionally linked to a NEENA of the invention are heterologous to said NEENA as their sequence has been manipulated by for example mutation such as insertions, deletions and the forth so that the natural sequence of the promoter and/or the nucleic acid molecule under control of said promoter is modified and therefore have become heterologous to a NEENA of the invention. It may also be understood that the NEENA is heterologous to the nucleic acid to which it is functionally linked when the NEENA is functionally linked to its native promoter wherein the position of the NEENA in relation to said promoter is changed so that the promoter shows higher expression after such manipulation.

A plant exhibiting enhanced expression of a nucleic acid molecule as meant herein means a plant having a higher, preferably statistically significant higher expression of a nucleic acid molecule compared to a control plant grown under the same conditions without the respective NEENA functionally linked to the respective nucleic acid molecule. Such control plant may be a wild-type plant or a trans- or cisgenic plant comprising the same promoter controlling the same gene as in the plant of the invention wherein the promoter is not linked to a NEENA of the invention. Producing a plant as used herein comprises methods for stable transformation such as introducing a recombinant DNA construct into a plant or part thereof by means of *Agrobacterium* mediated transformation, protoplast transformation, particle bombardment or the like and optionally subsequent regeneration of a trans- or cisgenic plant.

It also comprises methods for transient transformation of a plant or part thereof such as viral infection or *Agrobacterium* infiltration. A skilled person is aware of further methods for stable and/or transient transformation of a plant or part thereof.

Approaches such as protoplast fusion or recombination techniques using a donor DNA might also be employed for production of a plant of the invention and are covered herewith. For example, a single strand break (nick) or a double strand break may be introduced into the genome of a plant using recombinant technologies known in the art such as TALEN (WO12138939, WO12138927); Zink finger proteins (WO02057293, WO05084190), homing endonucleases (WO11104382, WO14199358) or nucleic acid guided nucleases such as AGO, Cas9 or Cas12 (WO13141680, WO13176772, WO14093595, WO15157534 or WO16205711). Together with the introduction of such single- or double strand break inducing agents, one or more donor DNA (WO13176772, WO14089290) may be introduced into the plant or part thereof comprising the NEENA molecule flanked by nucleic acid molecules comprising sequences essentially identical or essentially complementary to the regions adjacent to the nick or double strand break thereby facilitating homologous recombination and introducing the NEENA molecule into the genome of the plant or part thereof.

Further, the sequence of a NEENA of the invention may be introduced into the genome and functionally linked to the respective heterologous promoter by introducing into the genome a series of point mutations using technologies such as deaminases (WO0058480, WO18027078) and the like which may be directed to a specific region in the genome of a plant or part thereof by fusing the mutating polypeptide portion e.g. a deaminase or glycosidase to a DNA binding polypeptide such as, for example a TALEN, a Zinc finger protein, a homing endonuclease or an RNA guided nuclease, nickase or inactivated nuclease such as Cas9 or Cas12, as described in WO15089406, US2017321210, WO015133554 or WO17070632. By application of these methods, the NEENA sequence is introduced into the genome without introduction of a heterologous molecule but the NEENA sequence replaces another sequence in the genome. Such technologies are encompassed by the term "integrate" or "introducing" an NEENA sequence or "integrating" or "introducing" a NEENA molecule into the genome and functionally linking such sequences and/or molecules to a heterologous promoter.

The method of the invention may be applied to any plant, for example gymnosperm or angiosperm, preferably angiosperm, for example dicotyledonous or monocotyledonous plants, preferably monocotyledonous plants. Preferred monocotyledonous plants are for example corn, wheat, rice, barley, sorghum, musa, sugarcane, miscanthus and brachypodium, especially preferred monocotyledonous plants are corn, wheat and rice, most preferred is wheat. Preferred dicotyledonous plants are for example soy, rape seed, canola, linseed, cotton, potato, sugar beet, tagetes and *Arabidopsis*, especially preferred dicotyledonous plants are soy, rape seed, canola and potato.

In one embodiment of the method of the invention the one or more NEENA molecule or NEENA sequence is integrated into the genome of a plant or part thereof by applying genome editing technologies.

In a further embodiment of the method of the invention the genome editing technology comprises the introduction of single or double strand breaks at the position the NEENA molecule is to be integrated into the genome using nucleic acid guided nucleases, for example AGO, Cas9 or Cas12 nucleases, TALEN, homing endonucleases or Zinc finger proteins and further the introduction of a DNA repair template comprising the NEENA molecule and at its 3' and 5' end sequences essentially identical or essentially complementary to the sequences upstream and/or downstream of the single or double strand break facilitating recombination at the position of the single or double strand break. Preferably, the essentially identical or essentially complementary sequences are each individually at least 1000, at least 500 bases, at least 450 bases, at least 400 bases, at least 350 bases, at least 300 bases, at least 250 bases, at least 200 bases, at least 150 bases, at least 100 bases or at least 50 bases long. Preferably, the identity or complementarity of the sequences is at least 50%, at least 60%, at least 70% at least 75%, at least 80%, at least 85%, at least 90%, at least 95%, at least 96%, at least 97%, at least 98%, at least 98 or at least 99% identical or complementary to the respective genomic region with which they recombine.

In a further embodiment of the method of the invention the genome editing technology comprises introduction of point mutations in the genome of the plant or part thereof thereby introducing the sequence of the NEENA in the plant genome. This can for example be achieved by introducing DNA binding proteins, for example Zinc finger proteins, TALE proteins or a nucleic acid guided nuclease, for example Cas9, Cas12 (Cpf1) or AGO functionally bound to a cytidine deaminase (WO17070633) or adenine deaminase (WO18027078).

In one embodiment of the invention, the methods as defined above are comprising the steps of
 a) introducing one or more NEENA comprising a nucleic acid molecule as defined above in i) to vi) into a plant or part thereof and
 b) integrating said one or more NEENA into the genome of said plant or part thereof whereby said one or more NEENA is functionally linked to an endogenous expressed nucleic acid heterologous to said one or more NEENA and optionally
 c) regenerating a plant or part thereof comprising said one or more NEENA from said transformed cell.

The NEENA may be heterologous to the nucleic acid molecule which is under the control of said promoter to which the NEENA is functionally linked or it may be heterologous to both the promoter and the nucleic acid molecule under the control of said promoter.

The one or more NEENA molecule may be introduced into the plant or part thereof by means of particle bombardment, protoplast electroporation, virus infection, *Agrobacterium* mediated transformation, CRISPR/Cas or any other approach known in the art. The NEENA molecule may be introduced integrated for example into a plasmid or viral DNA or viral RNA or a donorDNA in a CRISPR/Cas approach. The NEENA molecule may also be comprised on a BAC, YAC or artificial chromosome prior to introduction into the plant or part of the plant. It may be also introduced as a linear nucleic acid molecule comprising the NEENA sequence wherein additional sequences may be present adjacent to the NEENA sequence on the nucleic acid molecule. These sequences neighboring the NEENA sequence may be from about 20 bp, for example 20 bp to several hundred base pairs, for example 100 bp or more and may facilitate integration into the genome for example by homologous recombination. Any other method for genome integration may be employed, be it targeted integration approaches, such as homologous recombination or random integration approaches, such as illegitimate recombination.

The endogenous expressed nucleic acid to which the NEENA molecule may be functionally linked may be any nucleic acid, preferably any expressed nucleic acid molecule. The nucleic acid molecule may be a protein coding nucleic acid molecule or a non-coding molecule such as antisense RNA, rRNA, tRNA, miRNA, ta-siRNA, siRNA, dsRNA, snRNA, snoRNA or any other noncoding RNA known in the art.

A further way to perform the methods of the invention may be to
 a) provide an expression construct comprising one or more NEENA comprising a nucleic acid molecule as defined above in i) to vi) functionally linked to a promoter as defined above and to one or more nucleic acid molecule the latter being heterologous to said one or more NEENA and which is under the control of said promoter and b) integrate said expression construct comprising said one or more NEENA into the genome of said plant or part thereof and optionally c) regenerate a plant or part thereof comprising said one or more expression construct from said transformed plant or part thereof.

The NEENA may be heterologous to the nucleic acid molecule which is under the control of said promoter to which the NEENA is functionally linked or it may be heterologous to both the promoter and the nucleic acid molecule under the control of said promoter.

The expression construct may be integrated into the genome of the respective plant with any method known in the art. The integration may be random using methods such as particle bombardment or *Agrobacterium* mediated transformation or CRISPR/Cas applications. In a preferred embodiment, the integration is via targeted integration for example by homologous recombination. The latter method would allow integrating the expression construct comprising a high expression promoter functionally linked to a NEENA into a favorable genome region. Favorable genome regions are for example genome regions known to comprise genes that are highly expressed for example in seeds and hence may increase expression derived from said expression construct compared to a genome region which shows no transcriptional activity.

In another preferred embodiment said one or more NEENA is functionally linked to a promoter close to the transcription start site of said heterologous nucleic acid molecule.

Close to the transcription start site as meant herein comprises functionally linking one or more NEENA to a promoter 5000 bp or less, 4000 bp or less, 3000 or less, 2500 bp or less, preferentially 2000 bp or less, more preferred 1500 bp or less, even more preferred 1000 bp or less and most preferred 500 bp or less away from the transcription start site of said heterologous nucleic acid molecule. It is to be understood that the NEENA may be integrated upstream or downstream in the respective distance from the transcription start site of the respective promoter. Hence, the one or more NEENA may be included in the primary transcript of the respective heterologous nucleic acid under control of the preferably constitutive promoter the one or more NEENA is functionally linked to or it may be integrated in the promoter molecule. If the NEENA is integrated downstream of the transcription start site of the respective promoter, the integration site is preferably in the 5' UTR, the 3' UTR or intron of the heterologous nucleic acid under the control of the promoter, most preferentially it is integrated in the 1$^{st}$ intron of the respective heterologous nucleic acid.

Preferentially the one or more NEENA is integrated in the promoter, the 5' UTR or the 1st intron or the NEENA is replacing a part in the promoter, the 5'UTR or 1$^{st}$ intron.

In another aspect of the invention wherein said one or more NEENA is linked to the 7A trehalose-6-phosphate phosphatase (T6PP) gene (WO/2018/113702, SEQ ID NO. 13), the NEENA may be inserted at about 200 bp, at about 397 bp, at about 676 bp, or at about 1000 bp upstream of the translation start codon. Said one or more NEENA may be inserted into the 7A trehalose-6-phosphate phosphatase (T6PP) gene at a position between 150 and 250 bp, between 350 and 450 bp, between 620 and 720 bp or between 950 and 1000 bp upstream of the translation start codon.

A further embodiment of the invention comprises a recombinant expression construct comprising one or more NEENA comprising a nucleic acid molecule as defined above in i) to vi).

The recombinant expression construct may further comprise one or more promoter to which the one or more NEENA is functionally linked and optionally one or more expressed nucleic acid molecule the latter being heterologous to said one or more NEENA.

The NEENA may be heterologous to the nucleic acid molecule which is under the control of said promoter to which the NEENA is functionally linked or it may be heterologous to both the promoter and the nucleic acid molecule under the control of said promoter.

The expression construct may comprise one or more, for example two or more, for example 5 or more, such as 10 or more combinations of promoters functionally linked to a NEENA and a nucleic acid molecule to be expressed heterologous to the respective NEENA. The expression construct may also comprise further promoters not comprising a NEENA functionally linked to nucleic acid molecules to be expressed homologous or heterologous to the respective promoter.

A recombinant expression vector comprising one or more recombinant expression construct as defined above is another embodiment of the invention. A multitude of expression vectors that may be used in the present invention are known to a skilled person. Methods for introducing such a vector comprising such an expression construct comprising for example a promoter functionally linked to a NEENA and optionally other elements such as a terminator into the genome of a plant and for recovering trans- or cisgenic plants from a transformed cell are also well known in the art. Depending on the method used for the transformation of a plant or part thereof the entire vector might be integrated into the genome of said plant or part thereof or certain components of the vector might be integrated into the genome, such as, for example a T-DNA.

A plant or part thereof comprising one or more heterologous NEENA as defined above in i) to vi) is also enclosed in this invention. A NEENA is to be understood as being heterologous to the plant if it is synthetic, derived from a non-crossable organism (transgenic), a crossable organism (cisgenic) or the same organism but its natural genomic localization is rendered compared to a control plant (cisgenic), for example a wild type plant. It is to be understood, that a rendered genomic localization means the NEENA is located on another chromosome or on the same chromosome but 10 kb or more, for example 10 kb, preferably 5 kb or more, for example 5 kb, more preferably 1000 bp or more, for example 1000 bp, even more preferably 500 bp or more, for example 500 bp, especially preferably 100 bp or more, for example 100 bp, most preferably 10 bp or more, for example 10 bp dislocated from its natural genomic localization in a wild type plant.

A cell or plant or part thereof comprising a recombinant expression vector as defined above or a recombinant expression construct as defined above is a further embodiment of the invention. The cell, plant or part thereof may be selected from the group consisting of bacteria, fungi, yeasts or plant, insect or mammalian cells or plants. Preferably the cells are bacteria, fungi, yeasts or plant cells. Preferred bacteria are Enterobacteria such as *E. coli* and bacteria of the genus *Agrobacteria*, for example *Agrobacterium tumefaciens* and *Agrobacterium rhizogenes*. Preferred plants are monocotyledonous or dicotyledonous plants for example monocotyledonous or dicotyledonous crop plants such as corn, soy, canola, cotton, potato, sugar beet, rice, wheat, sorghum, barley, miscanthus, musa, sugarcane and the like. Preferred crop plants are corn, rice, wheat, soy, canola, cotton or potato. Especially preferred dicotyledonous crop plants are soy, canola, cotton or potato.

Especially preferred monocotyledonous crop plants are corn, wheat and rice. Most preferred is wheat.

A cell culture, seed, parts or propagation material comprising said heterologous NEENA derived from a cell or plant or part thereof as defined above comprising said heterologous NEENA as defined above in i) to vi) or said recombinant expression construct or said recombinant vector as defined above are other embodiments of the invention.

Parts or propagation material as meant herein comprise all tissues and organs, for example leaf, stem and fruit as well as material that is useful for propagation and/or regeneration of plants such as cuttings, scions, layers, branches or shoots comprising the respective NEENA, recombinant expression construct or recombinant vector.

A further embodiment of the invention is the use of the NEENA as defined above in i) to vi) or the recombinant construct or recombinant vector as defined above for enhancing expression in plants or parts thereof.

The application at hand provides gene expression enhancing nucleic acid molecules, constructs comprising one or more promoter functionally linked to one or more NEENA. Additionally, use of such gene expression enhancing nucleic acid molecules and expression constructs, expression vectors, plants or parts thereof and cells comprising such heterologous gene expression enhancing nucleic acid molecules are provided.

A use of a cell culture, seed, parts or propagation material, comprising the heterologous NEENA, derived from a cell or plant or part thereof as defined above for the production of foodstuffs, animal feeds, seeds, pharmaceuticals or fine chemicals is also enclosed in this invention.

Definitions

Abbreviations: NEENA—nucleic acid expression enhancing nucleic acid, GFP—green fluorescence protein, GUS—beta-Glucuronidase, BAP—6-benzylaminopurine; 2,4-D—2,4-dichlorophenoxyacetic acid; MS—Murashige and Skoog medium; NAA—1-naphtaleneacetic acid; MES, 2-(N-morpholino-ethanesulfonic acid, IAA indole acetic acid; Kan: Kanamycin sulfate; GA3—Gibberellic acid; Timentin™: ticarcillin disodium/clavulanate potassium, microl: Microliter.

It is to be understood that this invention is not limited to the particular methodology or protocols. It is also to be understood that the terminology used herein is for the purpose of describing particular embodiments only and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. For clarity, certain terms used in the specification are defined and used as follows:

Antiparallel: "Antiparallel" refers herein to two nucleotide sequences paired through hydrogen bonds between complementary base residues with phosphodiester bonds running in the 5'-3' direction in one nucleotide sequence and in the 3'-5' direction in the other nucleotide sequence.

Antisense: The term "antisense" refers to a nucleotide sequence that is inverted relative to its normal orientation for transcription or function and so expresses an RNA transcript that is complementary to a target gene mRNA molecule expressed within the host cell (e.g., it can hybridize to the target gene mRNA molecule or single stranded genomic DNA through Watson-Crick base pairing) or that is complementary to a target DNA molecule such as, for example genomic DNA present in the host cell.

Coding region: As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine and on the 3'-side by one of the three triplets which specify stop codons (i.e., TAA, TAG, TGA). In addition to containing introns, genomic forms of a gene may also include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

Complementary: "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases are not matched according to the base pairing rules.

"Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands. A "complement" of a nucleic acid sequence as used herein refers to a nucleotide sequence whose nucleic acid molecules show total complementarity to the nucleic acid molecules of the nucleic acid sequence.

Double-stranded RNA: A "double-stranded RNA" molecule or "dsRNA" molecule comprises a sense RNA fragment of a nucleotide sequence and an antisense RNA fragment of the nucleotide sequence, which both comprise nucleotide sequences complementary to one another, thereby allowing the sense and antisense RNA fragments to pair and form a double-stranded RNA molecule.

Endogenous: An "endogenous" nucleotide sequence refers to a nucleotide sequence, which is present in the genome of the untransformed or wild type plant cell.

Enhanced expression: "enhance" or "increase" the expression of a nucleic acid molecule in a plant cell are used equivalently herein and mean that the level of expression of the nucleic acid molecule in a plant, part of a plant or plant cell after applying a method of the present invention is higher than its expression in the plant, part of the plant or plant cell before applying the method, or compared to a reference plant lacking a recombinant nucleic acid molecule of the invention. For example, the reference plant is comprising the same construct which is only lacking the respective NEENA. The term "enhanced" or "increased" as used herein are synonymous and means herein higher, preferably significantly higher expression of the nucleic acid molecule to be expressed. As used herein, an "enhancement" or "increase" of the level of an agent such as a protein, mRNA or RNA means that the level is increased relative to a substantially identical plant, part of a plant or plant cell grown under substantially identical conditions, lacking a recombinant nucleic acid molecule of the invention, for example lacking the NEENA molecule, the recombinant construct or recombinant vector of the invention. As used herein, "enhancement" or "increase" of the level of an agent, such as for example a preRNA, mRNA, rRNA, tRNA, snoRNA, snRNA expressed by the target gene and/or of the protein product encoded by it, means that the level is increased 50% or more, for example 100% or more, preferably 200% or more, more preferably 5 fold or more, even more preferably 10 fold or more, most preferably 20 fold or more for example 50 fold relative to a cell or organism lacking a recombinant nucleic acid molecule of the invention. The enhancement or increase can be determined by methods with which the skilled worker is familiar. Thus, the enhancement or increase of the nucleic acid or protein quantity can be determined for example by an immunological detection of the protein. Moreover, techniques such as protein assay, fluorescence, Northern hybridization, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS) can be employed to measure a specific protein or RNA in a plant or plant cell. Depending on the type of the induced protein product, its activity or the effect on the phenotype of the organism or the cell may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry O H et al. (1951) J Biol Chem 193:265-275) or measuring the absorption of CBB G-250 (Bradford M M (1976) Analyt Biochem 72:248-254). As one example for quantifying the activity of a protein, the detection of luciferase activity is described in the Examples below.

Expression: "Expression" refers to the biosynthesis of a gene product, preferably to the transcription and/or translation of a nucleotide sequence, for example an endogenous gene or a heterologous gene, in a cell. For example, in the case of a structural gene, expression involves transcription of the structural gene into mRNA and—optionally—the subsequent translation of mRNA into one or more polypeptides. In other cases, expression may refer only to the transcription of the DNA harboring an RNA molecule.

Expression construct: "Expression construct" as used herein mean a DNA sequence capable of directing expression of a particular nucleotide sequence in an appropriate part of a plant or plant cell, comprising a promoter functional in said part of a plant or plant cell into which it will be introduced, operatively linked to the nucleotide sequence of interest which is—optionally—operatively linked to termination signals. If translation is required, it also typically comprises sequences required for proper translation of the nucleotide sequence. The coding region may code for a protein of interest but may also code for a functional RNA of interest, for example RNAa, siRNA, snoRNA, snRNA, microRNA, ta-siRNA or any other noncoding regulatory RNA, in the sense or antisense direction. The expression construct comprising the nucleotide sequence of interest may be chimeric, meaning that one or more of its components is heterologous with respect to one or more of its other components. The expression construct may also be one, which is naturally occurring but has been obtained in a recombinant form useful for heterologous expression. Typically, however, the expression construct is heterologous with respect to the host, i.e., the particular DNA sequence of the expression construct does not occur naturally in the host cell and must have been introduced into the host cell or an ancestor of the host cell by a transformation event. The expression of the nucleotide sequence in the expression construct may be under the control of a constitutive promoter or of an inducible promoter, which initiates transcription only when the host cell is exposed to some particular external stimulus. In the case of a plant, the promoter can also be specific to a particular tissue or organ or stage of development.

Foreign: The term "foreign" refers to any nucleic acid molecule (e.g., gene sequence) which is introduced into the genome of a cell by experimental manipulations and originates from a species which is non-crossable with the species from which said cell originates. It may include sequences which contain some modification (e.g., a point mutation, the presence of a selectable marker gene, etc.) and is therefore distinct relative to the naturally-occurring sequence.

Functional linkage: The term "functional linkage" or "functionally linked" is to be understood as meaning, for example, the sequential arrangement of a regulatory element (e.g. a promoter) with a nucleic acid sequence to be expressed and, if appropriate, further regulatory elements (such as e.g., a terminator or a NEENA) in such a way that each of the regulatory elements can fulfill its intended function to allow, modify, facilitate or otherwise influence expression of said nucleic acid sequence. As a synonym the wording "operable linkage" or "operably linked" may be used. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly is preferably less than 200 base pairs, especially preferably less than 100 base pairs, very especially preferably less than 50 base pairs. In a preferred embodiment, the nucleic acid sequence to be transcribed is located behind the promoter in such a way that the transcription start is identical with the desired beginning of the chimeric RNA of the invention. Functional linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (N.Y.); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of a regulatory region for example a promoter and nucleic acid sequence to be expressed, can exist in a vector-integrated form and be inserted into a plant genome, for example by transformation.

Gene: The term "gene" refers to a region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF) as well as, where applicable, intervening sequences (i.e., introns) between individual coding regions (i.e., exons). The term "structural gene" as used herein is intended to mean a DNA sequence that is transcribed into mRNA which is then translated into a sequence of amino acids characteristic of a specific polypeptide.

Genome and genomic DNA: The terms "genome" or "genomic DNA" is referring to the heritable genetic information of a host organism. Said genomic DNA comprises the DNA of the nucleus (also referred to as chromosomal DNA) but also the DNA of the plastids (e.g., chloroplasts) and other cellular organelles (e.g., mitochondria). Preferably the terms genome or genomic DNA is referring to the chromosomal DNA of the nucleus.

Heterologous: The term "heterologous" with respect to a nucleic acid molecule or DNA refers to a nucleic acid molecule which is operably linked to, or is manipulated to become operably linked to, a second nucleic acid molecule, e.g. a promoter to which it is not operably linked in nature, e.g. in the genome of a WT plant, or to which it is operably linked at a different location or position in nature, e.g. in the genome of said WT plant.

Preferably the term "heterologous" with respect to a nucleic acid molecule or DNA, e.g. a NEENA refers to a nucleic acid molecule which is operably linked to, or is manipulated to become operably linked to, a second nucleic acid molecule, e.g. a promoter to which it is not operably linked in nature.

A heterologous expression construct comprising a nucleic acid molecule and one or more regulatory nucleic acid molecule (such as a promoter or a transcription termination signal) linked thereto for example is a constructs originating by experimental manipulations in which either a) said nucleic acid molecule, or b) said regulatory nucleic acid molecule or c) both (i.e. (a) and (b)) is not located in its natural (native) genetic environment or has been modified by experimental manipulations, an example of a modification being a substitution, addition, deletion, inversion or insertion of one or more nucleotide residues. Natural genetic environment refers to the natural chromosomal locus in the organism of origin, or to the presence in a genomic library. In the case of a genomic library, the natural genetic environment of the sequence of the nucleic acid molecule is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene— becomes a heterologous expression construct when it is modified by nonnatural, synthetic "artificial" methods such as, for example, induced mutagenization. Such methods have been described (U.S. Pat. No. 5,565,350; WO 00/15815). For example, a protein encoding nucleic acid molecule operably linked to a promoter, which is not the native promoter of this molecule, is considered to be heterologous with respect to the promoter. Heterologous DNA may not be endogenous to or not naturally associated with the cell into which it is introduced, but has been obtained from another cell or has been synthesized. Heterologous DNA also includes an endogenous DNA sequence, which contains some modification, non-naturally occurring, multiple copies of an endogenous DNA sequence, or a DNA sequence which is not naturally associated with another DNA sequence physically linked thereto. Generally, although not necessarily, heterologous DNA encodes RNA or proteins that are not normally produced by the cell into which it is expressed.

High expression promoter: A "high expression promoter" as used herein means a promoter causing expression in a plant or part thereof wherein the accumulation or rate of synthesis of RNA or stability of RNA derived from the nucleic acid molecule under the control of the respective promoter is higher, preferably significantly higher than the expression caused by the promoter lacking the NEENA of the invention. Preferably the amount of RNA and/or the rate of RNA synthesis and/or stability of RNA is increased 50% or more, for example 100% or more, preferably 200% or more, more preferably 5-fold or more, even more preferably 10-fold or more, most preferably 20 fold or more for example 50-fold relative to a promoter lacking a NEENA of the invention.

Hybridization: The term "hybridization" as defined herein is a process wherein substantially complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitrocellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point (Tm) for the specific sequence at a defined ionic strength and pH. Medium stringency conditions are when the temperature is 20° C. below Tm, and high stringency conditions are when the temperature is 10° C. below Tm. High stringency hybridisation conditions are typically used for isolating hybridising sequences that have high sequence similarity to the target nucleic acid sequence. However, nucleic acids may deviate in sequence and still encode a substantially identical polypeptide, due to the degeneracy of the genetic code. Therefore, medium stringency hybridisation conditions may sometimes be needed to identify such nucleic acid molecules.

The "Tm" is the temperature under defined ionic strength and pH, at which 50% of the target sequence hybridises to a perfectly matched probe. The Tm is dependent upon the solution conditions and the base composition and length of the probe. For example, longer sequences hybridise specifically at higher temperatures. The maximum rate of hybridisation is obtained from about 16° C. up to 32° C. below Tm. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the Tm decreases about 1° C. per % base mismatch. The Tm may be calculated using the following equations, depending on the types of hybrids:

DNA-DNA Hybrids (Meinkoth and Wahl, Anal. Biochem., 138: 267-284, 1984):

$$Tm=81.5° C.+16.6\times \log [Na+]a+0.41\times \%[G/Cb]-500\times [Lc]-1-0.61\times\% \text{ formamide}$$

DNA-RNA or RNA-RNA Hybrids:

$$Tm=79.8+18.5(\log 10[Na+]a)+0.58(\% G/Cb)+11.8(\% G/Cb)2-820/Lc$$

Oligo-DNA or Oligo-RNAd Hybrids:
For <20 nucleotides: Tm=2(In)
For 20-35 nucleotides: Tm=22+1.46(In)
a or for other monovalent cation, but only accurate in the 0.01-0.4 M range.
b only accurate for % GC in the 30% to 75% range.
c L=length of duplex in base pairs.
d Oligo, oligonucleotide; In, effective length of primer=2×(no. of G/C)+(no. of A/T).

Non-specific binding may be controlled using any one of a number of known techniques such as, for example, blocking the membrane with protein containing solutions, additions of heterologous RNA, DNA, and SDS to the hybridisation buffer, and treatment with Rnase. For non-related probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid. When nucleic acids of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5×Denhardt's reagent, 0.5-1.0% SDS, 100 µg/ml denatured, fragmented salmon sperm DNA, 0.5% sodium pyrophosphate. Another example of high stringency conditions is hybridisation at 65° C. in 0.1×SSC comprising 0.1 SDS and optionally 5×Denhardt's reagent, 100 µg/ml denatured, fragmented salmon sperm DNA, 0.5% sodium pyrophosphate, followed by the washing at 65° C. in 0.3×SSC. For the purposes of defining the level of stringency, reference can be made to Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

"Identity": "Identity" when used in respect to the comparison of two or more nucleic acid or amino acid molecules means that the sequences of said molecules share a certain degree of sequence similarity, the sequences being partially identical.

Enzyme variants may be defined by their sequence identity when compared to a parent enzyme. Sequence identity usually is provided as "% sequence identity" or "% identity". To determine the percent-identity between two amino acid sequences in a first step a pairwise sequence alignment is generated between those two sequences, wherein the two sequences are aligned over their complete length (i.e., a pairwise global alignment). The alignment is generated with a program implementing the Needleman and Wunsch algorithm (J. Mol. Biol. (1979) 48, p. 443-453), preferably by using the program "NEEDLE" (The European Molecular Biology Open Software Suite (EMBOSS)) with the programs default parameters (gapopen=10.0, gapextend=0.5 and matrix=EBLOSUM62). The preferred alignment for the purpose of this invention is that alignment, from which the highest sequence identity can be determined.

The following example is meant to illustrate two nucleotide sequences, but the same calculations apply to protein sequences:

Seq A: AAGATACTG length: 9 bases
Seq B: GATCTGA length: 7 bases
Hence, the shorter sequence is sequence B.
Producing a pairwise global alignment which is showing both sequences over their complete lengths results in

```
Seq A: AAGATACTG-
       ||| |||
Seq B: --GAT-CTGA
```

The "I" symbol in the alignment indicates identical residues (which means bases for DNA or amino acids for proteins). The number of identical residues is 6.

The "-" symbol in the alignment indicates gaps. The number of gaps introduced by alignment within the Seq B is 1. The number of gaps introduced by alignment at borders of Seq B is 2, and at borders of Seq A is 1.

The alignment length showing the aligned sequences over their complete length is 10.

Producing a pairwise alignment which is showing the shorter sequence over its complete length according to the invention consequently results in:

```
Seq A: GATACTG-
       ||| |||
Seq B: GAT-CTGA
```

Producing a pairwise alignment which is showing sequence A over its complete length according to the invention consequently results in:

```
Seq A: AAGATACTG
       ||| |||
Seq B: --GAT-CTG
```

Producing a pairwise alignment which is showing sequence B over its complete length according to the invention consequently results in:

```
Seq A: GATACTG-
       ||| |||
Seq B: GAT-CTGA
```

The alignment length showing the shorter sequence over its complete length is 8 (one gap is present which is factored in the alignment length of the shorter sequence).

Accordingly, the alignment length showing Seq A over its complete length would be 9 (meaning Seq A is the sequence of the invention).

Accordingly, the alignment length showing Seq B over its complete length would be 8 (meaning Seq B is the sequence of the invention).

After aligning two sequences, in a second step, an identity value is determined from the alignment produced. For purposes of this description, percent identity is calculated by %–identity=(identical residues/length of the alignment region which is showing the respective sequence of this invention over its complete length)*100. Thus, sequence identity in relation to comparison of two amino acid sequences according to this embodiment is calculated by dividing the number of identical residues by the length of the alignment region which is showing the respective sequence of this invention over its complete length. This value is multiplied with 100 to give "%–identity". According to the example provided above, %–identity is: for Seq A being the sequence of the invention (6/9)*100=66.7%; for Seq B being the sequence of the invention (6/8)*100=75%.

Intron: refers to sections of DNA (intervening sequences) within a gene that do not encode part of the protein that the gene produces, and that is spliced out of the mRNA that is transcribed from the gene before it is exported from the cell nucleus. Intron sequence refers to the nucleic acid sequence of an intron. Thus, introns are those regions of DNA sequences that are transcribed along with the coding sequence (exons) but are removed during the formation of mature mRNA. Introns can be positioned within the actual coding region or in either the 5' or 3' untranslated leaders of the pre-mRNA (unspliced mRNA). Introns in the primary transcript are excised and the coding sequences are simultaneously and precisely ligated to form the mature mRNA. The junctions of introns and exons form the splice site. The sequence of an intron begins with GU and ends with AG. Furthermore, in plants, two examples of AU-AC introns have been described: the fourteenth intron of the RecA-like protein gene and the seventh intron of the G5 gene from *Arabidopsis thaliana* are AT-AC introns. Pre-mRNAs containing introns have three short sequences that are—beside other sequences—essential for the intron to be accurately spliced. These sequences are the 5' splice-site, the 3' splice-site, and the branchpoint. mRNA splicing is the removal of intervening sequences (introns) present in primary mRNA transcripts and joining or ligation of exon sequences. This is also known as cis-splicing which joins two exons on the same RNA with the removal of the intervening sequence (intron). The functional elements of an intron is comprising sequences that are recognized and bound by the specific protein components of the spliceosome (e.g. splicing consensus sequences at the ends of introns). The interaction of the functional elements with the spliceosome results in the removal of the intron sequence from the premature mRNA and the rejoining of the exon sequences. Introns have three short sequences that are essential—although not sufficient—for the intron to be accurately spliced. These sequences are the 5' splice site, the 3' splice site and the branch point. The branchpoint sequence is important in splicing and splice-site selection in plants. The branchpoint sequence is usually located 10-60 nucleotides upstream of the 3' splice site.

Isogenic: organisms (e.g., plants), which are genetically identical, except that they may differ by the presence or absence of a heterologous DNA sequence.

Isolated: The term "isolated" as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic or cisgenic host cell. For example, a naturally occurring polynucleotide or polypeptide present in a living plant is not isolated, but the same polynucleotide or polypeptide, separated from some or all of the coexisting materials in the natural system, is isolated. Such polynucleotides can be part of a vector and/or such polynucleotides or polypeptides could be part of a composition and would be isolated in that such a vector or composition is not part of its original environment. Preferably, the term "isolated" when used in relation to a nucleic acid molecule, as in "an isolated nucleic acid sequence" refers to a nucleic acid sequence that is identified and separated from at least one contaminant nucleic acid molecule with which it is ordinarily associated in its natural source. Isolated nucleic acid molecule is nucleic acid molecule present in a form or setting that is different from that in which it is found in nature. In contrast, non-isolated nucleic acid molecules are nucleic acid molecules such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, an isolated nucleic acid sequence comprising for example SEQ ID NO: 1 includes, by way of example, such nucleic acid sequences in cells which ordinarily contain SEQ ID NO:1 where the nucleic acid sequence is in a chromosomal or extrachromosomal location different from that of natural cells or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

Minimal Promoter: promoter elements, particularly a TATA element, that are inactive or that have greatly reduced promoter activity in the absence of upstream activation. In the presence of a suitable transcription factor, the minimal promoter functions to permit transcription.

NEENA: see "Nucleic acid expression enhancing nucleic acid".

Non-coding: The term "non-coding" refers to sequences of nucleic acid molecules that do not encode part or all of an expressed protein. Non-coding sequences include but are not limited to introns, enhancers, promoter regions, 3' untranslated regions, and 5' untranslated regions.

Nucleic acid expression enhancing nucleic acid (NEENA): The term "nucleic acid expression enhancing nucleic acid" refers to a sequence and/or a nucleic acid molecule of a specific sequence having the intrinsic property to enhance expression of a nucleic acid under the control of a promoter to which the NEENA is functionally linked. Unlike promoter sequences, the NEENA as such is not able to drive expression. In order to fulfill the function of enhancing expression of a nucleic acid molecule functionally linked to the NEENA, the NEENA itself has to be functionally linked to a promoter. In distinction to enhancer sequences known in the art, the NEENA is acting in cis but not in trans and has to be located close to the transcription start site of the nucleic acid to be expressed.

Nucleic acids and nucleotides: The terms "Nucleic Acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used interchangeably herein with "gene", "cDNA, "mRNA", "oligonucleotide," and "polynucleotide". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. Short hairpin RNAs (shRNAs) also can comprise non-natural elements such as non-natural bases, e.g., ionosin and xanthine, non-natural sugars, e.g., 2'-methoxy ribose, or non-natural phosphodiester linkages, e.g., methylphosphonates, phosphorothioates and peptides.

Nucleic acid sequence: The phrase "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid, which is transcribed and translated in a sequence-specific manner to produce into a particular polypeptide or protein when placed under the control of appropriate regulatory sequences. The coding region is said to encode such a polypeptide or protein.

Oligonucleotide: The term "oligonucleotide" refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

Overhang: An "overhang" is a relatively short single-stranded nucleotide sequence on the 5'- or 3'-hydroxyl end of a double-stranded oligonucleotide molecule (also referred to as an "extension," "protruding end," or "sticky end").

Plant: is generally understood as meaning any eukaryotic single- or multi-celled organism or a cell, tissue, organ, part or propagation material (such as seeds or fruit) of same which is capable of photosynthesis. Included for the purpose of the invention are all genera and species of higher and lower plants of the Plant Kingdom. Annual, perennial, monocotyledonous and dicotyledonous plants are preferred. The term includes the mature plants, seed, shoots and seedlings and their derived parts, propagation material (such as seeds or microspores), plant organs, tissue, protoplasts, callus and other cultures, for example cell cultures, and any other type of plant cell grouping to give functional or structural units. Mature plants refer to plants at any desired developmental stage beyond that of the seedling. Seedling refers to a young immature plant at an early developmental stage. Annual, biennial, monocotyledonous and dicotyledonous plants are preferred host organisms for the generation of transgenic or cisgenic plants. The expression of genes is furthermore advantageous in all ornamental plants, useful or ornamental trees, flowers, cut flowers, shrubs or lawns.

Plants which may be mentioned by way of example but not by limitation are angiosperms, bryophytes such as, for example, Hepaticae (liverworts) and Musci (mosses); Pteridophytes such as ferns, horsetail and club mosses; gymnosperms such as conifers, cycads, ginkgo and Gnetatae; algae such as Chlorophyceae, Phaeophyceae, Rhodophyceae, Myxophyceae, Xanthophyceae, Bacillariophyceae (diatoms), and Euglenophyceae. Preferred are plants which are used for food or feed purpose such as the families of the Leguminosae such as pea, alfalfa and soya; Gramineae such as rice, maize, wheat, barley, sorghum, millet, rye, triticale, or oats; the family of the Umbelliferae, especially the genus *Daucus*, very especially the species *carota* (carrot) and *Apium*, very especially the species *Graveolens dulce* (celery) and many others; the family of the Solanaceae, especially the genus *Lycopersicon*, very especially the species *esculentum* (tomato) and the genus *Solanum*, very especially the species *tuberosum* (potato) and *melongena* (egg plant), and many others (such as tobacco); and the genus *Capsicum*, very especially the species *annuum* (peppers) and many others; the family of the Leguminosae, especially the genus *Glycine*, very especially the species *max* (soybean), alfalfa, pea, lucerne, beans or peanut and many others; and the family of the Cruciferae (Brassicacae), especially the genus *Brassica*, very especially the species *napus* (oil seed rape), *campestris* (beet), *oleracea* cv Tastie (cabbage), *oleracea* cv Snowball Y (cauliflower) and *oleracea* cv Emperor (broccoli); and of the genus *Arabidopsis*, very especially the species *thaliana* and many others; the family of the Compositae, especially the genus *Lactuca*, very especially the species *sativa* (lettuce) and many others; the family of the Asteraceae such as sunflower, Tagetes, lettuce or Calendula and many other; the family of the Cucurbitaceae such as melon, pumpkin/squash or zucchini, and linseed. Further preferred are cotton, sugar cane, hemp, flax, chillies, and the various tree, nut and wine species.

Polypeptide: The terms "polypeptide", "peptide", "oligopeptide", "polypeptide", "gene product", "expression product" and "protein" are used interchangeably herein to refer to a polymer or oligomer of consecutive amino acid residues.

Pre-protein: Protein, which is normally targeted to a cellular organelle, such as a chloroplast, and still comprising its transit peptide.

Primary transcript: The term "primary transcript" as used herein refers to a premature RNA transcript of a gene. A "primary transcript" for example still comprises introns and/or is not yet comprising a polyA tail or a cap structure and/or is missing other modifications necessary for its correct function as transcript such as for example trimming or editing.

Promoter: The terms "promoter", or "promoter sequence" are equivalents and as used herein, refer to a DNA sequence which when ligated to a nucleotide sequence of interest is capable of controlling the transcription of the nucleotide sequence of interest into RNA. Such promoters can for example be found in the following public databases world wide web at grassius.org/grasspromdb.html, world wide web at mendel.cs.rhul.ac.uk/mendel.php?topic=plantprom, world wide web at ppdb.gene.nagoya-u.ac.jp/cgi-bin/index-.cgi. Promoters listed there may be addressed with the methods of the invention and are herewith included by reference. A promoter is located 5' (i.e., upstream), proximal to the transcriptional start site of a nucleotide sequence of interest whose transcription into mRNA it controls, and provides a site for specific binding by RNA polymerase and other transcription fac-tors for initiation of transcription. Said promoter comprises for example the at least 10 kb, for example 5 kb or 2 kb proximal to the transcription start site. It may also comprise the at least 1500 bp proximal to the transcriptional start site, preferably the at least 1000 bp, more preferably the at least 500 bp, even more preferably the at least 400 bp, the at least 300 bp, the at least 200 bp or the at least 100 bp. In a further preferred embodiment, the promoter comprises the at least 50 bp proximal to the transcription start site, for example, at least 25 bp. The promoter does not comprise exon and/or intron regions or 5' untranslated regions. The promoter may for example be heterologous or homologous to the respective plant. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host cells (e.g., plants or plant pathogens like plant viruses). A plant specific promoter is a promoter suitable for regulating expression in a plant. It may be derived from a plant but also from plant pathogens or it might be a synthetic promoter designed by man. If a promoter is an inducible promoter, then the rate of transcription increases in response to an inducing agent. Also, the promoter may be regulated in a tissue-specific or tissue preferred manner such that it is only or predominantly active in transcribing the associated coding region in a specific tissue type(s) such as leaves, roots or meristem. The term "tissue specific" as it applies to a promoter refers to a promoter that is capable of directing selective expression of a nucleotide sequence of interest to a specific type of tissue (e.g., petals) in the relative absence of expression of the same nucleotide sequence of interest in a different type of tissue (e.g., roots). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter, which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., GUS activity staining, GFP protein or immunohistochemical staining. The term "constitutive" when made in reference to a promoter or the expression derived from a promoter means that the promoter is capable of directing transcription of an operably linked nucleic acid molecule in the absence of a stimulus (e.g., heat shock, chemicals, light, etc.) in the majority of plant tissues and cells throughout substantially the entire lifespan of a plant or part of a plant. Typically, constitutive promoters are capable of directing expression of a gene in substantially any cell and any tissue.

Promoter specificity: The term "specificity" when referring to a promoter means the pattern of expression conferred by the respective promoter. The specificity describes the tissues and/or developmental status of a plant or part thereof, in which the promoter is conferring expression of the nucleic acid molecule under the control of the respective promoter. Specificity of a promoter may also comprise the environmental conditions, under which the promoter may be activated or down-regulated such as induction or repression by biological or environmental stresses such as cold, drought, wounding or infection.

Purified: As used herein, the term "purified" refers to molecules, either nucleic or amino acid sequences that are removed from their natural environment, isolated or separated. "Substantially purified" molecules are at least 60% free, preferably at least 75% free, and more preferably at least 90% free from other components with which they are naturally associated. A purified nucleic acid sequence may be an isolated nucleic acid sequence.

Recombinant: The term "recombinant" with respect to nucleic acid molecules refers to nucleic acid molecules produced by recombinant DNA techniques. Recombinant nucleic acid molecules may also comprise molecules, which as such does not exist in nature but are modified, changed, mutated or otherwise manipulated by man. Preferably, a "recombinant nucleic acid molecule" is a non-naturally occurring nucleic acid molecule that differs in sequence from a naturally occurring nucleic acid molecule by at least one nucleic acid. A "recombinant nucleic acid molecule" may also comprise a "recombinant construct" which comprises, preferably operably linked, a sequence of nucleic acid molecules not naturally occurring in that order. Preferred methods for producing said recombinant nucleic acid molecule may comprise cloning techniques, directed or non-directed mutagenesis, synthesis or recombination techniques.

Sense: The term "sense" is understood to mean a nucleic acid molecule having a sequence which is complementary or identical to a target sequence, for example a sequence which binds to a protein transcription factor and which is involved in the expression of a given gene. According to a preferred embodiment, the nucleic acid molecule comprises a gene of interest and elements allowing the expression of the said gene of interest.

Significant increase or decrease: An increase or decrease, for example in enzymatic activity or in gene expression, that is larger than the margin of error inherent in the measurement technique, preferably an increase or decrease by about 2-fold or greater of the activity of the control enzyme or expression in the control cell, more preferably an increase or decrease by about 5-fold or greater, and most preferably an increase or decrease by about 10-fold or greater.

Small nucleic acid molecules: "small nucleic acid molecules" are understood as molecules consisting of nucleic acids or derivatives thereof such as RNA or DNA. They may be double-stranded or single-stranded and are between about 15 and about 30 bp, for example between 15 and 30 bp, more preferred between about 19 and about 26 bp, for example between 19 and 26 bp, even more preferred between about 20 and about 25 bp for example between 20 and 25 bp. In a especially preferred embodiment the oligonucleotides are between about 21 and about 24 bp, for example between 21 and 24 bp. In a most preferred embodiment, the small nucleic acid molecules are about 21 bp and about 24 bp, for example 21 bp and 24 bp.

Substantially complementary: In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the latter being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

Transgene: The term "transgene" as used herein refers to any nucleic acid sequence, which is introduced into the genome of a cell by experimental manipulations. A transgene is an a "heterologous DNA sequence" originating from a non-crossable species.

Cisgene: The term "cisgene" as used herein refers to any nucleic acid sequence, which is introduced into the genome of a cell by experimental manipulations. A cisgene may be an "endogenous DNA sequence," or a "heterologous DNA sequence" originating from a crossable, sexually compatible species.

The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

Transgenic: The term transgenic when referring to an organism means transformed, preferably stably transformed, with a recombinant DNA molecule that preferably comprises a suitable promoter operatively linked to a DNA sequence of interest, wherein said recombinant DNA molecule is a transgene.

Cisgenic: The term cisgenic when referring to an organism means transformed, preferably stably transformed, or genome-edited with a cisgene.

Crossable species: The term crossable species means the species within the taxonomic family of the organism. In contrast, the term "non crossable species" means species that are outside of the taxonomic family of the organism.

Vector: As used herein, the term "vector" refers to a nucleic acid molecule capable of transporting another nucleic acid molecule to which it has been linked. One type of vector is a genomic integrated vector, or "integrated vector", which can become integrated into the chromosomal DNA of the host cell. Another type of vector is an episomal vector, i.e., a nucleic acid molecule capable of extra-chromosomal replication. Vectors capable of directing the expression of genes to which they are operatively linked are referred to herein as "expression vectors". In the present specification, "plasmid" and "vector" are used interchangeably unless otherwise clear from the context. Expression vectors designed to produce RNAs as described herein in vitro or in vivo may contain sequences recognized by any RNA polymerase, including mitochondrial RNA polymerase, RNA pol I, RNA pol II, and RNA pol III. These vectors can be used to transcribe the desired RNA molecule in the cell according to this invention. A plant transformation vector is to be understood as a vector suitable in the process of plant transformation.

Wild-type: The term "wild-type", "natural" or "natural origin" means with respect to an organism, polypeptide, or nucleic acid sequence, that said organism is naturally occurring or available in at least one naturally occurring organism which is not changed, mutated, or otherwise manipulated by man.

FIGURES

FIG. 1: Impact of various parts of the CaMV 35S promoter on promoter activity in transiently transformed wheat protoplasts. Horizontal axis legend: 1st row: promoter (35S2: 528-nt long CaMV 35S promoter; −46: minimal 35S promoter); 2nd row: enhancer (35S enhancer coordinates or lambda phage sequence). GUS activities were corrected for variation in protoplast transfection efficiency using the luciferase activities of a co-introduced pKA63 plasmid.

Figure 2:
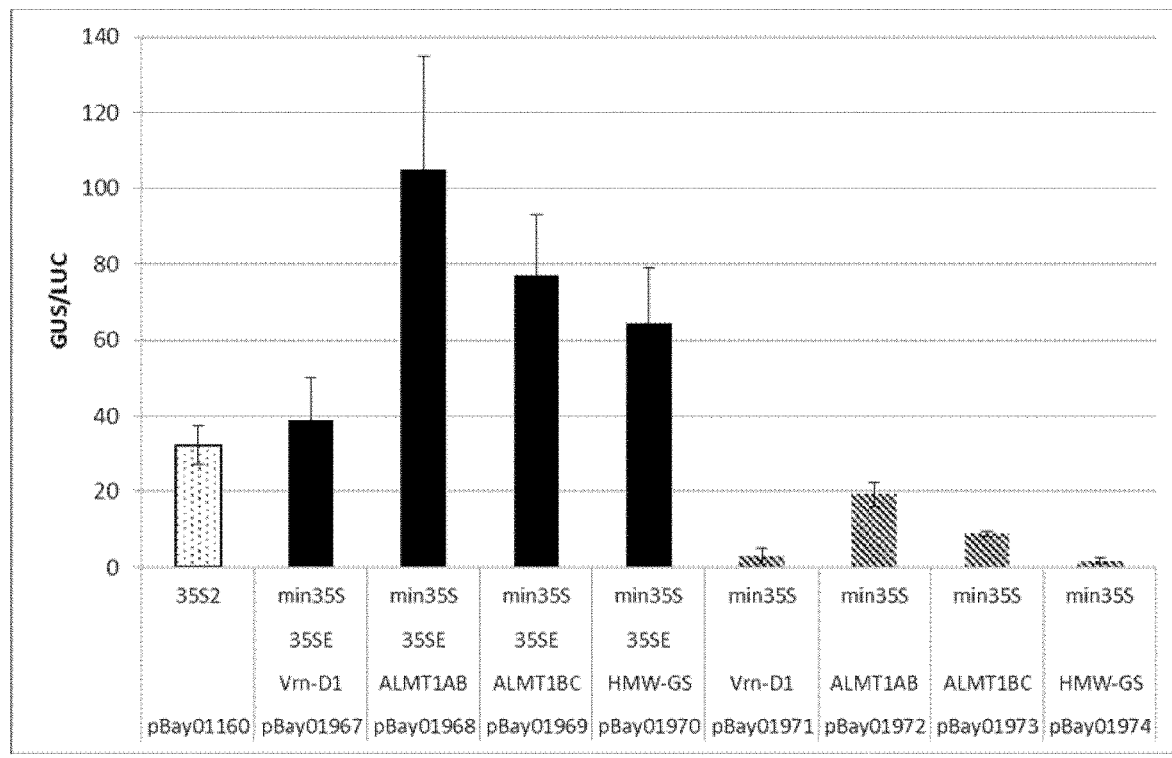

FIG. 2: Impact of candidate wheat enhancers on promoter activity in transiently transformed wheat protoplasts. Horizontal axis legend: 1st row: promoter (35S2: 528-nt long CaMV 35S promoter; min35S: minimal 35S promoter); 2nd row: absence or presence of the −208 to −65 35S enhancer; 3rd row: identity of the candidate wheat enhancer. GUS activities were corrected for variation in protoplast transfection efficiency using the luciferase activities of a co-introduced pKA63 plasmid.

Figure 3:
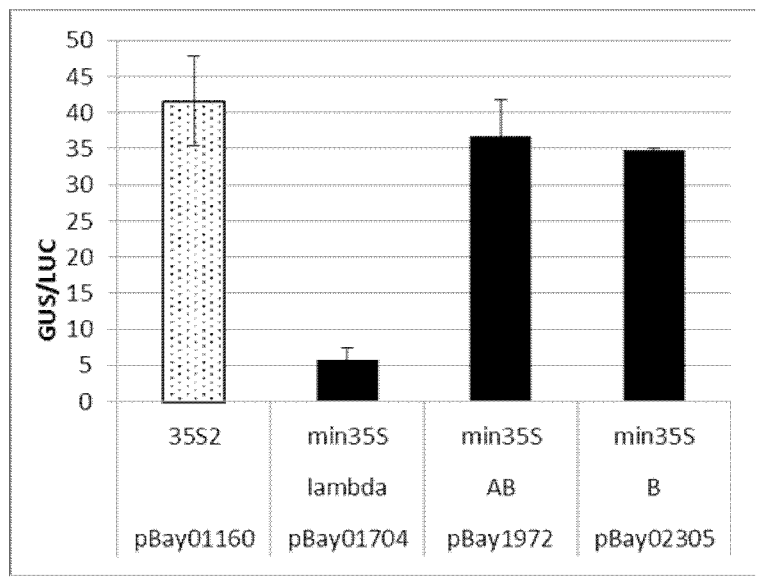

FIG. 3: The ALMT1B fragment is sufficient for full enhancer activity in transiently transformed wheat protoplasts. Horizontal axis legend: 1st row: promoter (35S2: 528-nt long CaMV 35S promoter; min35S: minimal 35S promoter); 2nd row: enhancer sequences. GUS activities were corrected for variation in protoplast transfection efficiency using the luciferase activities of a co-introduced pKA63 plasmid.

Figure 4:
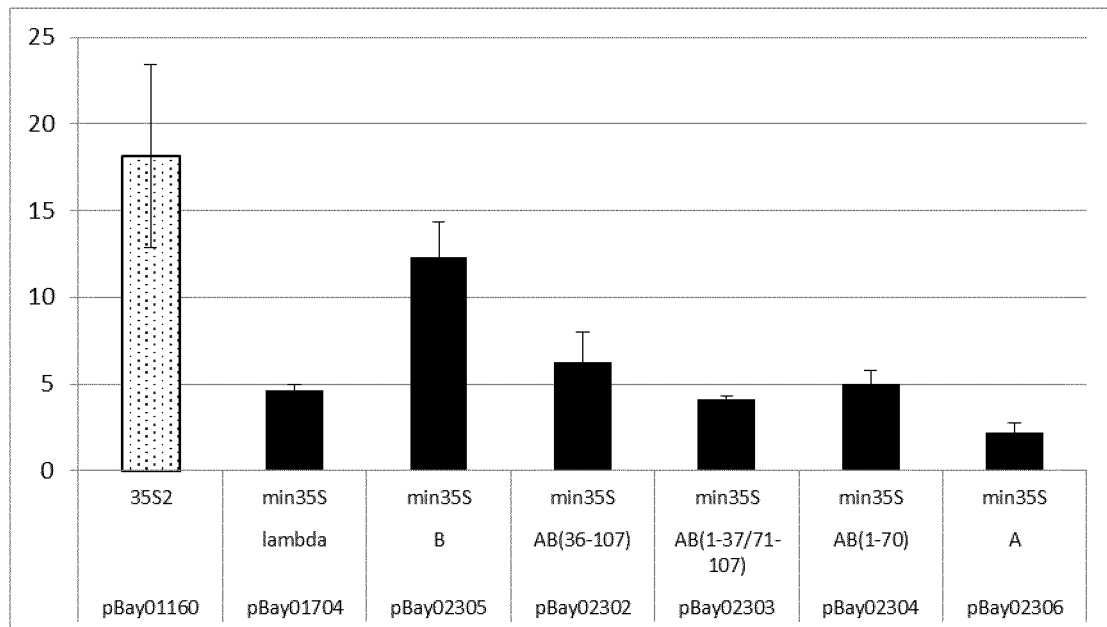

FIG. 4: The ALMT1B fragment is needed for full enhancer activity in transiently transformed wheat protoplasts. Horizontal axis legend: 1st row: promoter (35S2: 528-nt long CaMV 35S promoter; min35S: minimal 35S promoter); 2nd row: enhancer sequences. GUS activities were corrected for variation in protoplast transfection efficiency using the luciferase activities of a co-introduced pKA63 plasmid.

Figure 5:
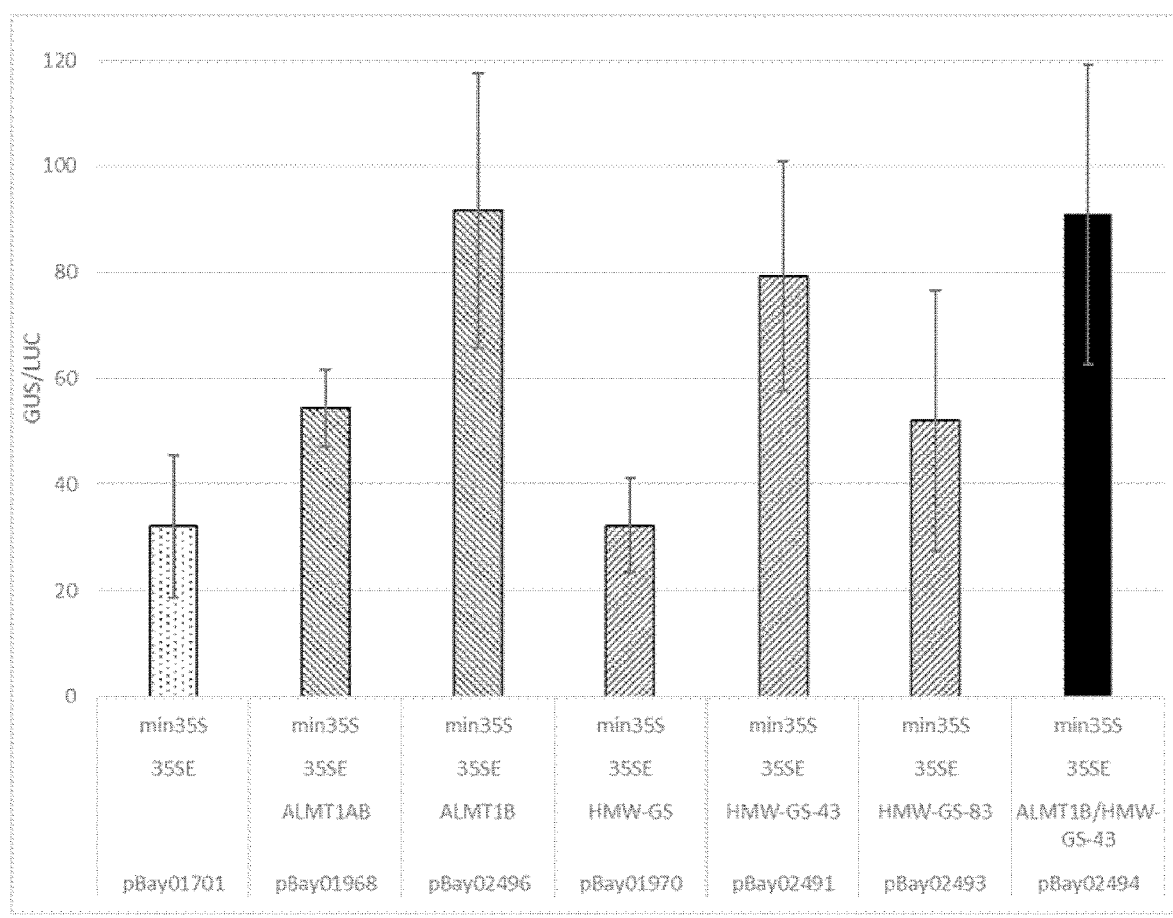

FIG. 5: The ALMT1B and HMW-GS-43 fragments increase activity of a 35S promoter in transiently transformed wheat protoplasts. Horizontal axis legend: 1st row: minimal 35S promoter; 2nd row: −208 to −65 35S enhancer; 3rd row: enhancer sequences. GUS activities were corrected for variation in protoplast transfection efficiency using the luciferase activities of a co-introduced pKA63 plasmid.

Figure 6:
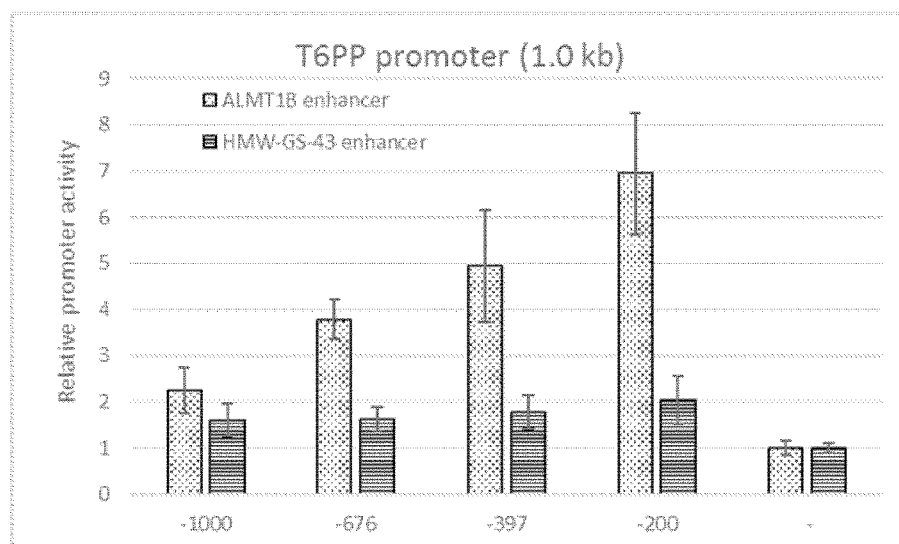

FIG. 6: The ALMT1B and HMW-GS-43 enhancers increase activity of the wheat T6PP promoter in transiently transformed wheat protoplasts. The horizontal axis legend indicates the location of the enhancer insertion sites relative to the translation start site. GUS activities were corrected for variation in protoplast transfection efficiency using the luciferase activities of a co-introduced pKA63 plasmid.

Figure 7:
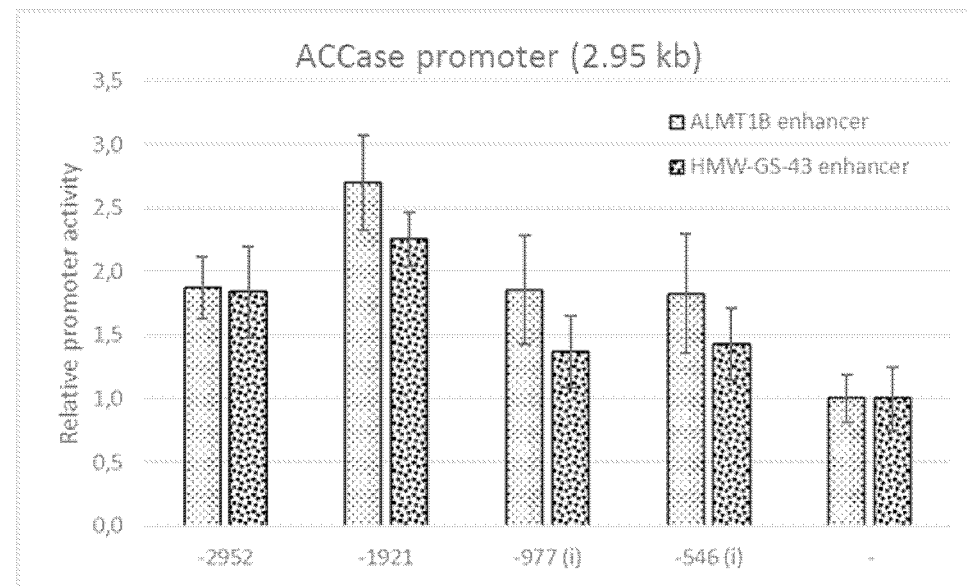

FIG. 7: The ALMT1B and HMW-GS-43 enhancers increase activity of the wheat ACCase promoter in transiently transformed wheat protoplasts. The horizontal axis legend indicates the location of the enhancer insertion sites relative to the translation start site; (i) indicates that the insertion site is located within the first intron. GUS activities were corrected for variation in protoplast transfection efficiency using the luciferase activities of a co-introduced pKA63 plasmid.

Figure 8:
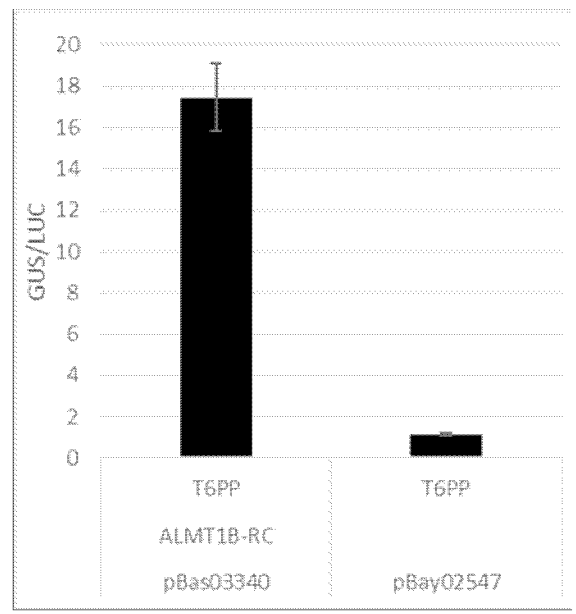

FIG. 8: The reverse complement of the ALMT1B enhancer increases activity of the wheat T6PP promoter in transiently transformed wheat protoplasts. The enhancer was inserted 200 nt upstream of the translation start site. GUS activities were corrected for variation in protoplast transfection efficiency using the luciferase activities of a co-introduced pKA63 plasmid.

Figure 9:
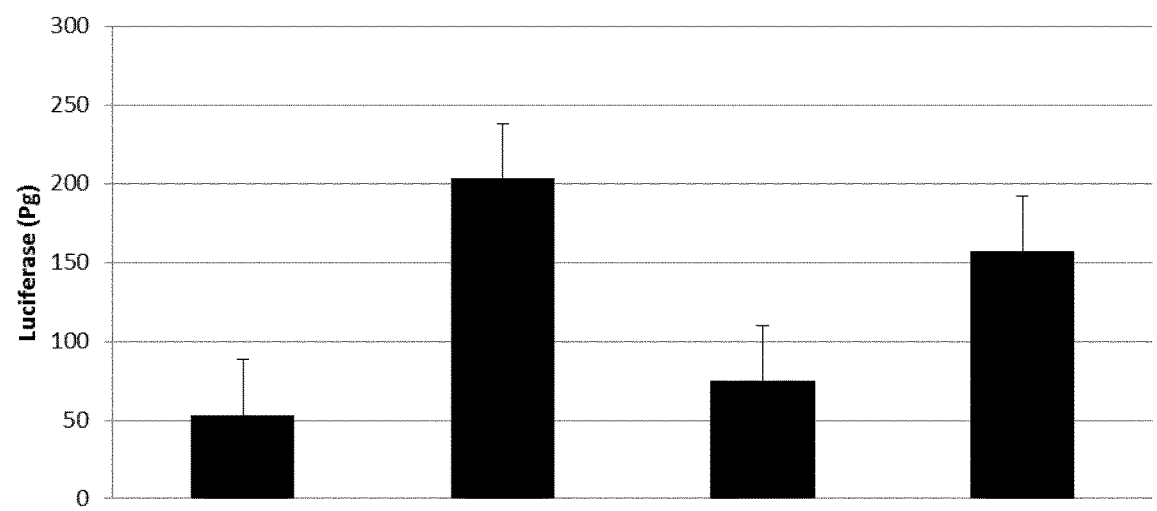

FIG. 9: The HMW-GS-43 enhancer increases promoter activity in infiltrated *Nicotiana benthamiana* leaves.

Figure 10:
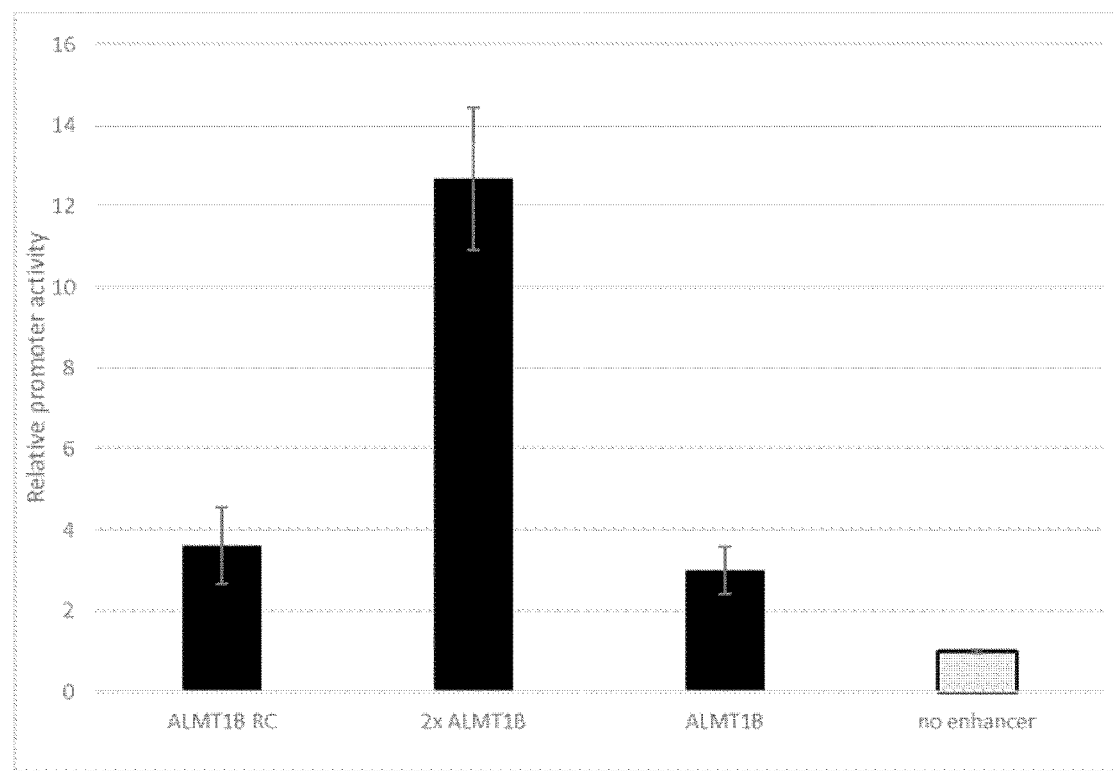

FIG. 10: Impact of the ALMT1B enhancer on activity of the wheat T6PP promoter in transiently transformed wheat protoplasts. The vertical axis shows the relative promoter activity. The horizontal axis legend shows which enhancer fragment was used: the reverse complement (ALMT1B RC), 2 copies (2xALMT1B) or 1 copy (ALMT1B) of SEQ ID 2. GUS activities were corrected for variation in protoplast transfection efficiency using the luciferase activities of a co-introduced pKA63 plasmid. Activity of the promoter without enhancer (none) was set at 1.

Figure 11:
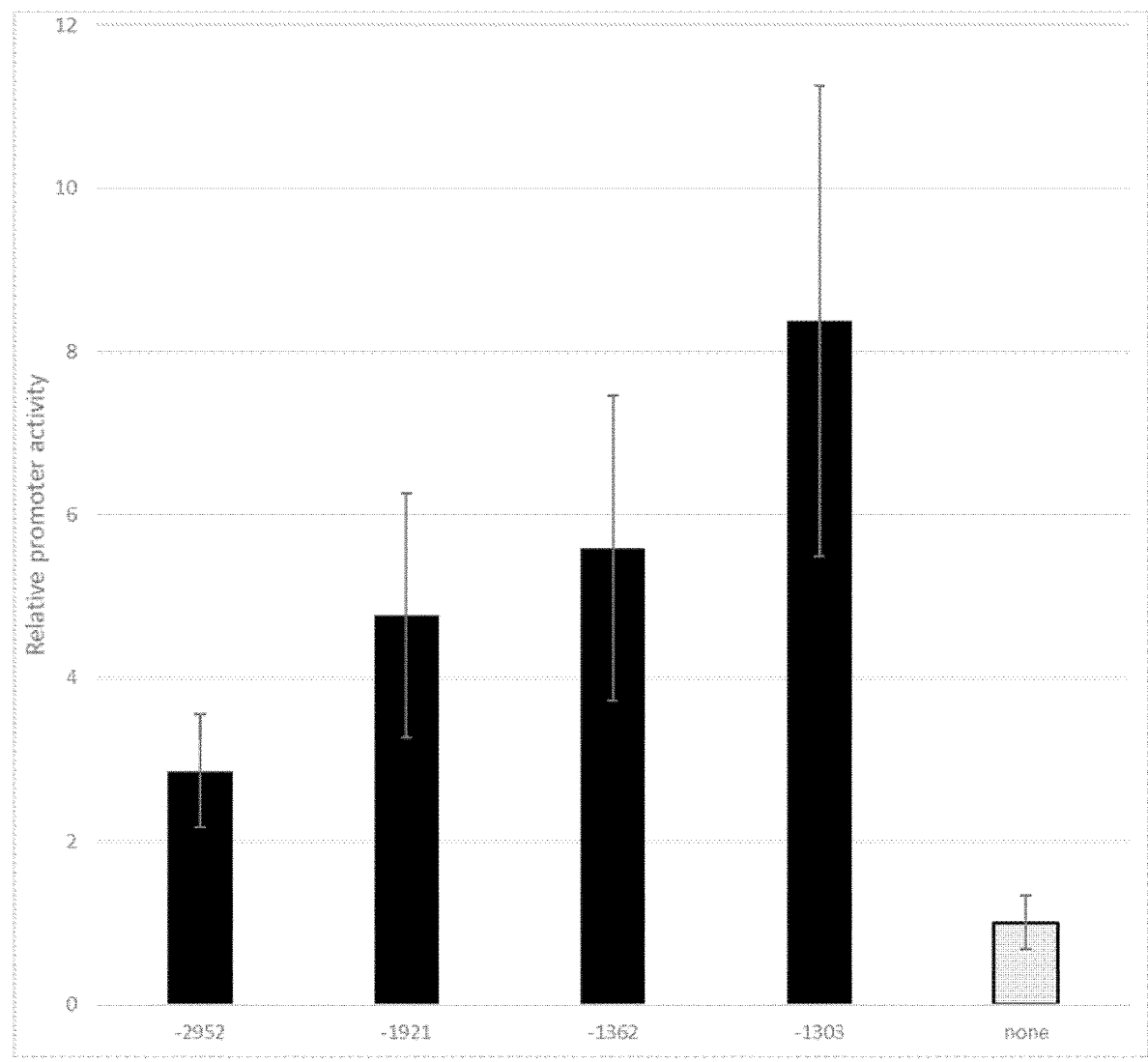

FIG. 11: Impact of the ALMT1B enhancer on activity of the wheat ACCase promoter in transiently transformed wheat protoplasts. The vertical axis shows the relative promoter activity. The horizontal axis legend shows the location of the enhancer insert within the promoter, relative to the translation start site. GUS activities were corrected for variation in protoplast transfection efficiency using the luciferase activities of a co-introduced pKA63 plasmid. Activity of the promoter without enhancer (none) was set at 1.

EXAMPLES

Chemicals and Common Methods

Unless indicated otherwise, cloning procedures carried out for the purposes of the present invention including restriction digest, agarose gel electrophoresis, purification of nucleic acids, Ligation of nucleic acids, transformation, selection and cultivation of bacterial cells were performed as described (Sambrook et al., 1989). Sequence analyses of recombinant DNA were performed with a laser fluorescence DNA sequencer (Applied Biosystems, Foster City, CA, USA) using the Sanger technology (Sanger et al., 1977). Unless described otherwise, chemicals and reagents were obtained from Sigma Aldrich (Sigma Aldrich, St. Louis, USA), from Promega (Madison, WI, USA), Duchefa (Haarlem, The Netherlands) or Invitrogen (Carlsbad, CA, USA). Restriction endonucleases were from New England Biolabs (Ipswich, MA, USA) or Roche Diagnostics GmbH (Penzberg, Germany). Oligonucleotides were synthesized by Eurofins MWG Operon (Ebersberg, Germany).

Example 1: Characterization of Wheat Enhancer Sequences

The impact of three wheat promoter elements on promoter activity was tested by transient expression in wheat mesophyll protoplasts. To identify expression vectors that are suitable for testing enhancer activity, various derivatives of plasmid pBay01160 (SEQ ID NO 6), containing the GUS coding sequence under control of the constitutive CaMV 35S2 promoter (Odell et al (1985). Nature 313(6005), 810-2) and the rice actin-1 intron (McElroy et al (1991). Mol Gen Genet. 231(1), 150-60), were tested in wheat protoplasts. To correct for differences in introduction efficiency, GUS activities of wheat transfected protoplasts were divided by the luciferase activities from a cointroduced control vector (pKA63, SEQ ID NO 9) having the firefly luciferase gene under control of the constitutive maize ubiquitin promoter (Christensen et al (1992). Plant Mol Biol. 18(4), 675-89). Wheat protoplast preparation and PEG transfection of wheat protoplasts was performed according to Shang et al. ((2014), Nature protocols 9(10), 2395-2410).

The vector pBay01697 (SEQ ID NO 7), containing only the minimal 35S promoter (nt −46 to −1) as well as its derivative pBay01704 (SEQ ID NO 10), having a 144-nt lambda phage sequence upstream of the minimal 35S promoter, showed strongly reduced promoter activity compared to the fully active 35S2 promoter of pBay01160 (FIG. 1). Plasmid pBay01701 (SEQ ID NO 8) that has −208 to −65 enhancer sequence of the 35S promoter upstream of the minimal 35S promoter showed promoter activity that is close to the 35S2 promoter of pBay01160 (FIG. 1). This shows that these vectors are suitable for testing enhancer activity in wheat protoplasts. Vector pBay01697 was further used to test the impact of the putative enhancers of SEQ ID NO: 1, 2 and 3 on a promoter that has minimal activity, whereas vector pBay01701 was used to assess the impact on a promoter that has already good activity.

To test the enhancer activity of the wheat promoter elements, the Vrn-D1 175-nt insertion (SEQ ID NO 5) (Zhang et al (2015). Front Plant Sci 6, 470), a 99-nt sequence (SEQ ID NO 11) containing the 43-nt HMW-GS 1Bx7OE promoter insertion (SEQ ID NO 1) (Geng et al (2014). PLoS ONE 9(8), e105363), and sequences corresponding to the ALMT1 AB and BC blocks (SEQ ID NO 2 to 4) (Ryan et al (2010). The Plant Journal 64, 446-455) were inserted upstream of the 35S minimal promoter in pBay01697 as well as upstream of the −208 to −65 35S enhancer in pBay01701. When introduced in wheat protoplasts, the ALMT1 AB enhancer showed the strongest expression increase (FIG. 2). Expression of the minimal 35S promoter was increased up to 60% of the fully active 35S2 promoter whereas in the presence of the 35S enhancer, promoter activity was increased 3.3-fold above that of the 35S2 promoter. The HMW-GS sequence increased expression of the 35S enhancer-containing promoter to a level that was 2-fold above that of the 35S2 promoter whereas no positive effect of this enhancer was observed on the minimal 35S promoter. In contrast, the Vrn-D1 sequence did not show a clear expression increase for both the minimal and the fully active 35S promoter.

Example 2: Deletion Analysis of ALMT1AB Enhancer

To determine the active fragment of the ALMT1AB enhancer, various deletion mutants were tested in combination with the minimal 35S promoter. The B fragment alone showed the same enhancer activity as the complete AB fragment (FIG. 3). In contrast, any 35-bp deletion within the B fragment destroyed enhancer activity whereas the A fragment did not show any enhancer activity (FIG. 4). This maps this enhancer activity to the 107-nt long B fragment.

Example 3: Validation of Active Enhancer Fragments with a Fully Active 35S Promoter Next, the ALMT1B enhancer fragment and various variants of the 1Bx7OEHMW-GS fragment were tested with a fully active 35S promoter (FIG. 5). In this experiment, the ALMT1 B fragment showed a 2.9-fold increase of expression compared to the control plasmid (35S enhancer only), which was clearly higher than that of the AB fragment. From the HMW-GS fragments that were tested, the 43-nt fragment (SEQ ID NO 1) gave the best expression enhancement (2.5-fold). Two copies of the insert did not result in an enhanced activity. Combination of the 1Bx7OEHMW-GS 43-nt fragment with the ALMT1 B fragment did not result in a further expression enhancement.

The 43-nt HMW-GS and 107-nt ALMT1B fragments showed thus the highest enhancer activity and will be tested in combination with wheat promoters.

Example 4: Impact of the HMW-GS-43 and the ALMT1B Enhancers on Wheat Promoter Activity To evaluate the impact of the 1Bx7OEHMW-GS-43 and the ALMT1B enhancers on the activity of endogenous wheat promoters, both fragments were inserted at 4 different sites within 2 wheat promoters:
  a 1-kb promoter fragment of the 7A trehalose-6-phosphate phosphatase (T6PP) gene causing constitutive expression (promoter activity in wheat protoplasts about 25% of that of p35S2) (WO/2018/113702).
  a 2.95-kb promoter fragment of the B genome ACCase gene causing constitutive expression (contains a 1-kb intron; 2 of the insertion sites are within the intron; expression level in wheat protoplasts about 50% of that of p35S2).

The sites of insertion (numbers are relative to the translation start codon) were chosen to not overlap with transcription factor binding sites predicted by MotifLocator (Claeys et al (2012). Bioinformatics 28(14), 1931-1932).

The data in FIGS. 6 and 7 show that each of the enhancers increased activity of both promoters. The level of expression increase depends on the location of the enhancer within the promoter and was the highest with the ALMT1 enhancer. For the T6PP promoter, the increase in promoter activity went up to 7-fold due the ALMT1 enhancer and up to 2-fold for the HMW-GS enhancer. The closer the enhancer was located to the transcription start site (which is located at −126 relative to the translation start codon) the bigger the expression increase.

For the ACCase promoter, only 2 of the insertion sites were located upstream of the transcription initiation site (nt −1240 relative to the translation start codon). From these 2 insertion sites that were located upstream of the transcription start site the expression increase was highest (2.3- to 2.7-fold increase) for the site that was closest to the transcription start site. However, this site is still about 700 nt upstream of the transcription start site. Therefore, 2 additional insertion sites that are upstream of and closer to the TSS of the ACCase promoter were tested. FIG. 11 shows that the biggest expression increase (about 8-fold) happened when the enhancer was inserted only about 70 nt upstream of the TSS. Insertion in the intron gave a lower expression increase compared to insertion upstream of the transcription start site.

These results showed that both the ALMT1B and the HMW-GS-43 enhancer can be used to increase expression from wheat promoters by inserting the enhancer at appropriate locations within the promoter or within the first intron.

Example 5: Enhancer Activity is Independent of the Orientation of the Enhancer Fragment To test whether the enhancer activity is dependent on the orientation of the enhancer versus the promoter, the impact of the reverse complement of the ALMT1B enhancer on activity of the T6PP promoter was determined. Results showed that the complementary sequence of the ALMT1B enhancer increased expression of the T6PP promoter (FIG. 8) and thus had enhancer activity in both orientations.

Example 6: Impact of the HMW-GS-43 Enhancer on Promoter Activity in Dicotyledonous Plants It was evaluated whether this enhancer would work in dicotyledonous plants. For this, the HMW-GS-43 enhancer was inserted immediately upstream of two promoters that are known to have weak constitutive activity in soybean: P-rp113-1.3 (reverse complement of nt 3442-2818 of SEQ ID NO 14) and P-atad1-1.3 (SEQ ID NO 15). The enhancers were inserted into 2 T-DNA vectors that contain a coding sequence for a luciferase-dsRed fusion protein under control of either the P-rp113-1.3 promoter (pBay02771, SEQ ID NO 14) or the P-atad1-1.3 promoter (pBay02773, sequence identical to pBay02771 except for the promoter sequence), resulting in T-DNA vectors pBay02772 and pBay02774, respectively. The 4 T-DNA vectors were transformed into Agrobacterium and the resulting strains were used for infiltration of Nicotiana benthamiana leaves. FIG. 9 shows the levels of luciferase activity that was measured 2 days after infiltration. The vectors containing the wheat HMW-GS-43 enhancer showed 2- to 4-fold increased levels of promoter activity compared to the vectors without enhancer. These results show that the HMW-GS-43 enhancer is also active in dicot plants.

Example 7: Duplication of the ALMT1B Enhancer Results in an Increased Enhancer Activity The impact of 2 copies of the ALMT1 enhancer on activity of the wheat T6PP promoter was tested (insertion 200 nt upstream of the translation start site). FIG. 10 shows that two copies of the ALMT1B enhancer (2×ALMT1B) increased activity of the T6PP promoter about 4-fold more than the original enhancer sequence whereas the reverse complement (ALMT1B RC) showed a similar expression increase. This showed that impact of the ALMT1 enhancer is dependent on the copy number but independent of the orientation of the enhancer sequence.

SEQUENCE LISTING

```
<160> NUMBER OF SEQ ID NOS: 15

<210> SEQ ID NO 1
<211> LENGTH: 43
<212> TYPE: DNA
<213> ORGANISM: Triticum aestivum
<220> FEATURE:
<223> OTHER INFORMATION: Insertion causing increased activity of the
      HMW-GS promoter

<400> SEQUENCE: 1
gccttaaata tattgtaaaa tattccggca acaacttgtg ggg                43

<210> SEQ ID NO 2
<211> LENGTH: 107
<212> TYPE: DNA
<213> ORGANISM: Triticum aestivum
<220> FEATURE:
<223> OTHER INFORMATION: ALMT1 promoter block B

<400> SEQUENCE: 2 gcagggcga ggtcgtatct ggcagcggcg tgccctgagg aggtcggatc cggcggaggc      60
gcgcgctcgg agaggccgta tccagcggag gcgaccggca gggggg                 107

<210> SEQ ID NO 3
<211> LENGTH: 172
<212> TYPE: DNA
<213> ORGANISM: Triticum aestivum
<220> FEATURE:
<223> OTHER INFORMATION: ALMT1 promoter block A

<400> SEQUENCE: 3
cacgccggct cgtacgtagc gccgtcgtgg tgtccctgg cgactgattt gggcagcgcg      60
gtggatgggt taggaggaat gtgagcgcgc catgtgtttg tccgccagtg cctaactgcc    120
gcactgcctc aaaaggcgcg tgctagggta ctgtacttaa ttagcagcgc cg           172
```

```
<210> SEQ ID NO 4
<211> LENGTH: 97
<212> TYPE: DNA
<213> ORGANISM: Triticum aestivum
<220> FEATURE:
<223> OTHER INFORMATION: ALMT1 promoter block C

<400> SEQUENCE: 4
tccacacgca cgagcagcag gcagtagcac agcgaatgca gatcgggtcc atgatattca      60
ttccccaggc ccccaaataa aacacgtacg dacggtc                               97

<210> SEQ ID NO 5
<211> LENGTH: 175
<212> TYPE: DNA
<213> ORGANISM: Triticum aestivum
<220> FEATURE:
<223> OTHER INFORMATION: Insertion of the VRN-D1c promoter associated
      with increased expression of the wheat Vrn-D1 gene

<400> SEQUENCE: 5
gtcccgagca gtggcgtagc taggggggtgg ccagggtggt ccgtggacca ccctggaatt     60
tccccataac ttgtatatag tgtacgtaaa gaaatatttc tttgaaacta aataaatata    120
tttaaatatt ttcatcaatt gaccaccctg gagtattggt ctggctacgc cactg         175

<210> SEQ ID NO 6
<211> LENGTH: 6016
<212> TYPE: DNA
<213> ORGANISM: Artificial Sequence
<220> FEATURE:
<223> OTHER INFORMATION: Transient expression vector (pBay01160)
      containing the gus gene under control of the 35S2 promoter and the
      rice actin-1 intron

<400> SEQUENCE: 6
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt gggcccggcc ggccgcgatc    420
gctacgtacc tgcaggcccg ggttaattaa gcggccgcaa catggagtca aaaattcaga    480
tcgaggatct aacagaactc gccgtgaaga ctggcgaaca gttcatacag agtcttttac    540
gactcaatga caagaagaaa atcttcgtca acatggtgga gcacgacact ctcgtctact    600
ccaagaatat caaagataca gtctcagaag accaaagggc tattgagact ttcaacaaa     660 gggtaatatc gggaaacctc ctcggattcc attgcccagc tatctgtcac ttcatcaaaa    720
ggacagtaga aaaggaaggt ggcacctaca aatgccatca ttgcgataaa ggaaaggcta    780
tcgttcaaga tgcccctgcc gacagtggtc ccaaagatgg accccaccc acgaggagca     840 tcgtggaaaa agaagacgtt ccaaccacgt cttcaaagca agtggattga tgtgatatct    900
ccactgacgt aagggatgac gcacaatccc actatccttc gcaagaccct tcctctatat    960
aaggaagttc atttcatttg gagaggactg agctcattc tctattact tcagccataa    1020 caaaagaact cttttctctt cttattaaac caggtaacca cccgcccct ctcctctttc    1080
```

```
tttctccgtt ttttttttcc gtctcggtct cgatctttgg ccttggtagt ttgggtgggc    1140
gagaggcggc ttcgtgcgcg cccagatcgg tgcgcgggag gggcgggatc tcgcggctgg    1200
ggctctcgcc ggcgtggatc cggcccggat ctcgcgggga atgggctct cggatgtaga    1260 tctgcgatcc gccgttgttg ggggagatga tggggggttt aaaatttccg ccatgctaaa    1320
caagatcagg aagaggggaa aagggcacta tggtttatat ttttatatat ttctgctgct    1380
tcgtcaggct tagatgtgct agatctttct ttcttctttt tgtgggtaga atttgaatcc    1440
ctcagcattg ttcatcggta gttttttcttt tcatgatttg tgacaaatgc agcctcgtgc    1500
ggagcttttt tgtaggtaga ccatggtccg tcctgtagaa accccaaccc gtgaaatcaa    1560
aaaactcgac ggcctgtggg cattcagtct ggatcgcgaa aactgtggaa ttgatcagcg    1620
ttggtgggaa agcgcgttac aagaaagccg gcaattgct gtgccaggca gttttaacga    1680
tcagttcgcc gatgcagata ttcgtaatta tgcgggcaac gtctggtatc agcgcgaagt    1740
ctttataccg aaaggttggg caggccagc tatcgtgctg cgtttcgatg cggtcactca    1800
ttacggcaaa gtgtgggtca ataatcagga agtgatggag catcagggcg gctatacgcc    1860
atttgaagcc gatgtcacgc cgtatgttat tgccggaaa agtgtacgta agttttctgct    1920 tctacctttg atatatatat aataattatc attaattagt agtaatataa tatttcaaat    1980 attttttca aaataaaaga atgtagtata tagcaattgc ttttctgtag tttataagtg    2040
tgtatatttt aatttataac ttttctaata tatgaccaaa atttgttgat gtgcaggtat    2100
caccgtttgt gtgaacaacg aactgaactg gcagactatc ccgccgggaa tggtgattac    2160
cgacgaaaac ggcaagaaaa agcagtctta cttccatgat ttctttaact atgccggaat    2220
ccatcgcagc gtaatgctct acaccacgcc gaacacctgg gtggacgata tcaccgtggt    2280
gacgcatgtc gcgcaagact gtaaccacgc gtctgttgac tggcaggtgg tggccaatgg    2340
tgatgtcagc gttgaactgc gtgatgcgga tcaacaggtg gttgcaactg acaaggcac    2400 tagcgggact ttgcaagtgg tgaatccgca cctctggcaa ccgggtgaag gttatctcta    2460
tgaactgtgc gtcacagcca aaagccagac agagtgtgat atctaccgc ttcgcgtcgg    2520 catccggtca gtggcagtga agggcgaaca gttcctgatt aaccacaaac cgttctactt    2580
tactggcttt ggtcgtcatg aagatgcgga cttgcgtggc aaaggattcg ataacgtgct    2640
gatggtgcac gaccacgcat taatggactg gattggggcc aactcctacc gtacctcgca    2700
ttacccttac gctgaagaga tgctcgactg ggcagatgaa catggcatcg tggtgattga    2760
tgaaactgct gctgtcggct ttaacctctc tttaggcatt ggtttcgaag cgggcaacaa    2820
gccgaaagaa ctgtacagcg aagaggcagt caacgggaa actcagcaag cgcacttaca    2880
ggcgattaaa gagctgatag cgcgtgacaa aaaccaccca agcgtggtga tgtggagtat    2940
tgccaacgaa ccggataccc gtccgcaagg tgcacgggaa tatttcgcgc cactggcgga    3000
agcaacgcgt aaactcgacc cgacgcgtcc gatcacctgc gtcaatgtaa tgttctgcga    3060
cgctcacacc gataccatca gcgatctctt tgatgtgctg tgcctgaacc gttattacgg    3120
atggtatgtc caaagcggcg atttggaaac ggcagagaag gtactggaaa agaacttct    3180 ggcctggcag gagaaactgc atcagccgat tatcatcacc gaatacggcg tggatacgtt    3240
agccgggctg cactcaatgt acaccgacat gtggagtgaa gagtatcagt gtgcatggct    3300
ggatatgtat caccgcgtct ttgatcgcgt cagcgccgtc gtcggtgaac aggtatggaa    3360
tttcgccgat tttgcgacct cgcaaggcat attgcgcgtt ggcggtaaca agaaagggat    3420
```

```
cttcactcgc gaccgcaaac cgaagtcggc ggcttttctg ctgcaaaaac gctggactgg   3480
catgaacttc ggtgaaaaac cgcagcaggg aggcaaacaa tgattgctag cacgcgtccc   3540
tagacttgta catcttctgg attggccaac ttaattaatg tatgaaataa aaggatgcac   3600
acatagtgac atgctaatca ctataatgtg gcatcaaag ttgtgtgtta tgtgtaatta    3660
ctaattatct gaataagaga aagagatcat ccatatttct tatcctaaat gaatgtcacg   3720
tgtctttata attctttgat gaaccagatg cattttatta accaattccg gcgcgccagc   3780
ttggcgtaat catggtcata gctgtttcct gtgtgaaatt gttatccgct cacaattcca   3840
cacaacatac gagccggaag cataaagtgt aaagcctggg gtgcctaatg agtgagctaa   3900
ctcacattaa ttgcgttgcg ctcactgccc gctttccagt cgggaaacct gtcgtgccag   3960
ctgcattaat gaatcggcca acgcgcgggg agaggcggtt tgcgtattgg gcgctcttcc   4020
gcttcctcgc tcactgactc gctgcgctcg tcgttcggc tgcggcgagc ggtatcagct    4080
cactcaaagg cggtaatacg gttatccaca gaatcagggg ataacgcagg aaagaacatg   4140
tgagcaaaag gccagcaaaa ggccaggaac cgtaaaaagg ccgcgttgct ggcgtttttc   4200
cataggctcc gcccccctga cgagcatcac aaaaatcgac gctcaagtca gaggtggcga   4260
aacccgacag gactataaag ataccaggcg tttccccctg gaagctccct cgtgcgctct   4320
cctgttccga ccctgccgct taccggatac ctgtccgcct ttctcccttc gggaagcgtg   4380
gcgctttctc atagctcacg ctgtaggtat ctcagttcgg tgtaggtcgt tcgctccaag   4440
ctgggctgtg tgcacgaacc ccccgttcag cccgaccgct gcgccttatc cggtaactat   4500
cgtcttgagt ccaacccggt aagacacgac ttatcgccac tggcagcagc cactggtaac   4560
aggattagca gagcgaggta tgtaggcggt gctacagagt tcttgaagtg gtggcctaac   4620
tacggctaca ctagaagaac agtatttggt atctgcgctc tgctgaagcc agttaccttc   4680 ggaaaagag ttggtagctc ttgatccggc aaacaaacca ccgctggtag cggtggtttt    4740
tttgtttgca agcagcagat tacgcgcaga aaaaaaggat ctcaagaaga tcctttgatc   4800
ttttctacgg ggtctgacgc tcagtggaac gaaaactcac gttaagggat tttggtcatg   4860
agattatcaa aaaggatctt cacctagatc cttttaaatt aaaaatgaag ttttaaatca   4920
atctaaagta tatatgagta aacttggtct gacagttacc aatgcttaat cagtgaggca   4980
cctatctcag cgatctgtct atttcgttca tccatagttg cctgactccc cgtcgtgtag   5040
ataactacga tacgggaggg cttaccatct ggccccagtg ctgcaatgat accgcgagac   5100
ccacgctcac cggctccaga tttatcagca ataaaccagc cagccggaag ggccgagcgc   5160
agaagtggtc ctgcaacttt atccgcctcc atccagtcta ttaattgttg ccgggaagct   5220
agagtaagta gttcgccagt taatagtttg cgcaacgttg ttgccattgc tacaggcatc   5280
gtggtgtcac gctcgtcgtt tggtatggct tcattcagct ccggttccca acgatcaagg   5340
cgagttacat gatcccccat gttgtgcaaa aaagcggtta gctccttcgg tcctccgatc   5400
gttgtcagaa gtaagttggc cgcagtgtta tcactcatgg ttatggcagc actgcataat   5460
tctcttactg tcatgccatc cgtaagatgc ttttctgtga ctggtgagta ctcaaccaag   5520
tcattctgag aatagtgtat gcggcgaccg agttgctctt gcccggcgtc aatacgggat   5580
aataccgcgc cacatagcag aactttaaaa gtgctcatca ttggaaaacg ttcttcgggg   5640
cgaaaactct caaggatctt accgctgttg agatccagtt cgatgtaacc cactcgtgca   5700
cccaactgat cttcagcatc ttttactttc accagcgttt ctgggtgagc aaaaacagga   5760
aggcaaaatg ccgcaaaaaa gggaataagg gcgacacgga aatgttgaat actcatactc   5820
```

| | | |
|---|---|---|
| ttccttttc aatattattg aagcatttat cagggttatt gtctcatgag cggatacata | 5880 |
| tttgaatgta tttagaaaaa taaacaaata ggggttccgc gcacatttcc ccgaaaagtg | 5940 |
| ccacctgacg tctaagaaac cattattatc atgacattaa cctataaaaa taggcgtatc | 6000 |
| acgaggccct ttcgtc | 6016 |

<210> SEQ ID NO 7
<211> LENGTH: 5591
<212> TYPE: DNA
<213> ORGANISM: Artificial Sequence
<220> FEATURE:
<223> OTHER INFORMATION: Synthetic vector construct (pBay01697)

<400> SEQUENCE: 7

| | | |
|---|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt gggcccggcc ggccgcgatc | 420 |
| gctacgtacc tgcaggcccg ggttaattaa gcggccgcag gcctaactgg cccttaaggg | 480 |
| taccgaaggc cagacgggca cactgaatca tggccgcaag acccttcctc tatataagga | 540 |
| agttcatttc atttggagag gactcgagct catttctcta ttacttcagc cataacaaaa | 600 |
| gaactctttt ctcttcttat taaaccaggt aaccacccg ccctctcct ctttcttct | 660 |
| ccgttttttt tttccgtctc ggtctcgatc tttggccttg gtagtttggg tgggcgagag | 720 |
| gcggcttcgt gcgcgcccag atcggtgcgg gggaggggcg ggatctcgcg gctgggctc | 780 |
| tcgccggcgt ggatccggcc cggatctcgc ggggaatggg gctctcggat gtagatctgc | 840 |
| gatccgccgt tgttggggga gatgatgggg ggtttaaaat ttccgccatg ctaaacaaga | 900 |
| tcaggaagag gggaaaaggg cactatggtt tatatttta tatatttctg ctgcttcgtc | 960 |
| aggcttagat gtgctagatc tttctttctt cttttttgtgg gtagaatttg aatccctcag | 1020 |
| cattgttcat cggtagtttt tcttttcatg atttgtgaca aatgcagcct cgtgcggagc | 1080 |
| ttttttgtag gtagaccatg gtccgtcctg tagaaacccc aacccgtgaa atcaaaaaac | 1140 |
| tcgacggcct gtgggcattc agtctggatc gcgaaaactg tggaattgat cagcgttggt | 1200 |
| gggaaagcgc gttacaagaa agccgggcaa ttgctgtgcc aggcagtttt aacgatcagt | 1260 |
| tcgccgatgc agatattcgt aattatgcgg gcaacgtctg gatcagcgc gaagtctta | 1320 |
| taccgaaagg ttgggcaggc cagcgtatcg tgctgcgttt cgatgcggtc actcattacg | 1380 |
| gcaaagtgtg gtcaataat caggaagtga tggagcatca gggcggctat acgccatttg | 1440 |
| aagccgatgt cacgccgtat gttattgccg ggaaaagtgt acgtaagttt ctgcttctac | 1500 |
| ctttgatata tatataataa ttatcattaa ttagtagtaa tataatattt caaatatttt | 1560 |
| tttcaaaata aaagaatgta gtatatagca attgcttttc tgtagtttat aagtgtgtat | 1620 |
| attttaattt ataactttc taatatatga ccaaatttg ttgatgtgca ggtatcaccg | 1680 |
| tttgtgtgaa caacgaactg aactggcaga ctatcccgcc gggaatggtg attaccgacg | 1740 |
| aaaacggcaa gaaaaagcag tcttacttcc atgatttctt taactatgcc ggaatccatc | 1800 |

```
gcagcgtaat gctctacacc acgccgaaca cctgggtgga cgatatcacc gtggtgacgc   1860
atgtcgcgca agactgtaac cacgcgtctg ttgactggca ggtggtggcc aatggtgatg   1920
tcagcgttga actgcgtgat gcggatcaac aggtggttgc aactggacaa ggcactagcg   1980
ggactttgca agtggtgaat ccgcacctct ggcaaccggg tgaaggttat ctctatgaac   2040
tgtgcgtcac agccaaaagc cagacagagt gtgatatcta cccgcttcgc gtcggcatcc   2100
ggtcagtggc agtgaagggc gaacagttcc tgattaacca caaaccgttc tactttactg   2160
gctttggtcg tcatgaagat gcggacttgc gtggcaaagg attcgataac gtgctgatgg   2220
tgcacgacca cgcattaatg gactggattg gggccaactc ctaccgtacc tcgcattacc   2280
cttacgctga agagatgctc gactgggcag atgaacatgg catcgtggtg attgatgaaa   2340
ctgctgctgt cggctttaac ctctctttag gcattggttt cgaagcgggc aacaagccga   2400
aagaactgta cagcgaagag gcagtcaacg gggaaactca gcaagcgcac ttacaggcga   2460
ttaaagagct gatagcgcgt gacaaaaacc acccaagcgt ggtgatgtgg agtattgcca   2520
acgaaccgga tacccgtccg caaggtgcac gggaatattt cgcgccactg gcggaagcaa   2580
cgcgtaaact cgacccgacg cgtccgatca cctgcgtcaa tgtaatgttc tgcgacgctc   2640
acaccgatac catcagcgat ctctttgatg tgctgtgcct gaaccgttat tacggatggt   2700
atgtccaaag cggcgatttg gaaacggcag agaaggtact ggaaaaagaa cttctggcct   2760
ggcaggagaa actgcatcag ccgattatca tcaccgaata cggcgtggat acgttagccg   2820
ggctgcactc aatgtacacc gacatgtgga gtgaagagta tcagtgtgca tggctggata   2880
tgtatcaccg cgtctttgat cgcgtcagcg ccgtcgtcgg tgaacaggta tggaatttcg   2940
ccgattttgc gacctcgcaa ggcatattgc gcgttggcgg taacaagaaa gggatcttca   3000
ctcgcgaccg caaaccgaag tcggcggctt ttctgctgca aaaacgctgg actggcatga   3060
acttcggtga aaaaccgcag cagggaggca acaatgatt gctagcacgc gtccctagac   3120
ttgtacatct tctggattgg ccaacttaat taatgtatga aataaaagga tgcacacata   3180
gtgacatgct aatcactata atgtgggcat caaagttgtg tgttatgtgt aattactaat   3240
tatctgaata agagaaagag atcatccata tttcttatcc taaatgaatg tcacgtgtct   3300
ttataattct ttgatgaacc agatgcattt tattaaccaa ttccggcgcg ccagcttggc   3360
gtaatcatgg tcatagctgt ttcctgtgtg aaattgttat ccgctcacaa ttccacacaa   3420
catacgagcc ggaagcataa agtgtaaagc ctggggtgcc taatgagtga gctaactcac   3480
attaattgcg ttgcgctcac tgcccgcttt ccagtcggga aacctgtcgt gccagctgca   3540
ttaatgaatc ggccaacgcg cggggagagg cggtttgcgt attgggcgct cttccgcttc   3600
ctcgctcact gactcgctgc gctcggtcgt tcggctgcgg cgagcggtat cagctcactc   3660
aaaggcggta atacggttat ccacagaatc aggggataac gcaggaaaga acatgtgagc   3720
aaaaggccag caaaaggcca ggaaccgtaa aaaggccgcg ttgctggcgt ttttccatag   3780
gctccgcccc cctgacgagc atcacaaaaa tcgacgctca gtcagaggt ggcgaaaccc   3840 gacaggacta taaagatacc aggcgtttcc ccctggaagc tccctcgtgc gctctcctgt   3900
tccgaccctg ccgcttaccg gatacctgtc cgcctttctc ccttcgggaa gcgtggcgct   3960
ttctcatagc tcacgctgta ggtatctcag ttcggtgtag tcgttcgct ccaagctggg   4020 ctgtgtgcac gaaccccccg ttcagcccga ccgctgcgcc ttatccggta actatcgtct   4080
tgagtccaac ccggtaagac acgacttatc gccactggca gcagccactg gtaacaggat   4140
tagcagagcg aggtatgtag gcggtgctac agagttcttg aagtggtggc ctaactacgg   4200
```

```
ctacactaga agaacagtat ttggtatctg cgctctgctg aagccagtta ccttcggaaa    4260
aagagttggt agctcttgat ccggcaaaca aaccaccgct ggtagcggtg ttttttttgt    4320
ttgcaagcag cagattacgc gcagaaaaaa aggatctcaa aagatccctt tgatcttttc    4380 tacgggtct gacgctcagt ggaacgaaaa ctcacgttaa gggattttgg tcatgagatt     4440
atcaaaaagg atcttcacct agatcctttt aaattaaaaa tgaagtttta atcaatcta     4500 aagtatatat gagtaaactt ggtctgacag ttaccaatgc ttaatcagtg aggcacctat    4560
ctcagcgatc tgtctatttc gttcatccat agttgcctga ctccccgtcg tgtagataac    4620
tacgatacgg gagggcttac catctggccc cagtgctgca atgataccgc gagacccacg    4680
ctcaccggct ccagatttat cagcaataaa ccagccagcc ggaagggccg agcgcagaag    4740
tggtcctgca actttatccg cctccatcca gtctattaat tgttgccggg aagctagagt    4800
aagtagttcg ccagttaata gtttgcgcaa cgttgttgcc attgctacag gcatcgtggt    4860
gtcacgctcg tcgtttggta tggcttcatt cagctccggt tcccaacgat caaggcgagt    4920
tacatgatcc cccatgttgt gcaaaaaagc ggttagctcc ttcggtcctc cgatcgttgt    4980
cagaagtaag ttggccgcag tgttatcact catggttatg gcagcactgc ataattctct    5040
tactgtcatg ccatccgtaa gatgctttc tgtgactggt gagtactcaa ccaagtcatt     5100
ctgagaatag tgtatgcggc gaccgagttg ctcttgcccg gcgtcaatac gggataatac    5160
cgcgccacat agcagaactt taaaagtgct catcattgga aaacgttctt cggggcgaaa    5220
actctcaagg atcttaccgc tgttgagatc cagttcgatg taacccactc gtgcacccaa    5280
ctgatcttca gcatctttta ctttcaccag cgtttctggg tgagcaaaaa caggaaggca    5340
aaatgccgca aaaagggaa taagggcgac acggaaatgt tgaatactca tactcttcct     5400
ttttcaatat tattgaagca tttatcaggg ttattgtctc atgagcggat acatatttga    5460
atgtatttag aaaaataaac aaataggggt tccgcgcaca tttccccgaa aagtgccacc    5520
tgacgtctaa gaaaccatta ttatcatgac attaacctat aaaaataggc gtatcacgag    5580 gcccttttcgt c                                                        5591
```

<210> SEQ ID NO 8
<211> LENGTH: 5729
<212> TYPE: DNA
<213> ORGANISM: Artificial Sequence
<220> FEATURE:
<223> OTHER INFORMATION: Synthetic vector construct (pBay01701)

<400> SEQUENCE: 8

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt gggcccggcc ggccgcgatc    420
gctacgtacc tgcaggcccg ggttaattaa gcggccgcag gcctaactgg ccctatcgtt    480
caagatgccc ctgccgacag tggtcccaaa gatggacccc cacccacgag gagcatcgtg    540
gaaaaagaag acgttccaac cacgtcttca aagcaagtgg attgatgtga tatctccact    600
```

```
gacgtaaggg atgacgggta ccgaaggcca gacgggcaca ctgaatcatg ccgcaagac    660 ccttcctcta tataaggaag ttcatttcat ttggagagga ctcgagctca tttctctatt   720
acttcagcca taacaaaaga actcttttct cttcttatta aaccaggtaa ccaccccgcc   780
cctctcctct ttctttctcc gtttttttt tccgtctcgg tctcgatctt tggccttggt    840
agtttgggtg ggcgagaggc ggcttcgtgc gcgcccagat cggtgcgcgg gaggggcggg   900
atctcgcggc tggggctctc gccggcgtgg atccggcccg gatctcgcgg ggaatgggc    960 tctcggatgt agatctgcga tccgccgttg ttgggggaga tgatgggggg tttaaaattt   1020
ccgccatgct aaacaagatc aggaagaggg gaaaagggca ctatggttta tattttata    1080 tatttctgct gcttcgtcag gcttagatgt gctagatctt tctttcttct ttttgtgggt   1140
agaatttgaa tccctcagca ttgttcatcg gtagttttc ttttcatgat ttgtgacaaa    1200
tgcagcctcg tgcggagctt ttttgtaggt agaccatggt ccgtcctgta gaaacccaa    1260 cccgtgaaat caaaaaactc gacgcctgt gggcattcag tctggatcgc gaaaactgtg    1320
gaattgatca gcgttggtgg gaaagcgcgt tacaagaaag ccgggcaatt gctgtgccag   1380
gcagttttaa cgatcagttc gccgatgcag atattcgtaa ttatgcgggc aacgtctggt   1440
atcagcgcga agtctttata ccgaaaggtt gggcaggcca gcgtatcgtg ctgcgtttcg   1500
atgcggtcac tcattacggc aaagtgtggg tcaataatca ggaagtgatg gagcatcagg   1560
gcggctatac gccatttgaa gccgatgtca cgccgtatgt tattgccggg aaaagtgtac   1620
gtaagtttct gcttctacct ttgatatata tataataatt atcattaatt agtagtaata   1680
taatatttca aatattttt tcaaaataaa gaatgtagt atatagcaat tgcttttctg     1740
tagtttataa gtgtgtatat tttaattat aacttttcta atatatgacc aaaatttgtt    1800
gatgtgcagg tatcaccgtt tgtgtgaaca acgaactgaa ctggcagact atcccgccgg   1860
gaatggtgat taccgacgaa aacggcaaga aaaagcagtc ttacttccat gatttcttta   1920
actatgccgg aatccatcgc agcgtaatgc tctacaccac gccgaacacc tgggtggacg   1980
atatcaccgt ggtgacgcat gtcgcgcaag actgtaacca cgcgtctgtt gactggcagg   2040
tggtggccaa tggtgatgtc agcgttgaac tgcgtgatgc ggatcaacag gtggttgcaa   2100
ctggacaagg cactagcggg actttgcaag tggtgaatcc gcacctctgg caaccgggtg   2160
aaggttatct ctatgaactg tgcgtcacag ccaaaagcca gacagagtgt gatatctacc   2220
cgcttcgcgt cggcatccgg tcagtggcag tgaagggcga acagttcctg attaaccaca   2280
aaccgttcta ctttactggc tttggtcgtc atgaagatgc ggacttgcgt ggcaaaggat   2340
tcgataacgt gctgatggtg cacgaccacg cattaatgga ctggattggg gccaactcct   2400
accgtacctc gcattaccct tacgctgaag agatgctcga ctgggcagat gaacatggca   2460
tcgtggtgat tgatgaaact gctgctgtcg gctttaacct ctctttaggc attggtttcg   2520
aagcgggcaa caagccgaaa gaactgtaca gcgaagaggc agtcaacggg gaaactcagc   2580
aagcgcactt acaggcgatt aaagagctga tagcgcgtga caaaaaccac caagcgtgg   2640 tgatgtggag tattgccaac gaaccggata cccgtccgca aggtgcacgg gaatatttcg   2700
cgccactggc ggaagcaacg cgtaaactcg accgacgcg tccgatcacc tgcgtcaatg   2760
taatgttctg cgacgctcac accgatacca tcagcgatct ctttgatgtg ctgtgcctga   2820
accgttatta cggatggtat gtccaaagcg gcgatttgga aacggcagag aaggtactgg   2880
aaaaagaact tctggcctgg caggagaaac tgcatcagcc gattatcatc accgaatacg   2940
gcgtggatac gttagccggg ctgcactcaa tgtacaccga catgtggagt gaagagtatc   3000
```

```
agtgtgcatg gctggatatg tatcaccgcg tctttgatcg cgtcagcgcc gtcgtcggtg   3060
aacaggtatg gaatttcgcc gattttgcga cctcgcaagg catattgcgc gttggcggta   3120
acaagaaagg gatcttcact cgcgaccgca aaccgaagtc ggcggctttt ctgctgcaaa   3180
aacgctggac tggcatgaac ttcggtgaaa aaccgcagca gggaggcaaa caatgattgc   3240
tagcacgcgt ccctagactt gtacatcttc tggattggcc aacttaatta atgtatgaaa   3300
taaaaggatg cacacatagt gacatgctaa tcactataat gtgggcatca aagttgtgtg   3360
ttatgtgtaa ttactaatta tctgaataag agaaagagat catccatatt tcttatccta   3420
aatgaatgtc acgtgtcttt ataattcttt gatgaaccag atgcatttta ttaaccaatt   3480
ccggcgcgcc agcttggcgt aatcatggtc atagctgttt cctgtgtgaa attgttatcc   3540
gctcacaatt ccacacaaca tacgagccgg aagcataaag tgtaaagcct ggggtgccta   3600
atgagtgagc taactcacat taattgcgtt gcgctcactg cccgctttcc agtcgggaaa   3660
cctgtcgtgc cagctgcatt aatgaatcgg ccaacgcgcg gggagaggcg gtttgcgtat   3720
tgggcgctct tccgcttcct cgctcactga ctcgctgcgc tcggtcgttc ggctgcggcg   3780
agcggtatca gctcactcaa aggcggtaat acggttatcc acagaatcag gggataacgc   3840
aggaaagaac atgtgagcaa aaggccagca aaaggccagg aaccgtaaaa aggccgcgtt   3900
gctggcgttt ttccataggc tccgcccccc tgacgagcat cacaaaaatc gacgctcaag   3960
tcagaggtgg cgaaacccga caggactata aagataccag gcgtttcccc ctggaagctc   4020
cctcgtgcgc tctcctgttc cgaccctgcc gcttaccgga tacctgtccg cctttctccc   4080
ttcgggaagc gtggcgcttt ctcatagctc acgctgtagg tatctcagtt cggtgtaggt   4140
cgttcgctcc aagctgggct gtgtgcacga accccccgtt cagcccgacc gctgcgcctt   4200
atccggtaac tatcgtcttg agtccaaccc ggtaagacac gacttatcgc cactggcagc   4260
agccactggt aacaggatta gcagagcgag gtatgtaggc ggtgctacag agttcttgaa   4320
gtggtggcct aactacggct acactagaag aacagtattt ggtatctgcg ctctgctgaa   4380
gccagttacc ttcggaaaaa gagttggtag ctcttgatcc ggcaaacaaa ccaccgctgg   4440
tagcggtggt ttttttgttt gcaagcagca gattacgcgc agaaaaaaag gatctcaaga   4500
agatcctttg atcttttcta cggggtctga cgctcagtgg aacgaaaact cacgttaagg   4560
gattttggtc atgagattat caaaaaggat cttcacctag atcctttaa attaaaaatg   4620 aagttttaaa tcaatctaaa gtatatatga gtaaacttgg tctgacagtt accaatgctt   4680
aatcagtgag gcacctatct cagcgatctg tctatttcgt tcatccatag ttgcctgact   4740
ccccgtcgtg tagataacta cgatacggga gggcttacca tctggcccca gtgctgcaat   4800
gataccgcga gacccacgct caccggctcc agatttatca gcaataaacc agccagccgg   4860
aagggccgag cgcagaagtg gtcctgcaac tttatccgcc tccatccagt ctattaattg   4920
ttgccgggaa gctagagtaa gtagttcgcc agttaatagt ttgcgcaacg ttgttgccat   4980
tgctacaggc atcgtggtgt cacgctcgtc gtttggtatg gcttcattca gctccggttc   5040
ccaacgatca aggcgagtta catgatcccc catgttgtgc aaaaaagcgg ttagctcctt   5100
cggtcctccg atcgttgtca gaagtaagtt ggccgcagtg ttatcactca tggttatggc   5160
agcactgcat aattctctta ctgtcatgcc atccgtaaga tgcttttctg tgactggtga   5220
gtactcaacc aagtcattct gagaatagtg tatgcggcga ccgagttgct cttgcccggc   5280
gtcaatacgg gataataccg cgccacatag cagaacttta aaagtgctca tcattggaaa   5340
```

```
acgttcttcg gggcgaaaac tctcaaggat cttaccgctg ttgagatcca gttcgatgta    5400
acccactcgt gcacccaact gatcttcagc atctttact  ttcaccagcg tttctgggtg    5460
agcaaaaaca ggaaggcaaa atgccgcaaa aagggaata  agggcgacac ggaaatgttg    5520
aatactcata ctcttccttt ttcaatatta ttgaagcatt tatcagggtt attgtctcat    5580
gagcggatac atatttgaat gtatttagaa aaataaacaa atagggttc  cgcgcacatt    5640 tccccgaaaa gtgccacctg acgtctaaga aaccattatt atcatgacat taacctataa   5700
aaataggcgt atcacgaggc cctttcgtc                                      5729
```

<210> SEQ ID NO 9
<211> LENGTH: 6439
<212> TYPE: DNA
<213> ORGANISM: Artificial Sequence
<220> FEATURE:
<223> OTHER INFORMATION: TEX vector (pKA63) containing the firefly
      luciferase coding sequence under control of maize ubiquitin-1
      promotor.

<400> SEQUENCE: 9

```
ctgcagtgca gcgtgacccg gtcgtgcccc tctctagaga taatgagcat tgcatgtcta      60
agttataaaa aattaccaca tatttttttt gtcacacttg tttgaagtgc agtttatcta     120
tctttataca tatatttaaa ctttactcta cgaataatat aatctatagt actacaataa     180
tatcagtgtt ttagagaatc atataaatga acagttagac atggtctaaa ggacaattga    240 gtatttgac  aacaggactc tacagtttta tcttttagt  gtgcatgtgt tctccttttt    300
ttttgcaaat agcttcacct atataatact tcatccattt tattagtaca tccatttagg    360
gtttagggtt aatggttttt atagactaat tttttagta  catctatttt attctatttt    420
agcctctaaa ttaagaaaac taaaactcta ttttagtttt tttatttaat aatttagata    480
taaaatagaa taaataaag  tgactaaaaa ttaaacaaat acccttaag  aaattaaaaa    540 aactaaggaa acattttct  tgtttcgagt agataatgcc agcctgttaa acgccgtcga    600
tcgacgagtc taacggacac caaccagcga accagcagcg tcgcgtcggg ccaagcgaag    660
cagacggcac ggcatctctg tcgctgcctc tggaccctc  tcgagagttc cgctccaccg    720
ttggacttgc tccgctgtcg gcatccagaa attgcgtggc ggagcggcag acgtgagccg    780
gcacggcagg cggcctcctc ctcctctcac ggcaccggca gctacggggg attccttcc    840 caccgctcct tcgctttccc ttcctcgccc gccgtaataa atagacaccc cctccacacc    900
ctctttcccc aacctcgtgt tgttcggagc gcacacacac acaaccagat ctcccccaaa    960
tccacccgtc ggcacctccg cttcaaggta cgccgctcgt cctcccccc  ccccctctc    1020 taccttctct agatcggcgt tccggtccat gcttagggcc cggtagttct acttctgtcc    1080
atgtttgtgt tagatccgtg tttgtgttag atccgtgcta ctagcgttcg tacacggatg    1140
cgacctgtac gtcagacacg ttctgattgc taacttgcca gtgtttctct ttggggaatc    1200
ctgggatggc tctagccgtt ccgcagacgg gatcgatttc atgattttt  ttgtttcgtt    1260 gcataggtt  tggtttgccc ttttcctta  tttcaatata tgccgtgcac ttgtttgtcg    1320
ggtcatcttt tcatgctttt ttttgtcttg gttgtgatga tgtggtctgg ttgggcggtc    1380
gttctagatc ggagtagaat tctgtttcaa actacctggt ggatttatta attttggatc    1440
tgtatgtgtg tgccatacat attcatagtt acgaattgaa gatgatggat ggaaatatcg    1500
atctaggata ggtatacatg ttgatgcggg ttttactgat gcatatacag agatgctttt    1560
tgttcgcttg gttgtgatga tgtggtgtgg ttgggcggtc gttcattcgt tctagatcgg    1620
```

```
agtagaatac tgtttcaaac tacctggtgt atttattaat tttggaactg tatgtgtgtg    1680
tcatacatct tcatagttac gagtttaaga tggatggaaa tatcgatcta ggataggtat    1740
acatgttgat gtgggtttta ctgatgcata tacatgatgg catatgcagc atctattcat    1800
atgctctaac cttgagtacc tatctattat aataaacaag tatgttttat aattattttg    1860
atcttgatat acttggatga tggcatatgc agcagctata tgtggatttt tttagccctg    1920
ccttcatacg ctatttattt gcttggtact gtttcttttg tcgatgctca ccctgttgtt    1980
tggtgttact tctgcaggtc gaccgccggg gatcaccaaa accatggaag acgccaaaaa    2040
cataaagaaa ggcccggcgc cattctatcc gctggaagat ggaaccgctg agagcaact    2100
gcataaggct atgaagagat acgccctggt tcctggaaca attgctttta cagatgcaca    2160
tatcgaggtg gacatcactt acgctgagta cttcgaaatg tccgttcggt tggcagaagc    2220
tatgaaacga tatgggctga atacaaatca gaatcgtc gtatgcagtg aaaactctct    2280
tcaattcttt atgccggtgt tgggcgcgtt atttatcgga gttgcagttg cgcccgcgaa    2340
cgacatttat aatgaacgtg aattgctcaa cagtatgggc atttcgcagc ctaccgtggt    2400
gttcgtttcc aaaagggggt tgcaaaaaat tttgaacgtg caaaaaaagc tcccaatcat    2460
ccaaaaaatt attatcatgg attctaaaac ggattaccag ggatttcagt cgatgtacac    2520
gttcgtcaca tctcatctac ctcccggttt taatgaatac gattttgtgc cagagtcctt    2580
cgatagggac aagacaattg cactgatcat gaactcctct ggatctactg gtctgcctaa    2640
aggtgtcgct ctgcctcata gaactgcctg cgtgagattc tcgcatgcca gagatcctat    2700
ttttggcaat caaatcattc cggatactgc gattttaagt gttgttccat tccatcacgg    2760
ttttggaatg tttactacac tcggatattt gatatgtgga tttcgagtcg tcttaatgta    2820
tagatttgaa gaagagctgt ttctgaggag ccttcaggat tacaagattc aaagtgcgct    2880
gctggtgcca acctattct ccttcttcgc caaaagcact ctgattgaca atacgatt    2940
atctaatttta cacgaaattg cttctggtgg cgctcccctc tctaaggaag tcggggaagc    3000
ggttgccaag aggttccatc tgccaggtat caggcaagga tatgggctca ctgagactac    3060
atcagctatt ctgattacac ccgagggga tgataaaccg ggcgcggtcg gtaaagttgt    3120
tccatttttt gaagcgaagg ttgtggatct ggataccggg aaaacgctgg gcgttaatca    3180
aagaggcgaa ctgtgtgtga gaggtcctat gattatgtcc ggttatgtaa caatccgga    3240
agcgaccaac gccttgattg acaaggatgg atggctacat tctggagaca tagcttactg    3300
ggacgaagac gaacacttct tcatcgttga ccgcctgaag tctctgatta agtacaaagg    3360
ctatcaggtg gctcccgctg aattggaatc catcttgctc caacacccca acatcttcga    3420
cgcaggtgtc gcaggtcttc ccgacgatga cgccggtgaa cttcccgccg ccgttgttgt    3480
tttggagcac ggaaagacga tgacggaaaa agagatcgtg gattacgtcg ccagtcaagt    3540
aacaaccgcg aaaagttgc gcggaggagt tgtgtttgtg gacgaagtac cgaaaggtct    3600
taccggaaaa ctcgacgcaa gaaaaatcag agagatcctc ataaaggcca agaagggcgg    3660
aaagatcgcc gtgtaattct agcaagcttg acacgctga atcaccagt ctctctctac    3720
aaatctatct ctctctattt tctccataat aatgtgtgag tagttcccag ataagggaat    3780
tagggttcct atagggtttc gctcatgtgt tgagcatata agaaacccttt agtatgtatt    3840
tgtatttgta aaatacttct atcaataaaa tttctaattc ctaaaaccaa aatccagtac    3900
taaaatccag atcatgcatg gtacagcggc cgcgttaacg cgtatactct agagcgatcg    3960
```

```
caagcttggc gtaatcatgg tcatagctgt ttcctgtgtg aaattgttat ccgctcacaa    4020
ttccacacaa catacgagcc ggaagcataa agtgtaaagc ctggggtgcc taatgagtga    4080
gctaactcac attaattgcg ttgcgctcac tgcccgcttt ccagtcggga aacctgtcgt    4140
gccagctgca ttaatgaatc ggccaacgcg cggggagagg cggtttgcgt attgggcgct    4200
cttccgcttc ctcgctcact gactcgctgc gctcggtcgt tcggctgcgg cgagcggtat    4260
cagctcactc aaaggcggta atacggttat ccacagaatc aggggataac gcaggaaaga    4320
acatgtgagc aaaaggccag caaaaggcca ggaaccgtaa aaaggccgcg ttgctggcgt    4380
ttttccatag gctccgcccc cctgacgagc atcacaaaaa tcgacgctca agtcagaggt    4440
ggcgaaaccc gacaggacta taaagatacc aggcgtttcc ccctggaagc tccctcgtgc    4500
gctctcctgt tccgaccctg ccgcttaccg gatacctgtc cgcctttctc ccttcgggaa    4560
gcgtggcgct ttctcaaagc tcacgctgta ggtatctcag ttcggtgtag gtcgttcgct    4620
ccaagctggg ctgtgtgcac gaaccccccg ttcagcccga ccgctgcgcc ttatccggta    4680
actatcgtct tgagtccaac ccggtaagac acgacttatc gccactggca gcagccactg    4740
gtaacaggat tagcagagcg aggtatgtag gcggtgctac agagttcttg aagtggtggc    4800
ctaactacgg ctacactaga agaacagtat ttggtatctg cgctctgctg aagccagtta    4860
ccttcggaaa aagagttggt agctcttgat ccggcaaaca aaccaccgct ggtagcggtg    4920
gtttttttgt ttgcaagcag cagattacgc gcagaaaaaa aggatctcaa gaagatcctt    4980
tgatcttttc tacggggtct gacgctcagt ggaacgaaaa ctcacgttaa gggattttgg    5040
tcatgagatt atcaaaaagg atcttcacct agatcctttt aaattaaaaa tgaagtttta    5100
aatcaatcta agtatatat gagtaaactt ggtctgacag ttaccaatgc ttaatcagtg    5160
aggcacctat ctcagcgatc tgtctatttc gttcatccat agttgcctga ctccccgtcg    5220
tgtagataac tacgatacgg gagggcttac catctggccc cagtgctgca atgataccgc    5280
gagacccacg ctcaccggct ccagatttat cagcaataaa ccagccagcc ggaagggccg    5340
agcgcagaag tggtcctgca actttatccg cctccatcca gtctattaat tgttgccggg    5400
aagctagagt aagtagttcg ccagttaata gtttgcgcaa cgttgttgcc attgctacag    5460
gcatcgtggt gtcacgctcg tcgtttggta tggcttcatt cagctccggt tcccaacgat    5520
caaggcgagt tacatgatcc cccatgttgt gcaaaaaagc ggttagctcc ttcggtcctc    5580
cgatcgttgt cagaagtaag ttggccgcag tgttatcact catggttatg gcagcactgc    5640
ataattctct tactgtcatg ccatccgtaa gatgcttttc tgtgactggt gagtactcaa    5700
ccaagtcatt ctgagaatag tgtatgcggc gaccgagttg ctcttgcccg gcgtcaatac    5760
gggataatac cgcgccacat agcagaactt taaaagtgct catcattgga aaacgttctt    5820
cggggcgaaa actctcaagg atcttaccgc tgttgagatc cagttcgatg taacccactc    5880
gtgcacccaa ctgatcttca gcatctttta ctttcaccag cgtttctggg tgagcaaaaa    5940
caggaaggca aaatgccgca aaaaagggaa taagggcgac acggaaatgt tgaatactca    6000
tactcttcct ttttcaatat tattgaagca tttatcaggg ttattgtctc atgagcggat    6060
acatatttga atgtatttag aaaaataaac aaataggggt tccgcgcaca tttccccgaa    6120
aagtgccacc tgacgtctaa gaaaccatta ttatcatgac attaacctat aaaaataggc    6180
gtatcacgag gccctttcgt ctcgcgcgtt tcggtgatga cggtgaaaac ctctgacaca    6240
tgcagctccc ggagacggtc acagcttgtc tgtaagcgga tgccgggagc agacaagccc    6300
gtcagggcgc gtcagcgggt gttggcgggt gtcggggctg gcttaactat gcggcatcag    6360
```

```
agcagattgt actgagagtg caccataccc gcaggcaatt ggtacctacg tatgcatggc    6420
gcgccataag cttgcatgc                                                 6439

<210> SEQ ID NO 10
<211> LENGTH: 144
<212> TYPE: DNA
<213> ORGANISM: Phage lambda
<220> FEATURE:
<223> OTHER INFORMATION: Sequence from Escherichia phage Lambda

<400> SEQUENCE: 10
cagggtgtgg aagtaggaca ttttcatgtc aggccacttc tttccggagc ggggttttgc      60
tatcacgttg tgaacttctg aagcggtgat gacgccgagc cgtaatttgt gccacgcatc     120 atcccctgt tcgacagctc tcac                                            144

<210> SEQ ID NO 11
<211> LENGTH: 99
<212> TYPE: DNA
<213> ORGANISM: Artificial Sequence
<220> FEATURE:
<223> OTHER INFORMATION: Sequence including the 43-nt insertion of the
      HMW-GS 1Bx7OE promoter

<400> SEQUENCE: 11
aaaatattcc ggcaacaact tgtgggggcc ttaaatatat tgtaaaatat tccggcaaca      60
acttgtgggg tacatctagt tacagtggaa tattagtga                            99

<210> SEQ ID NO 12
<211> LENGTH: 2951
<212> TYPE: DNA
<213> ORGANISM: Triticum aestivum
<220> FEATURE:
<223> OTHER INFORMATION: Promoter fragment of the wheat B genome ACCase
      gene

<400> SEQUENCE: 12
ataaagctcg aaccaacttc acaatgcata gttcagttcg tgccaaaatt gcaaatctaa      60
cctacatgtt tcgtatctcc acatatttac gaaatatcct agatataacg tgcatatttg    120
gtgtctttgt ggttcttgca aaccgccaac cctgactgaa caccgtccaa agccatgagc    180
gcggggcagc gaaaagtcga cgtgttgcct aaatttacgc gcgcctataa gtaggatgac    240
gacgacgacg atcagcccca acaacagaag ggaaaacttt gttttttgcca ctctagcttc    300 tgcatacttt gcttatgcca ttctagaatt tgacatatca cttttgccac tcttagtttt    360
tgacaataca tcacaattag cgatagtacc cggaggtgca tccacgcata agaaggggt     420 gtttgcacgc ccccactcag ctagctcatg agcaactaca tttgattctc tattacagtg    480
ctcaatagta atctttccga actctcgtaa taactctctg caatcatcta aaactggagc    540
cgccaccata gaatgtccct cattcagacg tatagcatct accacaatag aattatccat    600
cctcaccaag atattattgc accccatact ttgaagtaac tttaaacctt caagttatgc    660
cgccgcttac gcagagacga catctgccac atgctcaagg cgagaagtag aggcagcaat    720
gaaattacct ctgtggtctc taactatcgc cccacatgac cccgtatgca gatcctcaat    780
aaaagacgca tcaacgttta aatttgttg cacaaccaaa acaatgggcc gcgtgttcca    840
tccaggtgca gcagtttgtt tcgccgccgc tcgtttgaag ttaagaggca acgcgtggat    900
ggctagcgca gatcgcaacg acgtctgcac ttgctcccct ctgacctgct gtctacgctg    960
```

```
ccaccatacg atcgcctacc cccgtcaaca agatgaccga acaccaccgg cgacttaaaa    1020
ccaaagatgc acagaacgcg caaaacaaag ggctcaagcg tgtacagtac taaaacccctt   1080 cacggctcgc cattcaaacc cagaaaaccg tgcgtttatt ttgcactata agcacgacag    1140
tacgatatca aatggacgtc atgacccact caaccgctac tgaccttaat cgaacaccgc    1200
ccatgctacg aatgcgaaac aacaaatacc gacgtgttcc ccgaatttcc gcgtgtccat    1260
aaatagaacc tccgcgacgt cgtcgaccag ccccgacaac agaaccggca cacgcgtttc    1320
acacactgtt ttctccggtg gcgacgacgt tgcgcaggga agggaaggaa cgtcacggtc    1380
ggggcaggtc cgatccgccc aaccaccgaa ccttaatcca acaacgacgc cgttctaatc    1440
cacccatgac gttctccccc acggccgccc gcccgcccgc ctgccgccgt ccaccgtcct    1500
ccaaacaggg acacgccaag acgcgccgcg agagcgagcg accacgactc acataatgaa    1560
agaaaaatca aaaccgccgt ccgatgggcc gatcggggcc gtccacttgg cccagcgacg    1620
ggcgtcacgt gcggggcgc cagggggag gcggagtccc cgaagagggc cgggaattta     1680
ttattttagg ccgcacagcc cccatctccc ctcacccct cgggatatcc gcccgctcgc     1740
cagcgcccgc tccactctcc ccccgtctcc ggcaccgtgc gcgccgccgc cgccgctaag    1800
atccagcgcc tcgtccgctc cgccacgcgc cagcgccgag cgcgcgtcgg cccgtccgcc    1860
ccgccgcccc cacccgaggt gcgcctctat ttatccctcc cccccctcgc gtctccccc     1920 attccccct gtcgcttccc ccaggtcag gtcaggtcag gccaggccag gccagatccg      1980
ccgcccgatc cgcctccgct cccggaggtg agcccggccg cccgccgcct tcctccgccg    2040
ttgctctgtt tccgcgcgc ccagccgggg cgctgcgtgg ggtgcttggt tcctgggtgg     2100
cggggagagg gtttaagggt tctgcgctgg acttactgta gtagcagcag gggtttgaaa    2160
ttacgcggcg gagcttgggg ttgggtccct cggagcttgc ttcctgctcc taactgctta    2220
tgcagtgggt aattatggaa tgtggctccc gtgctgtatg cacagtagtc aattatcggt    2280
gattatgact ggtgtggctc gttggaggtg ccctgtgcgg tgcctaacac tgtattattt    2340
catagcttgg gtcggtgtgc ttccatggac acatgctcat gctaagcgca agctgaccca    2400
gggtggttgc acaacagaca tggtgataca ggggtagcgg tccactgttg tagccagttt    2460
gcctccgtac gcaggccttt tccactgttc aatctccact actttgggtg agggagtcgg    2520
gtgtcatttc ggccgtgttg atgatacctg ctgtcataat acactttgag cgttggtatt    2580
gagctgggaa tggcagatgc tgttttttc tctccccctc ccacctgttg atctagctgc     2640
tgtattaatt tacctgccat ctgtattagt tatgaaagct tagaatcatc tgccttgtac    2700
tttttgtacg tacctgtgtc atgggagtga tcgcacacgt tatctgtttt agtcaagagc    2760
atcttggatg ttcaaaattt attgagaaag gtcgtgaatt agcccataaa gtacctgttt    2820
cttgtctcta tggactaata atttgtattc acatgcttct gtcaggtttc aaaacccggg    2880
gtttacacac ctttgatggc actgtctctt tgaagaacac tgcatctgcg ctgtttatcc    2940 aaaggggac g                                                          2951
```

<210> SEQ ID NO 13
<211> LENGTH: 1000
<212> TYPE: DNA
<213> ORGANISM: Triticum aestivum
<220> FEATURE:
<223> OTHER INFORMATION: Promoter fragment of the wheat 7A TPP
      (trehalose-6-phosphate phosphatase) gene

<400> SEQUENCE: 13

```
gttgcggcgg acaccggtca tagattctgg atcccttacc gcggggcaaa aggggccgcc      60
actcacgatt cacacgcatg ggggaatgcg gtttggaggc tggttgttgt gttccaacac     120
gtcgtctgtt gcaacggtca agttggggga ggaggctgcg cgtggccag  cttgcggcaa     180 atcggacgac tccgcagcac ctgatctaac tgctcgcatg agagcttact tttggcatgc    240
atcacagcca cgataaaaca aggctaacat agtcttggtc catctataat acatgttgga    300
ccatgcttct ctctccccac taatcgattg ctttctcctt tgaccgtatt tgatcttatt    360
ttttcttcta gtattttatt ttctcttgac attgggttta ttggatgtgc gcggctcccg    420
catgtcagtg accaacatca aaggacactc cttccgccaa agtccctctg attcttcgag    480
tcgattttcc cccttgcaac agatggctat atgtgactga tcgagaaatg gccacacatt    540
tcatccaaaa atgaagaata tttgaatttc acagcctcc  agagcaccac tttgatttga    600
actcgaaata tgaatatagt aaaagggtct acatataatt tgaaagtatt ttgcaggaca    660
aaaacaacaa tgttattctc gaatcttaat ctatagtcgt caattaaatt ttcagaatgt    720
taactgttca tataattgtg caccctgcaa ttgtgaatga gaaaacgaca catgtccact    780
ccggttagaa aaacgcagt  agttccacta gtatgggtac cgacccaacg ccgctccgcc    840
tttataagta ccgacacttc gccattggct tcttcaccca gggaaaaccg gtctggtcgc    900
ctcttcctcg tgaactattc cccactgtca ctgctgggca ccactctcac gcagcgggag    960
gcgcgtgtcg tgagcacacg tgtggttgtt tgcgtgcgcc                         1000

<210> SEQ ID NO 14
<211> LENGTH: 12320
<212> TYPE: DNA
<213> ORGANISM: Artificial Sequence
<220> FEATURE:
<223> OTHER INFORMATION: T-DNA vector (pBay02771) with the soybean
      promoter P-rpl13-1.3 driving a fusion of luciferase and DsRed2 and
      with hppd as plant selection marker

<400> SEQUENCE: 14
aattacaacg gtatatatcc tgccagtact cggccgtcga ccgcggtacc ccggaatttt     60
gtggcgctct atcatagcta taaacctatt cagcacaata cctgcaggtg taggcaggcc    120
tacgtacttc gtaaagcttc gatctagtaa catagatgac accgcgcgcg ataatttatc    180
ctagtttgcg cgctatattt tgttttctat cgcgtattaa atgtataatt gcgggactct    240
aatcataaaa acccatctca taaataacgt catgcattac atgttaatta ttacatgctt    300
aacgtaattc aacagaaatt atatgataat catcgcaaga ccggcaacag gattcaatct    360
taagaaactt tattgccaaa tgtttgaacg atctgcttcg ggcgcgcctc actacaggaa    420
caggtggtgg cggccctcgg tgcgctcgta ctgctccacg atggtgtagt cctcgttgtg    480
ggaggtgatg tccagcttgg cgtccacgta gtagtagccg ggcagctgca cgggcttctt    540
ggccatgtag atggacttga actccaccag gtagtggccg ccgtccttca gcttcagggc    600
cttgtgggtc tcgcccttca gcacgccgtc gcggggtac  aggcgctcgg tggaggcctc    660
ccagcccatg gtcttcttct gcatcacggg gccgtcggag gggaagttca cgccgatgaa    720
cttcaccttg tagatgaagc agccgtcctg caggaggag  tcctgggtca cggtcgccac    780
gccgccgtcc tcgaagttca tcacgcgctc ccacttgaag ccctcgggga aggacagctt    840
cttgtagtcg gggatgtcgg cggggtgctt cacgtacacc ttggagccgt actggaactg    900
gggggacagg atgtcccagg cgaagggcag ggggccgccc ttggtcacct tcagcttcac    960
ggtgttgtgg ccctcgtagg ggcggccctc gccctcgccc tcgatctcga actcgtggcc   1020
```

```
gttcacggtg ccctccatgc gcaccttgaa gcgcatgaac tcggtgatga cgttctcgga   1080
ggaggccatt ggtcctgggt tttcttcaac gtctccagct tgcttaagaa gagaaaagtt   1140
agtagctcca gatcccacgg cgatcttttcc gcccttcttg gcctttatga ggatctctct   1200 gattttctt gcgtcgagtt ttccggtaag acctttcggt acttcgtcca caaacacaac    1260
tcctccgcgc aacttttttcg cggttgttac ttgactggcg acgtaatcca cgatctcttt   1320
ttccgtcatc gtctttccgt gctccaaaac aacaacggcg gcgggaagtt caccggcgtc   1380
atcgtcggga agacctgcga cacctgcgtc gaagatgttg gggtgttgga gcaagatgga   1440
ttccaattca gcgggagcca cctgatagcc tttgtactta atcagagact tcaggcggtc   1500
aacgatgaag aagtgttcgt cttcgtccca gtaagctatg tctccagaat gtagccatcc   1560
atccttgtca atcaaggcgt tggtcgcttc cggattgttt acataaccgg acataatcat   1620
aggacctctc acacacagtt cgcctctttg attaacgccc agcgttttcc cggtatccag   1680
atccacaacc ttcgcttcaa aaatggaac aactttaccg accgcgcccg gtttatcatc     1740
cccctcgggt gtaatcagaa tagctgatgt agtctcagtg agcccatatc cttgcctgat   1800
acctggcaga tggaacctct tggcaaccgc ttcccccgact tccttagaga ggggagcgcc   1860
accagaagca atttcgtgta aattagataa atcgtatttg tcaatcagag tgcttttggc    1920
gaagaaggag aatagggttg gcaccagcag cgcactttga atcttgtaat cctgaaggct   1980
cctcagaaac agctcttctt caaatctata cattaagacg actcgaaatc cacatatcaa   2040
atatccgagt gtagtaaaca ttccaaaacc gtgatggaat ggaacaacac ttaaaatcgc   2100
agtatccgga atgatttgat tgccaaaaat aggatctctg gcatgcgaga atctcacgca   2160
ggcagttcta tgaggcagag cgacaccttt aggcagacca gtagatccag aggagttcat   2220
gatcagtgca attgtcttgt ccctatcgaa ggactctggc acaaaatcgt attcattaaa   2280
accgggaggt agatgagatg tgacgaacgt gtacatcgac tgaaatccct ggtaatccgt   2340
tttagaatcc atgataataa ttttttggat gattgggagc tttttttgca cgttcaaaat    2400
tttttgcaac ccccttttttgg aaacgaacac cacggtaggc tgcgaaatgc ccatactgtt   2460
gagcaattca cgttcattat aaatgtcgtt cgcgggcgca actgcaactc cgataaataa   2520
cgcgcccaac accggcataa agaattgaag agagttttca ctgcatacga cgattctgtg   2580
atttgtattc agcccatatc gtttcatagc ttctgccaac cgaacggaca tttcgaagta   2640
ctcagcgtaa gtgatgtcca cctcgatatg tgcatctgta aaagcaattg ttccaggaac   2700
cagggcgtat ctcttcatag ccttatgcag ttgctctcca gcggttccat cttccagcgg   2760
atagaatggc gccgggcctt tctttatgtt tttgacgtct tccatgttta aactcctctt    2820
cttcttcgtc ccgaaaacaa cacaaacggc acaaggcaaa cccctcttgt tgttgctgc   2880 tggatgctca aggaagagca cattaggggtt tttgaagact cgccttttgt gggttgggtt    2940
ttatgggcca agcccaacac agcctttaac tatttttactt gtgattattt cttgataatt    3000
tctgccacac tgttcttaca tgtacgagaa tagtgagaaa ctactttttt ttttaatatg    3060
attttatact agtgataaat aatttaaacg ataatatcag attattttaa ataattctta     3120
tatatttgat tagtaatttt gtagtgtatt gtattattat actgtttgtt ttaatttaaa    3180
tatatttcaa cttatcaaaa acatatttaa aattataaga ttttttttgtc actattagtg    3240 tcaaatattt atttatttta ttgattatta attttttgtca aaaatttatc caacacctct   3300
aatgaggtat tattttcaa tcacttttttt tttcttaact caattcttta gatttgagtt    3360
```

```
cacttgacca attatgcatt attatttaaa attataaaat gaatatgcat aattaattca    3420
aatataaagt aaaaaacata aaccettaat taactggtca cactagcccg gggaattcga    3480
tatcattacc ctgttatccc taaagcttat taatataact tcgtatagca tacattatac    3540
gaagttatct cgagactgga tttttggtttt aggaattaga aatttttattg atagaagtat    3600 tttacaaata caaatacata ctaagggttt cttatatgct caacacatga gcgaaaccct    3660
ataagaaccc taattccctt atctgggaac tactcacaca ttattataga gagagataga    3720
tttgtagaga gagactggtg atttcagcga agacgtcgtt aactcaatca gcagtaagaa    3780
cacctctacg aacttggtca cgctcaatac tttcgaaaag ttgcgcaaag ttccatgggc    3840
caaagccgtc atctccttta cgctgaataa actcaaagaa aactggaccc attagtgtct    3900
cggaaaaaat ctgcagaagc aacctcttat ctccttccac agaacttcca tcaagtagta    3960
tacctctagc ttggagctgg tcaacgggtt caccgtgatc tggaagtcgt ccttcgagca    4020
tttcgtaata ggtatcggga ggtgcagtca taaacctcat tccaattttc ttcagagcat    4080
cccaagtctt gacaagatcg tctgtcaaaa aagcaacgtg ttggattccc tcaccgttaa    4140
actgcataag gaactcttcg atttgtccag caccettaga actttcctca ttaagaggaa    4200
tcctaatcat tccgtctggt gctgacatag ctttagaagt tagacctgtg tattctccct    4260
taatgtcgaa ataccttgcc tctctaaagt tgaagagttt ctcatagaag ttagcccaat    4320
acaccatcct tcctctatat acattgtggg taaggtgatc gatcactttc aaaccagctc    4380
caactggatt gcgttcgaca ccttccaagt aaacgaagtc gatatcgtaa atggaagagc    4440
cctctccgaa gcggtcaata agatacaaag gagcacctcc aattcccttt atggctggaa    4500
ggttaagttc cattggccca gtatcaatgt gaattggttg ggctcccagt tccaaagcac    4560
gattatatgc cttctggcta tctttaaccc taaaggccat tccacacact gatgaccat     4620 gttcagcggc aaagtaggaa gcaatgctgt ttggctcatt gttcaggatt agatttatct    4680
ctccttgtct gtacagatga acgttcttag acctgtgggt agcgaccttt gtaaaaccca    4740
ttatttcgaa gataggttca agagttccag gagtaggaga agcaaactca ataaactcga    4800
agcccatgag tcccattggg ttttcatata aatctgccat gcaccggatc cttccgccgt    4860
tgctgacgtt gccgaggctt ctggaggagc ggcgggcgac ggggaggctg gcggtggact    4920
tgagcccctg gaacgagcg acggcggtgg ccgacgaggc catcatcacg gtgggcgcca    4980
tagacagcgg cggcaggtac gacagcgtct cgaacttctt gttgccgtag gccggccaca    5040
cctgcatata ttgaactctt ccaccgttgc tgggaagggt ggagaagtcg ttagccttct    5100
tggtggtggg gaaggcggcg ttggacttaa ggccggtgaa cggagccacc atgttggcct    5160 gagcagggc ggtccggcta acggtcgcaa ctgaggagga gatcgaagcc attttttttt     5220
tagtcgagcg ttcgtaaatg gtgaaaattt tcagaaaatt gcttttgctt taaaagaaat    5280
gatttaaatt gctgcaatag aagtagaatg cttgattgct tgagattcgt ttgttttgta    5340
tatgttgtgt tgagaattta ttgtcctctc caaatgaaat gaacttcctt atatagagga    5400
agggtcttgc gaaggatagt gggattgtgc gtcatcccett acgtcagtgg agatatcaca    5460
tcaatccact tgctttgaag acgtggttgg aacgtcttct tttttccacga tgctcctcgt    5520 gggtgggggt ccatctttgg gaccactgtc ggtagaggca tcttgaacga tagcctttcc    5580
tttatcgcaa tgatggcatt tgtaggagcc accttccttt tccactatct tcacaataaa    5640
gtgacagata gctgggcaat ggaatccgag gaggtttccg gatattaccc tttgttgaaa    5700
agtctcaatt gcccetttggt cttctgagac tgtatctttg atatttttgg agtagacaag    5760
```

```
tgtgtcgtgc tccaccagtt atcacatcaa tccacttgct ttgaagacgt ggttggaacg    5820 tcttctttt  ccacgatgct cctcgtgggt gggggtccat ctttgggacc actgtcggca    5880
gaggcatctt caacgatggc cttcctta   tcgcaatgat ggcatttgta ggagccacct    5940
tccttttcca ctatcttcac aataaagtga cagatagctg gcaatggaa  tccgaggagg    6000 tttccggata ttacccttg  ttgaaaagtc tcaattgccc tttggtcttc tgagactgta    6060
tctttgatat ttttggagta gacaagtgtg tcgtgctcca ccagttgact aaagatctaa    6120
cataacttcg tatagcatac attatacgaa gttatacgcg tacgagcggc gaactaataa    6180
ctccgctcta ccgaaagtta cattcgagca tggagccatt tacaattgaa tatatcctgc    6240
cgccgctgcc gctttgcacc cggtggagct tgcatgttgg tttctacgca gaactgagcc    6300
ggttaggcag ataatttcca ttgagaactg agccatgtgc accttccccc caacacggtg    6360
agcgacgggg caacggagtg atccacatgg gacttttaaa catcatccgt cggatggcgt    6420
tgcgagagaa gcagtcgatc cgtgagatca gccgacgcac cgggcaggcg cgcaacacga    6480
tcgcaaagta tttgaacgca ggtacaatcg agccgacgtt cacggtaccg gaacgaccaa    6540
gcaagctagc ttagtaaagc cctcgctaga ttttaatgcg gatgttgcga ttacttcgcc    6600
aactattgcg ataacaagaa aaagccagcc tttcatgata tatctcccaa tttgtgtagg    6660
gcttattatg cacgcttaaa aataataaaa gcagacttga cctgatagtt tggctgtgag    6720
caattatgtg cttagtgcat ctaacgcttg agttaagccg cgccgcgaag cggcgtcggc    6780
ttgaacgaat tgttagacat tatttgccga ctaccttggt gatctcgcct ttcacgtagt    6840
ggacaaattc ttccaactga tctgcgcgcg aggccaagcg atcttcttct tgtccaagat    6900
aagcctgtct agcttcaagt atgacgggct gatactgggc cggcaggcgc tccattgccc    6960
agtcggcagc gacatccttc ggcgcgattt tgccggttac tgcgctgtac caaatgcggg    7020
acaacgtaag cactacattt cgctcatcgc cagcccagtc gggcggcgag ttccatagcg    7080
ttaaggtttc atttagcgcc tcaaatagat cctgttcagg aaccggatca agagttcct    7140 ccgccgctgg acctaccaag gcaacgctat gttctcttgc ttttgtcagc aagatagcca    7200
gatcaatgtc gatcgtggct ggctcgaaga tacctgcaag aatgtcattg cgctgccatt    7260
ctccaaattg cagttcgcgc ttagctggat aacgccacgg aatgatgtcg tcgtgcacaa    7320
caatggtgac ttctacagcg cggagaatct cgctctctcc aggggaagcc gaagtttcca    7380
aaaggtcgtt gatcaaagct cgccgcgttg tttcatcaag ccttacggtc accgtaacca    7440
gcaaatcaat atcactgtgt ggcttcaggc cgccatccac tgcggagccg tacaaatgta    7500
cggccagcaa cgtcggttcg agatggcgct cgatgacgcc aactacctct gatagttgag    7560
tcgatacttc ggcgatcacc gcttccctca tgatgtttaa ctttgtttta gggcgactgc    7620
cctgctgcgt aacatcgttg ctgctccata acatcaaaca tcgacccacg cgtaacgcg    7680 cttgctgctt ggatgcccga ggcatagact gtaccccaaa aaaacagtca taacaagcca    7740
tgaaaaccgc cactgcgccg ttaccaccgc tgcgttcggt caaggttctg gaccagttgc    7800
gtgagcgcat acgctacttg cattacagct tacgaaccga acaggcttat gtccactggg    7860
ttcgtgcctt catccgtttc cacggtgtgc gtcacccggc aacctgggc  agcagcgaag    7920 tcgaggcatt tctgtcctgg ctggcgaacg agcgcaaggt ttcggtctcc acgcatcgtc    7980
aggcattggc ggccttgctg ttcttctacg gcaaggtgct gtgcacggat cagtgagggt    8040
ttgcaactgc gggtcaagga tctggatttc gatcacggca cgatcatcgt gcgggagggc    8100
```

-continued

| | |
|---|---|
| aagggctcca aggatcgggc cttgatgtta cccgagagct tggcacccag cctgcgcgag | 8160 |
| caggatcgat ccgtgcggct gcatgaaatc ctggccggtt tgtctgatgc caagctggcg | 8220 |
| gcctggccgg ccagcttggc cgctgaagaa accgagcgcc gccgtctaaa aaggtgatgt | 8280 |
| gtatttgagt aaaacagctt gcgtcatgcg gtcgctgcgt atatgatgcg atgagtaaat | 8340 |
| aaacaaatac gcaaggggaa cgcatgaagg ttatcgctgt acttaaccag aaaggcgggt | 8400 |
| caggcaagac gaccatcgca acccatctag cccgcgccct gcaactcgcc ggggccgatg | 8460 |
| ttctgttagt cgattccgat ccccagggca gtgcccgcga ttgggcggcc gtgcgggaag | 8520 |
| atcaaccgct aaccgttgtc ggcatcgacc gcccgacgat tgaccgcgac gtgaaggcca | 8580 |
| tcggccggcg cgacttcgta gtgatcgacg gagcgcccca ggcggcggac ttggctgtgt | 8640 |
| ccgcgatcaa ggcagccgac ttcgtgctga ttccggtgga gccaagcccc tacgacatat | 8700 |
| gggccaccgc cgacctggtg gagctggtta agcagcgcat tgaggtcacg gatggaaggc | 8760 |
| tacaagcggc ctttgtcgtg tcgcgggcga tcaaaggcac gcgcatcggc ggtgaggttg | 8820 |
| ccgaggcgct ggccgggtac gagctgccca ttcttgagtc ccgtatcacg cagcgcgtga | 8880 |
| gctacccagg cactgccgcc gccggcacaa ccgttcttga atcagaaccc gagggcgacg | 8940 |
| ctgcccgcga ggtccaggcg ctggccgctg aaattaaatc aaaactcatt tgagttaatg | 9000 |
| aggtaaagag aaaatgagca aaagcacaaa cacgctaagt gccggccgtc cgagcgcacg | 9060 |
| cagcagcaag gctgcaacgt tggccagcct ggcagacacg ccagccatga agcgggtcaa | 9120 |
| ctttcagttg ccggcggagg atcacaccaa gctgaagatg tacgcggtac gccaaggcaa | 9180 |
| gaccattacc gagctgctat ctgaatacat gcgcagcta ccagagtaaa tgagcaaatg | 9240 |
| aataaatgag tagatgaatt ttagcggcta aggaggcgg catggaaaat caagaacaac | 9300 |
| caggcaccga cgccgtggaa tgccccatgt gtggaggaac gggcggttgg ccaggcgtaa | 9360 |
| gcggctgggt tgtctgccgg ccctgcaatg gcactggaac ccccaagccc gaggaatcgg | 9420 |
| cgtgagcggt cgcaaaccat ccggcccggt acaaatcggc gcggcgctgg gtgatgacct | 9480 |
| ggtggagaag ttgaaggccg cgcaggccgc ccagcggcaa cgcatcgagg cagaagcacg | 9540 |
| ccccggtgaa tcgtggcaag cggccgctga tcgaatccgc aaagaatccc ggcaaccgcc | 9600 |
| ggcagccggt gcgccgtcga ttaggaagcc gcccaagggc gacgagcaac cagatttttt | 9660 |
| cgttccgatg ctctatgacg tgggcacccg cgatagtcgc agcatcatgg acgtggccgt | 9720 |
| tttccgtctg tcgaagcgtg accgacgagc tggcgaggtg atccgctacg agcttccaga | 9780 |
| cgggcacgta gaggtttccg cagggccggc cggcatggcc agtgtgtggg attacgacct | 9840 |
| ggtactgatg gcggtttccc atctaaccga atccatgaac cgataccggg aagggaaggg | 9900 |
| agacaagccc ggccgcgtgt tccgtccaca cgttgcggac gtactcaagt tctgccggcg | 9960 |
| agccgatggc ggaaagcaga aagacgacct ggtagaaacc tgcattcggt taaacaccac | 10020 |
| gcacgttgcc atgcagcgta cgaagaaggc caagaacggc cgcctggtga cggtatccga | 10080 |
| gggtgaagcc ttgattagcc gctacaagat cgtaaagagc gaaaccgggc ggccggagta | 10140 |
| catcgagatc gagctagctg attggatgta ccgcgagatc acagaaggca agaacccgga | 10200 |
| cgtgctgacg gttcaccccg attactttt gatcgatccc ggcatcggcc gttttctcta | 10260 |
| ccgcctggca cgccgcgccg caggcaaggc agaagccaga tggttgttca agacgatcta | 10320 |
| cgaacgcagt ggcagcgtcg gagagttcaa gaagttctgt ttcaccgtgc gcaagctgat | 10380 |
| cgggtcaaat gacctgccgg agtacgattt gaaggaggag gcggggcagg ctggcccgat | 10440 |
| cctagtcatg cgctaccgca acctgatcga gggcgaagca tccgccggtt cctaatgtac | 10500 |

```
ggagcagatg ctagggcaaa ttgccctagc aggggaaaaa ggtcgaaaag gtctctttcc      10560
tgtggatagc acgtacattg gaacccaaa gccgtacatt gggaaccgga acccgtacat      10620
tgggaaccca aagccgtaca ttgggaaccg gtcacacatg taagtgactg atataaaaga      10680
gaaaaaaggc gattttttccg cctaaaactc tttaaaactt attaaaactc ttaaaacccg      10740
cctggcctgt gcataactgt ctggccagcg cacagccgaa gagctgcaaa agcgcctac      10800 ccttcggtcg ctgcgctccc tacgccccgc cgcttcgcgt cggcctatcg cggccgctgg      10860
ccgctcaaaa atggctggcc tacggccagg caatctacca gggcgcggac aagccgcgcc      10920
gtcgccactc gaccgccggc gcccacatca aggcaccctg cctcgcgcgt ttcggtgatg      10980
acggtgaaaa cctctgacac atgcagctcc cggagacggt cacagcttgt ctgtaagcgg      11040
atgccgggag cagacaagcc cgtcagggcg cgtcagcggg tgttggcggg tgtcggggcg      11100
cagccatgac ccagtcacgt agcgatagcg gagtgtatac tggcttaact atgcggcatc      11160
agagcagatt gtactgagag tgcaccatat gcggtgtgaa ataccgcaca gatgcgtaag      11220
gagaaaatac cgcatcaggc gctcttccgc ttcctcgctc actgactcgc tgcgctcggt      11280
cgttcggctg cggcgagcgg tatcagctca ctcaaaggcg gtaatacggt tatccacaga      11340
atcaggggat aacgcaggaa agaacatgtg agcaaaaggc cagcaaaagg ccaggaaccg      11400
taaaaaggcc gcgttgctgg cgttttttcca taggctccgc cccccctgacg agcatcacaa      11460 aaatcgacgc tcaagtcaga ggtggcgaaa cccgacagga ctataaagat accaggcgtt      11520
tccccctgga agctccctcg tgcgctctcc tgttccgacc ctgccgctta ccggatacct      11580
gtccgccttt ctcccttcgg gaagcgtggc gctttctcat agctcacgct gtaggtatct      11640
cagttcggtg taggtcgttc gctccaagct gggctgtgtg cacgaacccc ccgttcagcc      11700
cgaccgctgc gccttatccg gtaactatcg tcttgagtcc aacccggtaa gacacgactt      11760
atcgccactg gcagcagcca ctggtaacag gattagcaga gcgaggtatg taggcggtgc      11820
tacagagttc ttgaagtggt ggcctaacta cggctaaact agaaggacag tatttggtat      11880
ctgcgctctg ctgaagccag ttaccttcgg aaaaagagtt gatagctctt gatccggcaa      11940
acaaaccacc gctggtagcg gtggtttttt tgtttgcaag cagcagatta cgcgcagaaa      12000
aaaaggatct caagaagatc cggaaaacgc aagcgcaaag agaaagcagg tagcttgcag      12060
tgggcttaca tggcgatagc tagactgggc ggttttatgg acagcaagcg aaccggaatt      12120
gccagattcg aagctcggtc ccgtgggtgt tctgtcgtct cgttgtacaa cgaaatccat      12180
tcccattccg cgctcaagat ggcttcccct cggcagttca tcagggctaa atcaatctag      12240
ccgacttgtc cggtgaaatg ggctccactc caacagaaac aatcaaacaa acatacacag      12300
cgacttattc acacgcgaca                                                 12320
```

<210> SEQ ID NO 15
<211> LENGTH: 622
<212> TYPE: DNA
<213> ORGANISM: Brassica napus
<220> FEATURE:
<223> OTHER INFORMATION: Promoter region of the ATPase family AAA
     domain-containing protein 1 gene of Brassica napus

<400> SEQUENCE: 15

```
aagacccatt ctaaaaaagg aagtaaaatc taccatgttg acggttgtat agtaggctta        60
tagtgcagtg attatagcca tcatactcta acaacaataa gtaaataatc acatgcattc       120
attatagagc tttatgactt ttttttcaaaa aaaatagttg ttattgtatt tgtatatgaa       180
```

```
tactatatac tgtttatact catattcaat aattttatga ttggttgaat tatatttagc      240
aaaaaatttg aaaaatattc attcatgatt tttttcttaa ataacttaaa gtacggaaag      300
gaagaaatat attattttgt tcagcactat ggatataata agtcggtcaa gttattttga      360
tatccgacca ataatgcaaa attaaacgca cacatacaaa cagtacatac aataaagttg      420
caggttttat ttaattttga tttataaatt gacctgggag agtaatcatt ttacatgaaa      480
atctctctga attaattatt cttttccat tttcgcgtct atcctccttt ctcctcctat      540
ctcttctctc tatctaatct atcgggaacc accaagcggt tcgttcttct tcttggatca      600
atcaacgcga aacgaagtca at                                              622
```

What is claimed is:

1. A method for enhancing expression derived from a plant promoter comprising functionally linking to a promoter one or more nucleic acid expression enhancing nucleic acid (NEENA) molecules heterologous to said promoter, wherein the one or more NEENA molecules consists of the sequence of SEQ ID NO: 2, wherein enhancer activity of the one or more NEENA molecules is independent of the orientation of the one or more NEENA molecules with respect to the promoter.

2. A method for producing a plant or part thereof with, compared to a respective control plant or part thereof, enhanced expression of one or more nucleic acid molecule comprising the steps of
   a) introducing into the plant or part thereof one or more NEENA molecules defined in claim 1, and
   b) functionally linking said one or more NEENA molecules to a promoter and to a nucleic acid molecule being under the control of said promoter, wherein the one or more NEENA molecules are heterologous to said promoter, and wherein enhancer activity of the one or more NEENA molecules is independent of the orientation of the one or more NEENA molecules with respect to the promoter.

3. The method of claim 1, comprising the steps of
   a) providing an expression construct comprising the one or more NEENA molecules functionally linked to a promoter heterologous to said one or more NEENA molecules and
   b) integrating said expression construct comprising said one or more NEENA molecules into the genome of said plant or part thereof.

4. The method of claim 1, wherein said one or more NEENA molecules are functionally linked to a promoter upstream of the translational start site of the nucleic acid molecule the expression of which is under the control of said promoter.

5. The method of claim 1, wherein said one or more NEENA molecules are functionally linked to a constitutive promoter within the 5'UTR of the nucleic acid molecule the expression of which is under the control of said promoter.

6. The method of claim 1, wherein said one or more NEENA molecules is functionally linked to a tissue specific, developmental specific or inducible promoter within the 5'UTR of the nucleic acid molecule the expression of which is under the control of said promoter.

7. A recombinant expression construct comprising
   A) one or more nucleic acid expression enhancing nucleic acid (NEENA) molecules consisting of the sequence of SEQ ID NO: 2,
   B) one or more promoters functionally linked to the one or more NEENA molecules, wherein the one or more promoters are heterologous to the one or more NEENA molecules, and
   C) one or more expressed nucleic acid molecules,
      wherein enhancer activity of the one or more NEENA molecules is independent of the orientation of the one or more NEENA molecules with respect to the one or more promoters.

8. A cell or plant or part of a plant comprising the recombinant expression construct of claim 7.

9. The cell, plant or part of a plant of claim 8, selected or derived from the group consisting of bacteria, and plants.

10. A cell culture, seed, plant part or plant propagation material, comprising the recombinant expression construct of claim 7.

11. The method of claim 3, further comprising regenerating a plant or part thereof comprising said one or more expression construct.

* * * * *